(12) United States Patent
Chen et al.

(10) Patent No.: US 12,098,396 B2
(45) Date of Patent: *Sep. 24, 2024

(54) POLYMERASE VARIANTS FOR TEMPLATE-INDEPENDENT ENZYMATIC NUCLEIC ACIDS SYNTHESIS AND KIT COMPRISING THE SAME

(71) Applicant: Cheng-Yao Chen, Hsinchu (TW)

(72) Inventors: Cheng-Yao Chen, Hsinchu (TW); Yi-Wen Cheng, Hsinchu (TW); Tsu-Ying Wu, Hsinchu (TW); Yu-Ting Hung, Hsinchu (TW); Wen-Ting Chen, Hsinchu (TW)

(73) Assignee: Cheng-Yao Chen, Hsinchu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/936,816

(22) Filed: Sep. 29, 2022

(65) Prior Publication Data
US 2023/0103994 A1    Apr. 6, 2023

Related U.S. Application Data

(60) Provisional application No. 63/249,819, filed on Sep. 29, 2021.

(51) Int. Cl.
*C12N 9/12* (2006.01)
*C12N 15/09* (2006.01)

(52) U.S. Cl.
CPC ......... *C12N 9/1252* (2013.01); *C12N 9/1247* (2013.01); *C12N 15/09* (2013.01); *C12Y 207/07007* (2013.01)

(58) Field of Classification Search
None
See application file for complete search history.

(56) References Cited

U.S. PATENT DOCUMENTS

| | | |
|---|---|---|
| 2013/0130320 A1 | 5/2013 | Holliger |
| 2016/0032377 A1* | 2/2016 | Chen .................. C12N 9/1252 506/26 |
| 2017/0355970 A1 | 12/2017 | Chen |
| 2021/0147927 A1 | 5/2021 | Bomati |

OTHER PUBLICATIONS

Chica et al. Curr Opin Biotechnol. Aug. 2005; 16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7 (Year: 2011).*
Yoshikuni et al. Curr Opin Chem Biol. Apr. 2007;11(2):233-9. (Year: 2007).*
Accession A0A5C0XMA4. Nov. 13, 2019. (Year: 2019).*

* cited by examiner

*Primary Examiner* — Christian L Fronda
(74) *Attorney, Agent, or Firm* — Winston Hsu

(57) ABSTRACT

Provided herein relates to DNA polymerase variants and kits including the same, where the DNA polymerase variant has an improved function and activity of performing template-independent nucleic acids synthesis using canonical nucleotides and non-canonical nucleotide analogues in a thermo-tolerant manner.

27 Claims, 17 Drawing Sheets
Specification includes a Sequence Listing.

```
Tgo       - - - - - - - - - - - - - - - - - - - - - - - - - - - - - - - - - - - - - - - - - - - - - - - - - - - - - - - - KATIDP- - - - - IEKKLLDY RQRAI - - - - - - - KILAN SFYGYYGYAK 501
Kod1      - - - - - - - - - - - - - - - - - - - - - - - - - - - - - - - - - - - - - - - - - - - - - - - - - - - - - - - - KATIDP- - - - - IERKLLDY RQRAI - - - - - - - KILAN SYYGYYGYAR 501
9°N       - - - - - - - - - - - - - - - - - - - - - - - - - - - - - - - - - - - - - - - - - - - - - - - - - - - - - - - - KATVDP- - - - - LEKKLLDY RQRAI - - - - - - - KILAN SFYGYYGYAK 501
Pfu       - - - - - - - - - - - - - - - - - - - - - - - - - - - - - - - - - - - - - - - - - - - - - - - - - - - - - - - - KETQDP- - - - - IEKILLDY RQKAI - - - - - - - KLLAN SYYGYYGYAK 502
Vent      - - - - - - - - - - - - - - - - - - - - - - - - - - - - - - - - - - - - - - - - - - - - - - - - - - - - - - - - KSTIDP- - - - - IEKKMLDY RQRAI - - - - - - - KVLAN SHYGYLAFPM 504
Mma       - - - - - - - - - - - - - - - - - - - - - - - - - - - - - - - - - - - - - - - - - - - - - - - - - - - - - - - - REKAEKGE FDEEYQILDY EQRSI - - - - - - - KILLN SFYGYSGYAR 517
Mac       - - - - - - - - - - - - - - - - - - - - - - - - - - - - - - - - - - - - - - - - - - - - - - - - - - - - - - - - KRTSDEN- - - - - EHRVLDA TQLAI - - - - - - - KVSAN SVYGFTGAQV 581
hPOLD     - - - - - - - - - - - - - - - - - - - - - - - - - - - - - - - - - - - - - - - - - - - - - - - - - - - - - - - - AKETDP- - - - - LRRQVLDG RQLAL - - - - - - - KISAN SVYGFTGATV 708
ScePOLD   - - - - - - - - - - - - - - - - - - - - - - - - - - - - - - - - - - - - - - - - - - - - - - - - - - - - - - - - RDEKDP- - - - - FKRDVLNG RQLAL - - - - - - - KVMAN AIYGYLGWVG 715
Pis       - - - - - - - - - - - - - - - - - - - - - - - - - - - - - - - - - - - - - - - - - - - - - - - - - - - - - - - - KKYPPDSP - - EFKILDE RQRAL - - - - - - - KVFIN ATYGVFGAET 524
Sso       - - - - - - - - - - - - - - - - - - - - - - - - - - - - - - - - - - - - - - - - - - - - - - - - - - - - - - - - KKAKNPNN SEEQKLLYDV VQRAM - - - - - - - KIIMN AFYGVLGSSG 617
Pae       - - - - - - - - - - - - - - - - - - - - - - - - - - - - - - - - - - - - - - - - - - - - - - - - - - - - - - - - NQPLS- - - - - - QAL - - - - - - - - - - - - - - - - - KIIMN AFYGVLGTTA 509
Eco       - - - - - - - - - - - - - - - - - - - - - - - - - - - - - - - - - - - - - - - - - - - - - - - - - - - - - - - - NKPLS- - - - - - QAL - - - - - - - - - - - - - - - - - SLYGALGNVW 507
RB69      NGEIIKEALH NPNLSVDEPL DVDYRFDFSD EIKEKIKKLS AKSLNEMLFR AQRTEVAGMT AQINRKLLIN SLYGALGNIH 574
T4        NAEAIKKIIM KGAGSCSTKP EVERYVKFSD DFLNELSNYT ESVLNSLIEE CEKAATLANT NQLNRKILIN SLYGALGNIH 571
Phi29     SNVDLELMKE HYDLYNVEYI SGLKFKATTG LFKDFIDKWT YIKTTSEGAI KQLA - - - - - - - - - - - KLMLN SLYGKFASNP 397
Consensus - - - - - - - - - - - - - - - - - - - - - - - - - - - - - - - - - - - - - - - - - - - - - - - - - - - - - - - - KKTIDP- - - - - IEKKLLDY RQRAI - - - - - - - KILAN SFYGYLGYAK Tgo       ARWYCKECAE SVTAWG-RQY IETTIREIEE KFG- - - - - - - - - - - - - - - - - - - - - - - - - - - - - - - - - - - - - - - - - - - - - - - - - - - - - - - F KVLYADTDGF FATIPG- - - - 550
Kod1      ARWYCKECAE SVTAWG-REY ITMTIKEIEE KYG- - - - - - - - - - - - - - - - - - - - - - - - - - - - - - - - - - - - - - - - - - - - - - - - - - - - - - - F KVIYSDTDGF FATIPG- - - - 550
9°N       ARWYCKECAE SVTAWG-REY IEMVIRELEE KFG- - - - - - - - - - - - - - - - - - - - - - - - - - - - - - - - - - - - - - - - - - - - - - - - - - - - - - - F KVLYADTDGL HATIPG- - - - 550
Pfu       ARWYCKECAE SVTAWG-RKY IELVWKELEE KFG- - - - - - - - - - - - - - - - - - - - - - - - - - - - - - - - - - - - - - - - - - - - - - - - - - - - - - - F KVLYIDTDGL YATIPG- - - - 551
Vent      ARWYCKECAE SVTAWG-RHY IEMTIREIEE KFG- - - - - - - - - - - - - - - - - - - - - - - - - - - - - - - - - - - - - - - - - - - - - - - - - - - - - - - F KVIYADTDGF FATIPG- - - - 553
Mma       ARWYSRDCAE ITTHLG-RQY IQKTIEEAEN -FG- - - - - - - - - - - - - - - - - - - - - - - - - - - - - - - - - - - - - - - - - - - - - - - - - - - - - - - F YSKW-A - - - 564
Mac       ARLYSLTLAN AVTSFG-RSN ILNTRDLING RIGKIVLRNS AALLEEAGK LSPQDRIVEL SVAYGDTDSV FVHCKA- - - 656
hPOLD     GKLPCLEISQ SVTGFG-RQM IEEKTKQLVES KY- - - - - - - - - - - - - - - - - - - - - - - - - - - - - - - - - - TVENGYSTSA KVVYGDTDSV MCRFGV- - - 765
ScePOLD   GKLPCLAISS SVTAYG-RTM ILKTKTAVQE KY- - - - - - - - - - - - - - - - - - - - - - - - - - - - - - - - - - CIKNGYKHDA VVVYGDTDSV MVKFGT- - - 772
Pis       ARWYKREVAE SVTAFA-RAI LKDVIEQARR E- - - - - - - - - - - - - - - - - - - - - - - - - - - - - - - - - - - - - - - - - - - - - - - - - - - - - LGI VVVVGDTDSL FVKKHG- - - 572
Sso       FPLYAPAVAE SVTALG-RYV ITSTVKKARE E- - - - - - - - - - - - - - - - - - - - - - - - - - - - - - - - - - - - - - - - - - - - - - - - - - - - - GL TVLYGDTDSL FLLNPP- - - 665
Pae       CRFFDPRLAS SITLRG-HRI MRRTRELIEA Q- - - - - - - - - - - - - - - - - - - - - - - - - - - - - - - - - - - - - - - - - - - - - - - - - - - - - GY TVIYGDTDST FVWLGS- - - 557
Eco       CRFFDPRLAS SITMRG-HQI MRQTKALIEA Q- - - - - - - - - - - - - - - - - - - - - - - - - - - - - - - - - - - - - - - - - - - - - - - - - - - - - GY DVIYGDTDST FVWLKG- - - 555
RB69      FRYYDLRNAT AITTFG-QMA LQWIERKVNE YLNEVCGTEG EAF- - - - - - - - - - - - - - - - - - - - - - - - - - - - - - - - - - - -VLYGDTDSI YVSADKIIDK 635
T4        FRYYDLRNAT AITIFG-QVG IQWIARKINE YLNKVCGTND EDF- - - - - - - - - - - - - - - - - - - - - - - - - - - - - - - - - - - -IAAGDTDSV YVCVDKVIEK 632
Phi29     DVTGKVPYLK ENGALGFRLG EEETKDPVYT PMGVFITAWA RYTTITAAQA CYD - - - - - - - - - - - - - - - - - - - - - - - - - - - - - - RIIYCDTDSI HLT- - - - - 463
Consensus ARWYCXECAE SVTAXG-RQY IEXTIREIEE KFG- - - - - - - - - - - - - - - - - - - - - - - - - - - - - - - - - - - - - - - - - - - - - - - - - - - - - - - F KVLYGDTDSX FVTIPG- - - -
```

| | | 1,300 | | | 1,320 | | 1,340 | | 1,360 | |
|---|---|---|---|---|---|---|---|---|---|---|
| Tgo | ----RYQKTR | QVGLGAW--L | KPK-T---- | ---------- | ---------- | ---------- | ---------- | ---------- | ---------- | 773 |
| Kod1 | ----RYQKTR | QVGLSAW--L | KPKGT---- | ---------- | ---------- | ---------- | ---------- | ---------- | ---------- | 774 |
| 9°N | ----RYQKTK | QVGLGAW--L | KVKGKK--- | ---------- | ---------- | ---------- | ---------- | ---------- | ---------- | 775 |
| Pfu | ----RYQKTR | QVGLTSW--L | NIK-KS--- | ---------- | ---------- | ---------- | ---------- | ---------- | ---------- | 775 |
| Vent | ----RYQSSK | QTGLDAW--L | K-----R-- | ---------- | ---------- | ---------- | ---------- | ---------- | ---------- | 774 |
| Mma | ----KDSK-K | QYTLHHF--L | K-------- | ---------- | ---------- | ---------- | ---------- | ---------- | ---------- | 784 |
| Mac | ----DFD-AK | QKGLFDFEVK | KPEAKKQEKS | SSQKGTNGKI | LEKAPEEKAR | YSENGRVEQR | SLFD----- | ---------- | ----F | 937 |
| hPOLD | FCQPRESELY | QKEVSHLNAL | EERFSRLWTQ | CQRCQGSLHE | DVICTSRDCP | IFYMRKKVRK | DLEDQEQLLR | RFGPPGPEAW | 1107 |
| ScePOLD | NCLARSGELY | IKALYDVRDL | EEKYSRLWTQ | CQRCAGNLHS | EVLCSNKNCD | IFYMRVKVKK | ELQEKVEQLS | K-------W | 1097 |
| Pis | ----KTG | RMERSLLDFL | S-------- | ---------- | ---------- | ---------- | ---------- | ---------- | ---------- | 785 |
| Sso | ----AA | TMSIDSFFSY | PSKGNS--- | ---------- | ---------- | ---------- | ---------- | ---------- | ---------- | 882 |
| Pae | ----DR | QMAL----- | ---------- | ---------- | ---------- | ---------- | ---------- | ---------- | ---------- | 787 |
| Eco | ----TG | QLGL----- | ---------- | ---------- | ---------- | ---------- | ---------- | ---------- | ---------- | 783 |
| RB69 | ----EK | KASLFDM-- | ---------- | ---------- | ---------- | ---------- | ---------- | ---------- | ----F | 903 |
| T4 | ----EE | KASLDFL-- | ---------- | ---------- | ---------- | ---------- | ---------- | ---------- | -FDF | 898 |
| Phi29 | ---------- | ---------- | ---------- | ---------- | ---------- | ---------- | ---------- | ---------- | -FG- | 575 |
| Consensus | ------R-- | --TK QVGLXAW--L | K-------- | ---------- | ---------- | ---------- | ---------- | ---------- | ---------- | |

FIG. 1 (continued)

POLYMERASE VARIANTS FOR TEMPLATE-INDEPENDENT ENZYMATIC NUCLEIC ACIDS SYNTHESIS AND KIT COMPRISING THE SAME

CROSS REFERENCE

This application claims priority to, and the benefit of, U.S. Provisional Application No. 63/249,819, filed on Sep. 29, 2021, the content thereof is incorporated by reference herein.

TECHNICAL FIELD

The present disclosure relates to B-family DNA polymerase variants and kits comprising the same for use particularly in the context of de novo enzymatic nucleic acid synthesis.

SEQUENCE LISTING

The present application is being filed along with a Sequence Listing in electronic format. The Sequence Listing is provided as a file entitled 211019US-sequence listing.XML, created on Jul. 12, 2022, which is 98 kb in size. The information in the electronic format of Sequence Listing is incorporated herein by reference in its entirety.

BACKGROUND

Enzyme-based de novo nucleic acid synthesis is an emerging, non-toxic method to substitute for the decades-old, toxic chemical phosphoramidite-based nucleic acid synthesis.

All living organisms rely on nucleic acid polymerases to efficiently duplicate their DNA. Owing to their DNA duplication function, most nucleic acid polymerases require a template to direct synthesis and incorporation of nucleotides into a growing nucleic acid strand. The template-dependent manner of nucleic acid synthesis requires nucleic acid polymerase to associate with a primer-template DNA before the nucleotide can be added to the 3'-terminus of primer by the polymerase. To ensure a high-fidelity DNA synthesis, nucleic acid polymerases have evolved a robust nucleotide-selection mechanism to accurately choose and incorporate the correct nucleotide corresponding to its complementary templating base during the nucleic acid synthesis. The active-site pocket of nucleic acid polymerase is pre-arranged in a proper geometry for accommodating a correct and matched canonical nucleotide having a normal 3'-hydroxyl (3'-OH) group. Therefore, the elimination or substitution of the 3'-OH group with a bulky, chemical group on the nucleotide, such as 2',3'-dideoxycleotide (ddNTP) and 3'-O-azidomethyl-dNTP, respectively, may significantly alter the nucleotide configuration within the active-site pocket of nucleic acid polymerase and reduce the nucleotide binding affinity and overall DNA synthesis efficiency of nucleic acid polymerase. Likewise, any modifications on the nucleobase or 5'-triphosphate group of the nucleotide will disrupt the interactions between the nucleotide and active-site residues of nucleic acid polymerase and lead to a poor utilization of these modified nucleotides for nucleic acid synthesis by the polymerase.

Unlike most nucleic acid polymerases, the X-family terminal deoxynucleotidyl transferase (Tdt) is a unique class of mesophilic enzyme, which does not rely on a template for adding nucleotides during nucleic acid synthesis. Tdt only requires a short initiator DNA or primer to direct synthesis and incorporation of nucleotides into a growing initiator DNA or primer. Tdt can perform a template-independent DNA synthesis, and the active-site pocket of Tdt is also pre-arranged in a proper geometry for accommodating a canonical nucleotide containing a normal 3'-OH group. Like other nucleic acid polymerases, any substitution of the 3'-OH group with a bulky, chemical group on the nucleotide causes a steric hindrance of nucleotide to fit into the nucleotide-binding pocket of Tdt and results in the reduction of nucleotide-binding affinity and overall DNA synthesis activity of Tdt. Naturally, the template-independent DNA synthesis function of Tdt makes it a primary choice for its application in de novo enzymatic DNA synthesis. However, several intrinsic properties of Tdt, such as limited thermal stability (mesophilic enzyme), preference for certain nucleotide incorporation, intolerance to a larger substitution of the 3'-OH group on the nucleotide and unsatisfactory synthesis efficiency, among others, present a barrier for a practical enzymatic DNA synthesis application.

To broaden the enzymatic DNA synthesis applications, alternative nucleic acid polymerases and their derivatives, which are thermostable and capable of accommodating various non-canonical nucleotide analogues, such as reversible terminator and dye-terminator nucleotides, remain an unmet need.

SUMMARY OF THE INVENTION

Owing to the diverse structure-function relationships mentioned above, the naturally occurring nucleic acid polymerases cannot readily utilize canonical nucleotides and nucleotide analogues as a substrate for de novo nucleic acid synthesis. Thus, the tailor-made, modified nucleic acid polymerase is a prerequisite for exerting the utilities of a variety of nucleic acid synthesis applications.

The inventor has discovered the novel positions/regions in the amino acid sequences of B-family DNA polymerase variants that play crucial parts in endowing the said polymerases with a template-independence and an enhancing nucleotide substrate binding affinity of said polymerases for both canonical and modified nucleotides, thereby improving the nucleic acid synthesis efficiency in the template-independent nucleic acid synthesis method.

Accordingly, in one aspect, the present disclosure provides a B-family DNA polymerase variant comprising: a motif Exo I, a motif Exo II, a motif Exo III, a motif A, a motif B, and a motif C corresponding respectively to the positions 349 to 364, 450 to 476, 590 to 608, 706 to 730, 843 to 855, and 940 to 956 of a consensus sequence (SEQ ID NO:1); a plurality of amino acid substitutions at a position residing in a motif selected from a motif Exo I, a motif Exo II, a motif Exo III, a motif A, a motif B, a motif C, or the combination thereof.

In one embodiment, the B-family DNA polymerase variant is modified from a wild-type B-family DNA polymerase having an amino acid sequence selected from the group consisting of SEQ ID NOs: 2, 3, 4, 5, 6, 7, 8, 9, 10, 11, 12, 13, 14, 15, 16 and 17.

In one embodiment, the wild-type B-family DNA polymerase is *Thermococcus gorgonarius* DNA polymerase (Tgo), *Thermococcus kodakarensis* DNA polymerase (Kod1), *Thermococcus* sp. (strain 9°N-7) DNA polymerase (9°N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase DNA polymerase (Mac), *Pyro-*

*baculum islandicum* DNA polymerase (Pis), *Sulfolobus solfataricus* DNA polymerase (Sso), human DNA polymerase delta catalytic p125 subunit (hPOLD), *Saccharomyces cerevisiae* DNA polymerase delta catalytic subunit (ScePOLD), *Pseudomonas aeruginosa* DNA polymerase II (Pae), *Escherichia coli* DNA polymerase II (Eco), *Escherichia* phage RB69 DNA polymerase (RB69), *Escherichia* phage T4 DNA polymerase (T4), or *Bacillus* phage Phi29 DNA polymerase (Phi29).

In one embodiment, the B-family DNA polymerase variants provided herein have deficient 3' to 5' exonuclease activity.

In one embodiment, the amino acid L or M corresponding to position 715 of SEQ ID NO:1 is substituted with A, F, H, I, Q, S, W, or Y; the amino acid Y corresponding to position 716 of SEQ ID NO:1 is not substituted or substituted with A, C, D, F, G, H, I, K, L, M, N, or Q; and the amino acid P of corresponding to position 717 of SEQ ID NO:1 is not substituted or substituted with A, G, S, or T.

In one embodiment, the B-family DNA polymerase variant having deficient 3' to 5' exonuclease activity is derived from *Thermococcus gorgonarius* DNA polymerase (Tgo) having a wild-type amino acid sequence of SEQ ID NO:2; and wherein the amino acid L at position 408 of SEQ ID NO: 2 is substituted with A, F, H, I, Q, S, W, or Y; the amino acid Y at position 409 of SEQ ID NO: 2 is not substituted or substituted with A, C, D, F, G, H, I, K, L, M, N, or Q; and the amino acid P at position 410 of SEQ ID NO: 2 is not substituted or substituted with A, G, S, or T.

In one embodiment, the B-family DNA polymerase variant having deficient 3' to 5' exonuclease activity is derived from *Thermococcus gorgonarius* DNA polymerase (Tgo) having a wild-type amino acid sequence of SEQ ID NO: 2; and wherein the amino acid L at position 408 of SEQ ID NO: 2 is substituted with A, F, H, I, Q, S, W, or Y; the amino acid Y at position 409 of SEQ ID NO: 2 is not substituted or substituted with A, C, D, F, G, H, I, K, L, M, N, or Q; the amino acid P at position 410 of SEQ ID NO: 2 is not substituted or substituted with A, G, S, or T; and the amino acid A at position 485 of SEQ ID NO: 2 is substituted with C, D, E, F, G, H, K, L, R, T, or Y.

In one embodiment, the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein the amino acid L at position 408 of SEQ ID NO: 3 is substituted with A, F, H, I, Q, S, W, or Y; the amino acid Y at position 409 of SEQ ID NO: 3 is not substituted or substituted with A, C, D, F, G, H, I, K, L, M, N, or Q; and the amino acid P at position 410 of SEQ ID NO: 3 is not substituted or substituted with A, G, S, or T.

In one embodiment, the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein the amino acid L at position 408 of SEQ ID NO: 3 is substituted with A, F, H, I, Q, S, W, or Y; the amino acid Y at position 409 of SEQ ID NO: 3 is not substituted or substituted with A, C, D, F, G, H, I, K, L, M, N, or Q; the amino acid P at position 410 of SEQ ID NO: 3 is not substituted or substituted with A, G, S, or T; and the amino acid A at position 485 of SEQ ID NO: 3 is substituted with C, D, E, F, G, H, K, L, R, T, or Y.

In one embodiment, the B-family DNA polymerase variant having deficient 3' to 5' exonuclease activity is derived from *Thermococcus* sp. (strain 9°N-7) DNA polymerase (9°N) having a wild-type amino acid sequence of SEQ ID NO: 4; and wherein the amino acid L at position 408 of SEQ ID NO: 4 is substituted with A, F, H, I, Q, S, W, or Y; the amino acid Y at position 409 of SEQ ID NO: 4 is not substituted or substituted with A, C, D, F, G, H, I, K, L, M, N, or Q; and the amino acid P at position 410 of SEQ ID NO: 4 is not substituted or substituted with A, G, S, or T.

In one embodiment, the B-family DNA polymerase variant having deficient 3' to 5' exonuclease activity is derived from *Thermococcus* sp. (strain 9°N-7) DNA polymerase (9°N) having a wild-type amino acid sequence of SEQ ID NO: 4; and wherein the amino acid L at position 408 of SEQ ID NO: 4 is substituted with A, F, H, I, Q, S, W, or Y; the amino acid Y at position 409 of SEQ ID NO: 4 is not substituted or substituted with A, C, D, F, G, H, I, K, L, M, N, or Q; the amino acid P at position 410 of SEQ ID NO: 4 is not substituted or substituted with A, G, S, or T; and the amino acid A at position 485 of SEQ ID NO: 4 is substituted with C, D, E, F, G, H, K, L, R, T, or Y.

In one embodiment, the B-family DNA polymerase variant having deficient 3' to 5' exonuclease activity is derived from *Pyrococcus furiosus* DNA polymerase (Pfu) having a wild-type amino acid sequence of SEQ ID NO: 5; and wherein the amino acid L at position 409 of SEQ ID NO: 5 is substituted with A, F, H, I, Q, S, W, or Y; the amino acid Y at position 410 of SEQ ID NO: 5 is not substituted or substituted with A, C, D, F, G, H, I, K, L, M, N, or Q; and the amino acid P at position 411 of SEQ ID NO: 5 is not substituted or substituted with A, G, S, or T.

In one embodiment, the B-family DNA polymerase variant having deficient 3' to 5' exonuclease activity is derived from *Pyrococcus furiosus* DNA polymerase (Pfu) having a wild-type amino acid sequence of SEQ ID NO: 5; and wherein the amino acid L at position 409 of SEQ ID NO: 5 is substituted with A, F, H, I, Q, S, W, or Y; the amino acid Y at position 410 of SEQ ID NO: 5 is s not substituted or substituted with A, C, D, F, G, H, I, K, L, M, N, or Q; the amino acid P at position 411 of SEQ ID NO: 5 is not substituted or substituted with A, G, S, or T; and the amino acid A at position 486 of SEQ ID NO: 5 is substituted with C, D, E, F, G, H, K, L, R, T, or Y.

In one embodiment, the B-family DNA polymerase variant having deficient 3' to 5' exonuclease activity is derived from *Thermococcus litoralis* DNA polymerase (Vent) having a wild-type amino acid sequence of SEQ ID NO: 6; and wherein the amino acid L at position 411 of SEQ ID NO: 6 is substituted with A, F, H, I, Q, S, W, or Y; the amino acid Y at position 412 of SEQ ID NO: 6 is not substituted or substituted with A, C, D, F, G, H, I, K, L, M, N, or Q; and the amino acid P at position 413 of SEQ ID NO: 6 is not substituted or substituted with A, G, S, or T.

In one embodiment, the B-family DNA polymerase variant having deficient 3' to 5' exonuclease activity is derived from *Thermococcus litoralis* DNA polymerase (Vent) having a wild-type amino acid sequence of SEQ ID NO: 6; and wherein the amino acid L at position 411 of SEQ ID NO: 6 is substituted with A, F, H, I, Q, S, W, or Y; the amino acid Y at position 412 of SEQ ID NO: 6 is not substituted or substituted with A, C, D, F, G, H, I, K, L, M, N, or Q; the amino acid P at position 413 of SEQ ID NO: 6 is not substituted or substituted with A, G, S, or T; and the amino acid A at position 488 of SEQ ID NO: 6 is substituted with C, D, E, F, G, H, K, L, R, T, or Y.

In one embodiment, the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein the amino acid L at position 485 of SEQ ID NO:

7 is substituted with A, F, H, I, Q, S, W, or Y; the amino acid Y at position 486 of SEQ ID NO: 7 is not substituted or substituted with A, C, D, F, G, H, I, K, L, M, N, or Q; and the amino acid P at position 487 of SEQ ID NO: 7 is not substituted or substituted with A, G, S, or T.

In one embodiment, the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein the amino acid L at position 485 of SEQ ID NO: 7 is substituted with A, F, H, I, Q, S, W, or Y; the amino acid Y at position 486 of SEQ ID NO: 7 is not substituted or substituted with A, C, D, F, G, H, I, K, L, M, N, or Q; the amino acid P at position 487 of SEQ ID NO: 7 is not substituted or substituted with A, G, S, or T; and the amino acid A at position 565 of SEQ ID NO: 7 is substituted with C, D, E, F, G, H, K, L, R, T, or Y.

In one embodiment, the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein the amino acid M at position 426 of SEQ ID NO: 8 is substituted with A, F, H, I, Q, S, W, or Y; the amino acid Y at position 427 of SEQ ID NO: 8 is not substituted or substituted with A, C, D, F, G, H, I, K, L, M, N, or Q; and the amino acid P at position 428 of SEQ ID NO: 8 is not substituted or substituted with A, G, S, or T.

In one embodiment, the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein the amino acid M at position 426 of SEQ ID NO: 8 is substituted with A, F, H, I, Q, S, W, or Y; the amino acid Y at position 427 of SEQ ID NO: 8 is not substituted or substituted with A, C, D, F, G, H, I, K, L, M, N, or Q; the amino acid P at position 428 of SEQ ID NO: 8 is not substituted or substituted with A, G, S, or T; and the amino acid A at position 508 of SEQ ID NO: 8 is substituted with C, D, E, F, G, H, K, L, R, T, or Y.

In one embodiment, the B-family DNA polymerase variant having deficient 3' to 5' exonuclease activity is derived from *Sulfolobus solfataricus* DNA polymerase (Sso) having a wild-type amino acid sequence of SEQ ID NO: 9; and wherein the amino acid L at position 518 of SEQ ID NO: 9 is substituted with A, F, H, I, Q, S, W, or Y; the amino acid Y at position 519 of SEQ ID NO: 9 is not substituted or substituted with A, C, D, F, G, H, I, K, L, M, N, or Q; and the amino acid P at position 520 of SEQ ID NO: 9 is not substituted or substituted with A, G, S, or T.

In one embodiment, the B-family DNA polymerase variant having deficient 3' to 5' exonuclease activity is derived from *Sulfolobus solfataricus* DNA polymerase (Sso) having a wild-type amino acid sequence of SEQ ID NO: 9; and wherein the amino acid L at position 518 of SEQ ID NO: 9 is substituted with A, F, H, I, Q, S, W, or Y; the amino acid Y at position 519 of SEQ ID NO: 9 is not substituted or substituted with A, C, D, F, G, H, I, K, L, M, N, or Q; the amino acid P at position 520 of SEQ ID NO: 9 is not substituted or substituted with A, G, S, or T; and the amino acid A at position 601 of SEQ ID NO: 9 is substituted with C, D, E, F, G, H, K, L, R, T, or Y.

In some embodiments, the B-family DNA polymerase variants provided herein exhibits activity of synthesizing nucleic acids in a template-independent manner by adding at least one nucleotide selected from the group of naturally occurring nucleotides, nucleotide analogues, or a mixture thereof, to an extendible initiator.

In some embodiments, the extendible initiator comprises a single-stranded oligonucleotide initiator, a blunt-ended double-stranded oligonucleotide initiator, or a mixture thereof.

In some embodiments, the extendible initiator is free form of nucleic acid, in contrast to an immobilized nucleic acid, to be reacted in a liquid phase, such as in liquid medium or other aqueous solutions.

In some embodiments, the extendible initiator is immobilized on a solid support, wherein the solid support comprises a particle, bead, slide, array surface, membrane, flow cell, well, microwell, nano-well, chamber, microfluidic chamber, channel, microfluidic channel, or any other surfaces.

In some embodiments, the at least one nucleotide links with a detectable label.

In some embodiments, the B-family DNA polymerase variant exhibits the activity of incorporating the nucleotide at reaction temperatures ranging from 10° C. to 100° C.

In another aspect, the present disclosure further provides a kit for performing de novo enzymatic nucleic acid synthesis comprising: a B-family DNA polymerase variant derived from a wild-type B-family DNA polymerase having an amino acid sequence selected from the group consisting of SEQ ID NOs: 2, 3, 4, 5, 6, 7, 8, 9, 10, 11, 12, 13, 14, 15, 16, and 17, wherein the B-family DNA polymerase variant exhibits activity of synthesizing nucleic acids in a template-independent manner by adding at least one nucleotide selected from the group of naturally occurring nucleotides, nucleotide analogues, or a mixture thereof, to an extendible initiator, thereby synthesizing a desired nucleic acid sequence.

Accordingly, the present invention relates to the specific B-family DNA polymerase variants that exhibit an improved performance on incorporating a variety of nucleotides for nucleic acid synthesis at various reaction temperatures in the absence of nucleic acid template. More particularly, the de novo nucleic acid synthesis method can be efficiently performed by said thermotolerant B-family DNA polymerase variants with a broad-spectrum of nucleotides and nucleotide analogues.

BRIEF DESCRIPTION OF THE DRAWINGS

The present disclosure will become more readily appreciated with reference to the following description in conjunction with the accompanying drawings.

DETAILED DESCRIPTION OF THE INVENTION

Definition

All terms including descriptive or technical terms which are used herein should be construed as having meanings that are understandable to one of ordinary skill in the art. However, the terms may have different meanings according to an intention of the user, case precedents, or the appearance of new technologies. Also, some terms may be arbitrarily selected by the applicant, and in this case, the meaning of the selected terms will be described in detail in the descriptions of the present disclosure. Thus, the terms used herein are defined based on the meaning of the terms together with the descriptions throughout the specification. In addition, the titles and subtitles may be attached to the description for readability, but these titles do not affect the scope of the present invention.

As used herein, the term "a," "an," or "the" includes plural referents unless expressly and unequivocally limited to one referent. The term "or" is used interchangeably with the term "and/or" unless the context clearly indicates otherwise.

Also, when a part or a method "includes" or "comprises" a component or a step, respectively, unless there is a particular description contrary thereto, the part or the method can further include other components or other steps, not excluding the others.

As used herein, an "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid or aspartate (Asp or D), cysteine (CyS or C), glutamine (Gln or Q), glutamic acid or glutamate (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In cases where "X" residues are undefined, these should be defined as "any amino acid".

The term "functionally equivalent" or "equivalent" is used to describe a specific B-family DNA polymerase (PolB) variant having the substitution or mutation that is considered to occur at the amino acid position in the other PolB, PolB variant according to the sequence alignment, or a reference sequence, which has the same functional or structural role in the enzyme. The equivalent positions may be defined according to homologues, conserved motifs, user-defined, or derived, consensus sequence.

Figure 1:
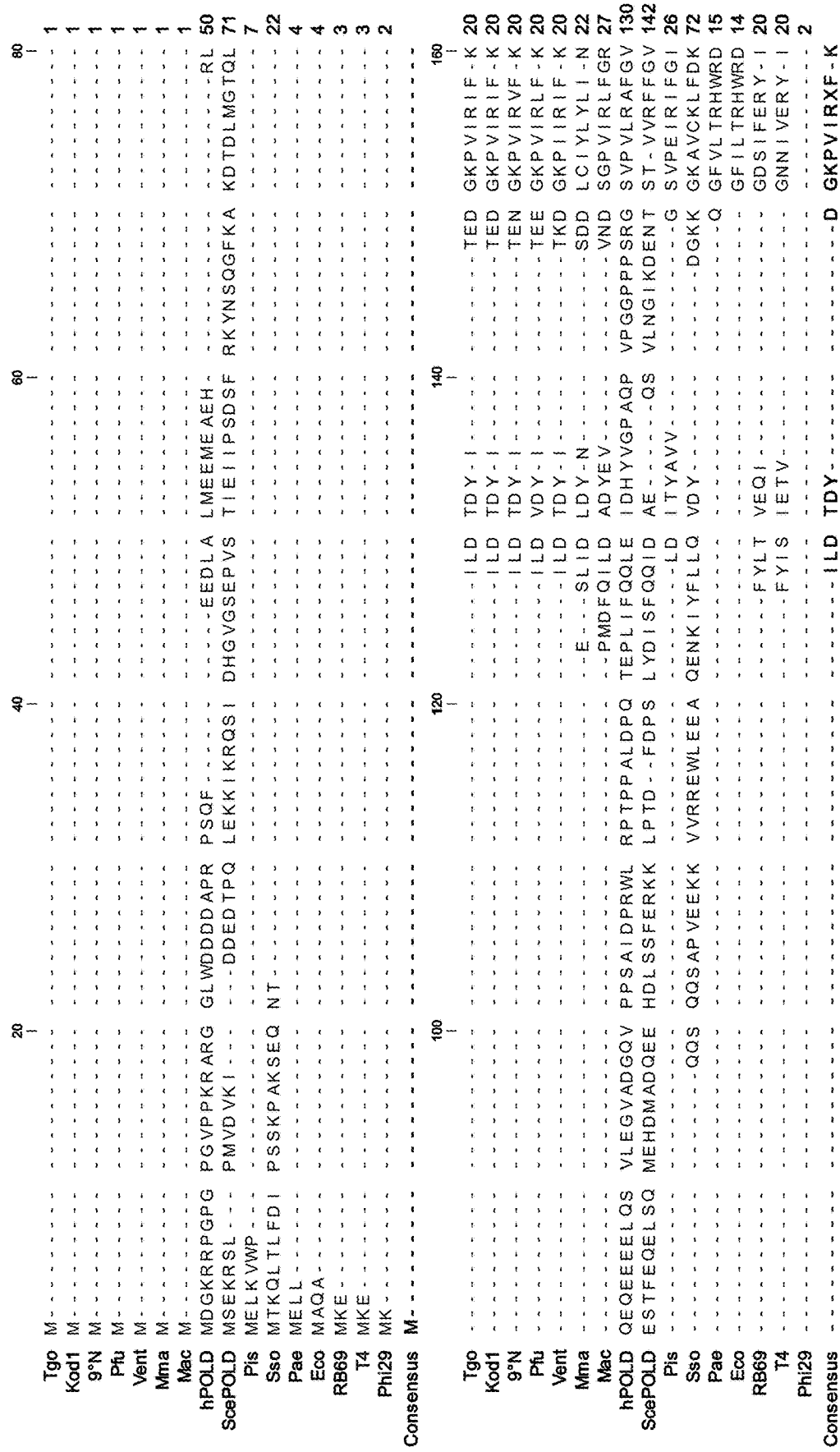
FIG. 1 shows an amino acid sequence alignment of the wild-type B-family DNA polymerases (PolB) related to the present invention and their consensus sequence.

Generally, the homologous PolBs have similar, or identical, amino acid sequences and functional structure, and thereby the equivalent amino acid substitution mutations among different PolBs generally occur at homologous amino acid positions. The term "functionally equivalent" or "equivalent" used herein also encompass mutations that are "homologous" or "positionally equivalent" to a given mutation in view of protein sequence or structural alignment, regardless of the actual function of the mutated amino acid. Practically, the "functionally equivalent", "homologous" and/or "positionally equivalent" amino acid residues of different polymerases can be identified according to the protein sequence or structural alignment. Accordingly, a cross-species alignment was made on multiple wild-type PolBs, as illustrated in FIG. 1, and the consensus sequence (SEQ ID NO: 1) is used as a positional reference sequence.

For example, the substitution of amino acid aspartic acid (D) with alanine (A) at position 141 of the wild-type *Thermococcus kodakarensis* (Kod1) (D141A) amino acid sequence would be functionally equivalent to the amino acid substitution mutation D114A at the conserved residue of wild-type *Escherichia* phage RB69 DNA polymerase (RB69) amino acid sequence. When the positional reference sequence is used to describe these equivalent amino acid substitutions, the functionally equivalent positions of both amino acid residues 141 of Kod1 and amino acid residue 114 of RB69 corresponds to position 354 of the consensus sequence (SEQ ID NO: 1).

The term "conserved" means the segment of polymerase having the same amino acid residue in the homologous or equivalent position of different PolBs from various sources. The term "semi-conserved" used herein refers to the segment of polymerase that has a similar property of amino acid residue or an identical amino acid residue in the homologous position of different PolBs from various sources.

The terms "nucleic acid", "nucleic acid sequence", "oligonucleotide", "polynucleotide", and "nucleic acid fragment" as used herein refer to a deoxyribonucleotide or ribonucleotide sequence in a single-stranded or a double-stranded form of which the sources and length are not limited herein; and generally, includes naturally occurring nucleotides or artificial chemical mimics. The term "nucleic acid" as used herein is interchangeable with the terms including natural or unnatural "oligonucleotide", "polynucleotide", "DNA", "RNA", "gene", "complementary DNA" (cDNA), and "messenger RNA" (mRNA) in use.

The "nucleic acid", "oligonucleotide", or "polynucleotide" used herein refers to a polymer that can be corresponded to a ribose nucleic acid (RNA) or deoxyribose nucleic acid (DNA) polymer, or an analogue thereof. This includes polymers of nucleotides such as RNA and DNA, as well as synthetic forms, modified (e.g., chemically or bio-chemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendentmoieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991)). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence optionally comprises or encodes complementary sequences, in addition to any sequence explicitly indicated.

The nucleic acid as used herein also includes nucleic acid analogue. The term nucleic acid analogue is known to describe compounds or artificial nucleic acids which are functionally or structurally equivalent to naturally existing RNA and DNA. A nucleic acid analogue may have one or more parts of a nucleotide (the phosphate backbone, pentose sugar, and nucleobase) being modified. These modifications on the nucleotide change the structure and geometry of the nucleic acid and its interactions with nucleic acid polymerases. The nucleic acid analogue also encompasses the emerging category of artificial nucleic acids, such as xeno nucleic acids (XNAs), which is designed to have new-to-nature forms of sugar backbone.

Examples of nucleic acid analogues include but are not limited to: the universal bases, such as inosine, 3-nitropyrrole, and 5-nitroindole, which can form a base-pair with all four canonical bases; the phosphate-sugar backbone analogues, such as peptide-nucleic acids (PNA), which affect the backbone properties of the nucleic acid; chemical linker or fluorophore-attached analogues, such as amine-reactive aminoallyl nucleotide, thiol-containing nucleotides, biotin-linked nucleotides, rhodamine-linked nucleotides, and cyanine-linked nucleotides; the fluorescent base analogues, such as 2-aminopurine (2-AP), 3-methylisoxanthopterin (3-MI), 6-methylisoxanthopterin (6-MI), 4-amino-6-methylisoxanthopterin (6-MAP), and 4-dimethylaminopyridine (DMAP); the nucleic acid probes for various genetic applications, such as the oligonucleotide-conjugated with a fluorescent reporter dye (ALEXA, FAM, TET, TAMRA, CY3, CY5, VIC, JOE, HEX, NED, PET, ROX, Texas Red and others) and/or a fluorescent quenchers (BHQs); the molecular beacons (MBs), which are single-stranded nucleic acid probes containing a stem-loop structure and a dual fluorophore-and-quencher label; and the nucleic acid aptamers.

Generally, as used herein, a "template" is a polynucleotide, or a polynucleotide mimic, that contains the desired or unknown target nucleotide sequence. In some instances, the terms "target sequence", "template polynucleotide", "target nucleic acid", "target polynucleotide", "nucleic acid template", "template sequence, and variations thereof, are used interchangeably. Specifically, the term "template" refers to a strand of nucleic acid from which a complimentary copy is synthesized from nucleotides or nucleotide analogues through the replication by a template-dependent or template-directed nucleic acid polymerase. Within a nucleic acid duplex, the template strand is, by the convention definition, depicted and described as the "bottom" strand. Similarly, the non-template strand is often depicted and described as the "top" strand. The "template" strand may also be referred to as the "sense", or "plus", strand and the non-template strand as the "antisense", or "minus", strand.

The term "initiator" refers to a mononucleoside, a mononucleotide, and oligonucleotide, a polynucleotide, or modified analogues thereof, from which a nucleic acid is to be synthesized by nucleic acid polymerase de novo. The term "initiator" may also refer to a xeno nucleic acids (XNA) or a peptide nucleic acid (PNA) having a 3'-hydroxyl group.

The terms "nucleotide incorporation", "analogue incorporation", "incorporating nucleotide" and "incorporating analogue" are known to those skilled in the art and used to describe a process or reaction for nucleic acid synthesis. Thus, as used herein, the term "incorporation" is known to flexibly refer to add one, or more nucleotides, or any specified nucleic acid precursors to the 3'-hydroxyl terminus of a nucleic acid initiator or a primer. For example, the nucleoside triphosphate, such as deoxyguanosine triphosphate (dGTP), is a substrate, or a precursor, for DNA synthesis by DNA polymerase. Once the dGTP is incorporated into the elongated DNA strand, it becomes a deoxyguanosine monophosphate (dGMP) moiety of the newly synthesized DNA. In other words, when a dGTP nucleotide is converted into a dGMP moiety of DNA, the person skilled in the art may say that one dGTP is incorporated into the DNA.

The term "nucleotide analogue" is known to those skilled in the art to describe the chemically modified nucleotides or artificial nucleotides, which are structural mimics of canonical nucleotides. These nucleotide analogues can serve as substrates for nucleic acid polymerases to synthesize nucleic acid. A nucleotide analogue may have one or more altered components of a nucleotide (e.g., the phosphate backbone, pentose sugar, and nucleobase), which changes the structure and configuration of a nucleotide and affects its interactions with other nucleobases and the nucleic acid polymerases. For example, a nucleotide analogue having altered nucleobase may confer alternative base-pairing and base-stacking properties in the DNA or RNA. Furthermore, by way of example, the modification at the base may generate various nucleosides such as inosine, methyl-5-deoxycytidine, deoxyuridine, dimethylamino-5-deoxyuridine, diamino-2,6-purine or bromo-5-deoxyuridine, and any other analogues which permits hybridization. In other exemplary aspects, modifications may take place at the level of sugar moiety (for example, replacement of a deoxyribose by an analogue), and/or at the level of the phosphate group (for example, boronate, alkylphosphonate, or phosphorothioate derivatives). A nucleotide analogue monomer may have a phosphate group selected from a monophosphate, a diphosphate, a triphosphate, a tetraphosphate, a pentaphosphate, and a hexaphosphate.

Other examples of nucleotide analogues also include nucleotides having a removable blocking moiety. Examples of the removable blocking moiety include, but are not limited to, a 3'-O-blocking moiety, a base blocking moiety, and a combination thereof. Examples of the 3'-O-blocking moiety include, but are not limited to, O-azido (O—$N_3$), O-azidomethyl, O-amino, O-allyl, O-phenoxyacetyl, O-methoxyacetyl, O-acetyl, O-(p-toluene)sulfonate, O-phosphate, O-nitrate, O-[4-methoxy]-tetrahydrothiopyranyl, O-tetrahydrothiopyranyl, O-[5-methyl]-tetrahydrofuranyl, O-[2-methyl, 4-methoxy]-tetrahydropyranyl, O-[5-methyl]-tetrahydropyranyl, and O-tetrahydrothiofuranyl, O-2-nitrobenzyl, O-methyl, and O-acyl. Examples of the base blocking moiety may be a reversible dye-terminator. Examples of the reversible dye-terminator include, but are not limited to, a reversible dye-terminator of Illumina MiSeq, a reversible dye-terminator of Illumina HiSeq, a reversible dye-terminator of Illumina Genome Analyzer IIX, a reversible dye-terminator of Helicos Biosciences Heliscope, and a reversible dye-terminator of LaserGen's Lightning Terminators. As used herein, "B-family DNA polymerases (PolBs)" refers to the most common template-dependent nucleic acid polymerases or replicases in all domains of life and many DNA viruses. Like most nucleic acid polymerases, natural PolB s require a duplex primer-template DNA with a free 3'-hydroxyl (3'-OH) group at the primer terminus, all four nucleoside triphosphates (dATP, dTTP, dCTP, and dGTP), and catalytic divalent cations ($Mg^{2+}$ or $Mn^{2+}$, etc.) for catalyzing the nucleotidyl transferase reaction of adding nucleotides to the 3'-OH terminus of a primer. The PolB enzymes, such as bacterial Pol II and archaeal B-family DNA polymerases, are replicative and repair polymerases that inherently contain a catalytic polymerase domain and a 3' to 5' exonucleolytic, or proofreading, domain for removing the mis-incorporated nucleotide from the growing primer strand during nucleic acid replication. The term "3' to 5' exonucleolytic domain" (Exo domain) refers to a region of the amino acid sequence of a polymerase, which exerts the nucleic acid degradation activity from the 3'-terminus of the primer or the polynucleotide chain. Coordinately, the term "catalytic polymerase domain" (Pol domain) refers to a region of the amino acid sequence of a polymerase, which exerts the catalytic DNA/RNA polymerase activity for adding nucleotides to the 3'-terminus of a primer or a polynucleotide chain.

All known structures of PolB catalytic polymerase domain resemble the shape of human right hand, where the key functional regions are characterized as fingers, palm, and thumb subdomains. The most conserved region is the palm subdomain, which contains the essential residues for catalysis. The protein sequence-alignment among various B-family DNA polymerases from different kingdoms of life and DNA viruses reveals that the PolB polymerases generally harbor six semi-conserved or conserved motifs (I-VI) for their essential exonuclease and polymerase functions. The first three sequence-motifs (Exo I, Exo II, Exo III) are in the Exo domain, while the other three motifs (designated as Motif A, B, and C, respectively) reside in the Pol domain (Hopfner et al, Proc. Natl. Acad. Sci. USA 96, 3600-3605, 1999).

As used herein, the term "mutant" in the context of DNA polymerases of the present invention, means a polypeptide, typically recombinant, that comprises one or more amino acid substitutions relative to a corresponding, functional DNA polymerase.

As used herein, in the context of DNA polymerase variants, "corresponding to another sequence" (e.g., regions, fragments, nucleotide or amino acid positions, or the like) is based on the convention of numbering according to nucleotide or amino acid position number and then aligning the sequences in a manner that maximizes the percentage of sequence identity. An amino acid "corresponding to position X of specific sequence" refers to an amino acid in a polypeptide of interest that aligns with the equivalent amino acid of a specified sequence. Generally, as described herein, the amino acid corresponding to a position of a polymerase can be determined using an alignment algorithm such as BLAST and other currently available tools for conducting amino acid sequence alignment. Because not all positions within a given "corresponding region" need to be identical, non-matching positions within a corresponding region may be regarded or define as "corresponding positions". Accordingly, as used herein, referral to an "amino acid position corresponding to amino acid position X of a specified DNA polymerase" refers to equivalent positions, based on alignment, in other DNA polymerases and structural homologues and families.

As used herein, the term "consensus sequence of SEQ ID NO: 1" used herein refers to a reference sequence comprising the conserved amino acids of cross-species B-family DNA polymerase. The consensus sequence of SEQ ID NO: 1 is a virtual sequence and is generated by aligned the following 16 wild-type B-family DNA polymerases to obtain the conserved amino acids: *Thermococcus gorgonarius* DNA polymerase (Tgo), *Thermococcus kodakarensis* DNA polymerase (Kod1), *Thermococcus* sp. (strain 9°N-7) DNA polymerase (9°N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum* DNA polymerase (Pis), *Sulfolobus solfataricus* DNA polymerase (Sso), *Pseudomonas aeruginosa* DNA polymerase II (Pae), *Escherichia coli* DNA polymerase II (Eco), *Escherichia* phage RB69 DNA polymerase (RB69), *Escherichia* phage T4 DNA polymerase (T4), or *Bacillus* phage Phi29 DNA polymerase (Phi29). These PolB sequences are aligned for obtaining the alignment sequence as a reference of functionally equivalent positions.

The positions of motifs Exo I, Exo II, Exo III, A, B, and C are defined by the inventor using the consensus sequence of SEQ ID NO: 1 of the present invention; therefore, it shall be noted that the positions of these motifs defined in the present invention are not totally the same as those described in the literature or prior art.

Objectives

The inventor has discovered PolB variants that have an improved function and activity for utilizing canonical nucleotides, nucleotide analogues, and initiators for synthesizing polynucleotides in a template-independent manner. These PolB variants can efficiently add said canonical nucleotides or nucleotide analogues to said initiator in the absence of a replicative template to synthesize a polynucleotide with a random or defined sequence.

More specifically, the inventor has discovered PolB variants can efficiently catalyze the additions of natural nucleotides and nucleotide analogues to the 3'-OH ends of a single-stranded nucleic acid initiator or a blunt-end duplex nucleic acid initiator, in the absence of replicative template, to generate polynucleotides with desired nucleic acid sequences. Furthermore, the PolB variants provided herein generally have a broader substrate specificity, which means the PolB variants can utilize not only naturally occurring nucleotides, but also varieties of modified nucleotides and nucleic acid analogues for the nucleic acid synthesis de novo. Thus, the modified nucleotide can be further designed for being incorporated to the initiator to generate certain functional polynucleotides. Therefore, these PolB variants broaden the scope and utility of template-independent enzymatic nucleic acid synthesis applications for synthesizing polynucleotides with desired sequences and features.

Protein Sequence Alignment of B-Family DNA Polymerases

FIG. 1 shows the amino acid sequence alignment of 16 wild-type B-family DNA polymerases (PolBs) utilized by the inventor, and the outcome of aligned consensus sequence is listed in the bottom (SEQ ID NO:1). The 16 wild-type PolBs being aligned are *Thermococcus gorgonarius* DNA polymerase (Tgo, SEQ ID NO:2), *Thermococcus kodakarensis* DNA polymerase (Kod1, SEQ ID NO:3), *Thermococcus* sp. (strain 9°N-7) DNA polymerase (9°N, SEQ ID NO:4), *Pyrococcus furiosus* DNA polymerase (Pfu, SEQ ID NO:5), *Thermococcus litoralis* DNA polymerase (Vent, SEQ ID NO:6), *Methanosarcina acetivorans* DNA polymerase (Mac, SEQ ID NO:7), *Pyrobaculum islandicum* DNA polymerase, (Pis, SEQ ID NO:8), *Sulfolobus solfataricus* DNA polymerase (Sso, SEQ ID NO:9), *Methanococcus maripaludis* DNA polymerase (Mma, SEQ ID NO:10), human DNA polymerase delta catalytic p125 subunit (hPOLD, SEQ ID NO:11), *Saccharomyces cerevisiae* DNA polymerase delta catalytic subunit (ScePOLD, SEQ ID NO:12), *Pseudomonas aeruginosa* DNA polymerase II (Pae, SEQ ID NO:13), *Escherichia coli* DNA polymerase II (Eco, SEQ ID NO:14), *Escherichia* phage RB69 DNA polymerase (RB69, SEQ ID NO:15), *Escherichia* phage T4 DNA polymerase (T4, SEQ ID NO:16), and *Bacillus* phage Phi29 DNA polymerase (Phi29, SEQ ID NO:17).

As shown in FIG. 1, various sequence regions among these exemplary wild-type PolBs are highly conserved while other regions are more variable. Those of skill in the art will immediately recognize and understand that mutations in addition to those specifically identified and discussed herein may be also made in the variable regions of wild-type PolBs without altering, or without substantially altering, the polymerase activity of the mutated enzyme. Likewise, conservative mutations at conserved residues/positions of any of PolBs may be made without altering, or substantially altering, the polymerase activity of the mutated enzyme. Enzyme engineering based on comparative structure analysis with other functionally related enzymes or homologs is a useful technique in the molecular biology field that allows the inventor reasonably predict the effect of a given mutation on the catalytic activity of the enzyme. Based on the present disclosure, using the sequence, the structural data and known physical properties of amino acids, those of skill in the art can mutate enzymes, such as the DNA polymerases encompassed by the present invention, without altering, or without substantially altering, the essential, intrinsic characteristics of the enzymes.

Besides, the motifs Exo I, Exo II, Exo III, A, B, and C corresponding to the positions 349 to 364, 450 to 476, 590 to 608, 706 to 730, 843 to 855, and 940 to 956 respectively of the consensus sequence of SEQ ID NO:1 are focused in the present disclosure. More specifically, the polymerase variant in the present invention is based on substitution mutations at one or more residues correspondingly residing in said motifs.

B-Family DNA Polymerase Variant

In view of the above, provided herein are altered polymerase, which is described based on the amino acid sequence of the consensus sequence of SEQ ID NO: 1. An altered polymerase includes substitution mutations at one or more residues when compared to the consensus sequence of SEQ ID NO: 1. A substitution mutation can be at the same, or homologous, position or a functionally equivalent position compared to the consensus sequence of SEQ ID NO: 1. The skilled person can readily appreciate that an altered polymerase described herein is not naturally occurring. Therefore, an altered polymerase described herein is based on the consensus sequence of SEQ ID NO: 1 and further includes substitution mutations at one or more residues of the corresponding wild-type polymerase (parent polymerase). In one embodiment, at least one substitution mutation is at a position functionally equivalent to an amino acid of the consensus sequence of SEQ ID NO: 1. "Functionally equivalent" means that the altered polymerase has the amino acid substitution at the amino acid position according to the consensus sequence of SEQ ID NO: 1 that has the same functional or structural role in both the consensus sequence and the altered polymerase.

In general, functionally equivalent substitution mutations in two or more different polymerases occur at homologous amino acid positions in the amino acid sequences of the polymerases. Hence, "functionally equivalent" also encompasses mutations that are "positionally equivalent" or "homologous" to a given mutation, regardless of whether or not the particular function of the mutated amino acid is known. It is possible to identify the regions of functionally equivalent and positionally equivalent amino acid residues in the amino acid sequences of two or more different polymerases on the basis of sequence alignment and/or molecular modeling. For instance, the amino acid sequence alignment of exemplary 16 wild-type B-family DNA polymerases from different domains of life are used to identify positionally equivalent and/or functionally equivalent residues. The result of the protein sequence alignment among these PolBs is set forth in FIG. 1. Thus, for the exemplary residue 141 of the Tgo, Kod1, 9°N, Pfu, and Vent polymerases, residue 171 of the Pis, residue 231 of the Sso, and residue 198 of the Mac polymerase are functionally equivalent and positionally equivalent. Likewise, for the exemplary residue 143 of the Tgo, Kod1, 9°N, Pfu, and Vent polymerases residue 173 of the Pis, residue 233 of the Sso, and residue 200 of the Mac polymerase are functionally equivalent and positionally equivalent. The skilled person can easily identify functionally equivalent residues in DNA polymerases.

In accordance with some embodiments, the provided B-family DNA polymerase variant comprising: a motif Exo I, a motif Exo II, a motif Exo III, a motif A, a motif B, and a motif C corresponding, respectively, to the positions 349 to 364, 450 to 476, 590 to 608, 706 to 730, 843 to 855, and 940 to 956 of the consensus sequence of SEQ ID NO:1; at least one amino acid substitution (one or more amino acid substitutions, or a combination of amino acid substitutions) at positions residing in the motif Exo I, the motif Exo II, and the motif Exo III; and at least one amino acid substitution (one or more amino acid substitutions, or a combination of amino acid substitutions), at positions residing in the motif A, the motif B, and the motif C.

In accordance with the object of the invention to provide a PolB variant having the amino acid sequence as set forth in SEQ ID NO: 1 and the functionally or positionally equivalent sequences, with any substitution or combination of amino acid substitutions listed in Table 1, where the "Essential substitutions" include the substitution motifs, by itself, to confer the activity of de novo nucleic acid synthesis to said PolB variant; and the "Reinforceable substitutions" include the substitution residues that may also confer said activity by itself with a minor capability. Thus, preferably, the "Essential substitutions" can be used alone or in combination with any other mutations, and the "Reinforceable substitutions" are optionally used in combination with the "Essential substitutions" or any other mutations.

TABLE 1

List of PolB variants having the amino acid substitutions according to SEQ ID NO: 1.

| Name | Essential substitutions | Reinforceable substitutions |
| --- | --- | --- |
| YD001 | L715A + Y716A + P717A | A854C/A854D/A854E/A854F/A854H/A854G/A854L/A854R/A854T/A854K/A854Y |
| YD002 | L715F + Y716A + P717A | A854C/A854D/A854E/A854F/A854H/A854G/A854L/A854R/A854T/A854K/A854Y |
| YD003 | L715H + Y716A + P717A | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD004 | L715I + Y716A + P717A | A854C/A854D/A854E/A854F/A854H/A854G/A854L/A854R/A854T/A854K/A854Y |
| YD005 | L715Q + Y716A + P717A | A854C/A854D/A854E/A854F/A854H/A854G/A854L/A854R/A854T/A854K/A854Y |
| YD006 | L715S + Y716A + P717A | A854C/A854D/A854E/A854F/A854H/A854G/A854L/A854R/A854T/A854K/A854Y |
| YD007 | L715W + Y716A + P717A | A854C/A854D/A854E/A854F/A854H/A854G/A854L/A854R/A854T/A854K/A854Y |
| YD008 | L715Y + Y716A + P717A | A854C/A854D/A854E/A854F/A854H/A854G/A854L/A854R/A854T/A854K/A854Y |
| YD009 | L715A + Y716C + P717A | A854C/A854D/A854E/A854F/A854H/A854G/A854L/A854R/A854T/A854K/A854Y |
| YD010 | L715F + Y716C + P717A | A854C/A854D/A854E/A854F/A854H/A854G/A854L/A854R/A854T/A854K/A854Y |
| YD011 | L715H + Y716C + P717A | A854C/A854D/A854E/A854F/A854H/A854G/A854L/A854R/A854T/A854K/A854Y |
| YD012 | L715I + Y716C + P717A | A854C/A854D/A854E/A854F/A854H/A854G/A854L/A854R/A854T/A854K/A854Y |
| YD013 | L715Q + Y716C + P717A | A854C/A854D/A854E/A854F/A854H/A854G/A854L/A854R/A854T/A854K/A854Y |
| YD014 | L715S + Y716C + P717A | A854C/A854D/A854E/A854F/A854H/A854G/A854L/A854R/A854T/A854K/A854Y |
| YD015 | L715W + Y716C + P717A | A854C/A854D/A854E/A854F/A854H/A854G/A854L/A854R/A854T/A854K/A854Y |
| YD016 | L715Y + Y716C + P717A | A854C/A854D/A854E/A854F/A854H/A854G/A854L/A854R/A854T/A854K/A854Y |
| YD017 | L715A + Y716D + P717A | A854C/A854D/A854E/A854F/A854H/A854G/A854L/A854R/A854T/A854K/A854Y |
| YD018 | L715F + Y716D + P717A | A854C/A854D/A854E/A854F/A854H/A854G/A854L/A854R/A854T/A854K/A854Y |
| YD019 | L715H + Y716D + P717A | A854C/A854D/A854E/A854F/A854H/A854G/A854L/A854R/A854T/A854K/A854Y |
| YD020 | L715I + Y716D + P717A | A854C/A854D/A854E/A854F/A854H/A854G/A854L/A854R/A854T/A854K/A854Y |
| YD021 | L715Q + Y716D + P717A | A854C/A854D/A854E/A854F/A854H/A854G/A854L/A854R/A854T/A854K/A854Y |
| YD022 | L715S + Y716D + P717A | A854C/A854D/A854E/A854F/A854H/A854G/A854L/A854R/A854T/A854K/A854Y |
| YD023 | L715W + Y716D + P717A | A854C/A854D/A854E/A854F/A854H/A854G/A854L/A854R/A854T/A854K/A854Y |
| YD024 | L715Y + Y716D + P717A | A854C/A854D/A854E/A854F/A854H/A854G/A854L/A854R/A854T/A854K/A854Y |
| YD025 | L715A + Y716F + P717A | A854C/A854D/A854E/A854F/A854H/A854G/A854L/A854R/A854T/A854K/A854Y |
| YD026 | L715F + Y716F + P717A | A854C/A854D/A854E/A854F/A854H/A854G/A854L/A854R/A854T/A854K/A854Y |
| YD027 | L715H + Y716F + P717A | A854C/A854D/A854E/A854F/A854H/A854G/A854L/A854R/A854T/A854K/A854Y |
| YD028 | L715I + Y716F + P717A | A854C/A854D/A854E/A854F/A854H/A854G/A854L/A854R/A854T/A854K/A854Y |
| YD029 | L715Q + Y716F + P717A | A854C/A854D/A854E/A854F/A854H/A854G/A854L/A854R/A854T/A854K/A854Y |
| YD030 | L715S + Y716F + P717A | A854C/A854D/A854E/A854F/A854H/A854G/A854L/A854R/A854T/A854K/A854Y |
| YD031 | L715W + Y716F + P717A | A854C/A854D/A854E/A854F/A854H/A854G/A854L/A854R/A854T/A854K/A854Y |
| YD032 | L715Y + Y716F + P717A | A854C/A854D/A854E/A854F/A854H/A854G/A854L/A854R/A854T/A854K/A854Y |
| YD033 | L715A + Y716G + P717A | A854C/A854D/A854E/A854F/A854H/A854G/A854L/A854R/A854T/A854K/A854Y |
| YD034 | L715F + Y716G + P717A | A854C/A854D/A854E/A854F/A854H/A854G/A854L/A854R/A854T/A854K/A854Y |
| YD035 | L715H + Y716G + P717A | A854C/A854D/A854E/A854F/A854H/A854G/A854L/A854R/A854T/A854K/A854Y |
| YD036 | L715I + Y716G + P717A | A854C/A854D/A854E/A854F/A854H/A854G/A854L/A854R/A854T/A854K/A854Y |
| YD037 | L715Q + Y716G + P717A | A854C/A854D/A854E/A854F/A854H/A854G/A854L/A854R/A854T/A854K/A854Y |
| YD038 | L715S + Y716G + P717A | A854C/A854D/A854E/A854F/A854H/A854G/A854L/A854R/A854T/A854K/A854Y |
| YD039 | L715W + Y716G + P717A | A854C/A854D/A854E/A854F/A854H/A854G/A854L/A854R/A854T/A854K/A854Y |
| YD040 | L715Y + Y716G + P717A | A854C/A854D/A854E/A854F/A854H/A854G/A854L/A854R/A854T/A854K/A854Y |
| YD041 | L715A + Y716H + P717A | A854C/A854D/A854E/A854F/A854H/A854G/A854L/A854R/A854T/A854K/A854Y |
| YD042 | L715F + Y716H + P717A | A854C/A854D/A854E/A854F/A854H/A854G/A854L/A854R/A854T/A854K/A854Y |
| YD043 | L715H + Y716H + P717A | A854C/A854D/A854E/A854F/A854H/A854G/A854L/A854R/A854T/A854K/A854Y |
| YD044 | L715I + Y716H + P717A | A854C/A854D/A854E/A854F/A854H/A854G/A854L/A854R/A854T/A854K/A854Y |
| YD045 | L715Q + Y716H + P717A | A854C/A854D/A854E/A854F/A854H/A854G/A854L/A854R/A854T/A854K/A854Y |
| YD046 | L715S + Y716H + P717A | A854C/A854D/A854E/A854F/A854H/A854G/A854L/A854R/A854T/A854K/A854Y |
| YD047 | L715W + Y716H + P717A | A854C/A854D/A854E/A854F/A854H/A854G/A854L/A854R/A854T/A854K/A854Y |
| YD048 | L715Y + Y716H + P717A | A854C/A854D/A854E/A854F/A854H/A854G/A854L/A854R/A854T/A854K/A854Y |
| YD049 | L715A + Y716I + P717A | A854C/A854D/A854E/A854F/A854H/A854G/A854L/A854R/A854T/A854K/A854Y |
| YD050 | L715F + Y716I + P717A | A854C/A854D/A854E/A854F/A854H/A854G/A854L/A854R/A854T/A854K/A854Y |
| YD051 | L715H + Y716I + P717A | A854C/A854D/A854E/A854F/A854H/A854G/A854L/A854R/A854T/A854K/A854Y |
| YD052 | L715I + Y716I + P717A | A854C/A854D/A854E/A854F/A854H/A854G/A854L/A854R/A854T/A854K/A854Y |
| YD053 | L715Q + Y716I + P717A | A854C/A854D/A854E/A854F/A854H/A854G/A854L/A854R/A854T/A854K/A854Y |
| YD054 | L715S + Y716I + P717A | A854C/A854D/A854E/A854F/A854H/A854G/A854L/A854R/A854T/A854K/A854Y |
| YD055 | L715W + Y716I + P717A | A854C/A854D/A854E/A854F/A854H/A854G/A854L/A854R/A854T/A854K/A854Y |
| YD056 | L715Y + Y716I + P717A | A854C/A854D/A854E/A854F/A854H/A854G/A854L/A854R/A854T/A854K/A854Y |
| YD057 | L715A + Y716K + P717A | A854C/A854D/A854E/A854F/A854H/A854G/A854L/A854R/A854T/A854K/A854Y |
| YD058 | L715F + Y716K + P717A | A854C/A854D/A854E/A854F/A854H/A854G/A854L/A854R/A854T/A854K/A854Y |
| YD059 | L715H + Y716K + P717A | A854C/A854D/A854E/A854F/A854H/A854G/A854L/A854R/A854T/A854K/A854Y |
| YD060 | L715I + Y716K + P717A | A854C/A854D/A854E/A854F/A854H/A854G/A854L/A854R/A854T/A854K/A854Y |
| YD061 | L715Q + Y716K + P717A | A854C/A854D/A854E/A854F/A854H/A854G/A854L/A854R/A854T/A854K/A854Y |
| YD062 | L715S + Y716K + P717A | A854C/A854D/A854E/A854F/A854H/A854G/A854L/A854R/A854T/A854K/A854Y |
| YD063 | L715W + Y716K + P717A | A854C/A854D/A854E/A854F/A854H/A854G/A854L/A854R/A854T/A854K/A854Y |
| YD064 | L715Y + Y716K + P717A | A854C/A854D/A854E/A854F/A854H/A854G/A854L/A854R/A854T/A854K/A854Y |
| YD065 | L715A + Y716L + P717A | A854C/A854D/A854E/A854F/A854H/A854G/A854L/A854R/A854T/A854K/A854Y |
| YD066 | L715F + Y716L + P717A | A854C/A854D/A854E/A854F/A854H/A854G/A854L/A854R/A854T/A854K/A854Y |
| YD067 | L715H + Y716L + P717A | A854C/A854D/A854E/A854F/A854H/A854G/A854L/A854R/A854T/A854K/A854Y |
| YD068 | L715I + Y716L + P717A | A854C/A854D/A854E/A854F/A854H/A854G/A854L/A854R/A854T/A854K/A854Y |
| YD069 | L715Q + Y716L + P717A | A854C/A854D/A854E/A854F/A854H/A854G/A854L/A854R/A854T/A854K/A854Y |
| YD070 | L715S + Y716L + P717A | A854C/A854D/A854E/A854F/A854H/A854G/A854L/A854R/A854T/A854K/A854Y |
| YD071 | L715W + Y716L + P717A | A854C/A854D/A854E/A854F/A854H/A854G/A854L/A854R/A854T/A854K/A854Y |
| YD072 | L715Y + Y716L + P717A | A854C/A854D/A854E/A854F/A854H/A854G/A854L/A854R/A854T/A854K/A854Y |
| YD073 | L715A + Y716M + P717A | A854C/A854D/A854E/A854F/A854H/A854G/A854L/A854R/A854T/A854K/A854Y |
| YD074 | L715F + Y716M + P717A | A854C/A854D/A854E/A854F/A854H/A854G/A854L/A854R/A854T/A854K/A854Y |
| YD075 | L715H + Y716M + P717A | A854C/A854D/A854E/A854F/A854H/A854G/A854L/A854R/A854T/A854K/A854Y |
| YD076 | L715I + Y716M + P717A | A854C/A854D/A854E/A854F/A854H/A854G/A854L/A854R/A854T/A854K/A854Y |
| YD077 | L715Q + Y716M + P717A | A854C/A854D/A854E/A854F/A854H/A854G/A854L/A854R/A854T/A854K/A854Y |
| YD078 | L715S + Y716M + P717A | A854C/A854D/A854E/A854F/A854H/A854G/A854L/A854R/A854T/A854K/A854Y |
| YD079 | L715W + Y716M + P717A | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD080 | L715Y + Y716M + P717A | A854C/A854D/A854E/A854F/A854H/A854G/A854L/A854R/A854T/A854K/A854Y |
| YD081 | L715A + Y716N + P717A | A854C/A854D/A854E/A854F/A854H/A854G/A854L/A854R/A854T/A854K/A854Y |
| YD082 | L715F + Y716N + P717A | A854C/A854D/A854E/A854F/A854H/A854G/A854L/A854R/A854T/A854K/A854Y |
| YD083 | L715H + Y716N + P717A | A854C/A854D/A854E/A854F/A854H/A854G/A854L/A854R/A854T/A854K/A854Y |
| YD084 | L715I + Y716N + P717A | A854C/A854D/A854E/A854F/A854H/A854G/A854L/A854R/A854T/A854K/A854Y |
| YD085 | L715Q + Y716N + P717A | A854C/A854D/A854E/A854F/A854H/A854G/A854L/A854R/A854T/A854K/A854Y |
| YD086 | L715S + Y716N + P717A | A854C/A854D/A854E/A854F/A854H/A854G/A854L/A854R/A854T/A854K/A854Y |
| YD087 | L715W + Y716N + P717A | A854C/A854D/A854E/A854F/A854H/A854G/A854L/A854R/A854T/A854K/A854Y |
| YD088 | L715Y + Y716N + P717A | A854C/A854D/A854E/A854F/A854H/A854G/A854L/A854R/A854T/A854K/A854Y |
| YD089 | L715A + Y716Q + P717A | A854C/A854D/A854E/A854F/A854H/A854G/A854L/A854R/A854T/A854K/A854Y |
| YD090 | L715F + Y716Q + P717A | A854C/A854D/A854E/A854F/A854H/A854G/A854L/A854R/A854T/A854K/A854Y |
| YD091 | L715H + Y716Q + P717A | A854C/A854D/A854E/A854F/A854H/A854G/A854L/A854R/A854T/A854K/A854Y |
| YD092 | L715I + Y716Q + P717A | A854C/A854D/A854E/A854F/A854H/A854G/A854L/A854R/A854T/A854K/A854Y |
| YD093 | L715Q + Y716Q + P717A | A854C/A854D/A854E/A854F/A854H/A854G/A854L/A854R/A854T/A854K/A854Y |
| YD094 | L715S + Y716Q + P717A | A854C/A854D/A854E/A854F/A854H/A854G/A854L/A854R/A854T/A854K/A854Y |
| YD095 | L715W + Y716Q + P717A | A854C/A854D/A854E/A854F/A854H/A854G/A854L/A854R/A854T/A854K/A854Y |
| YD096 | L715Y + Y716Q + P717A | A854C/A854D/A854E/A854F/A854H/A854G/A854L/A854R/A854T/A854K/A854Y |
| YD097 | L715A + Y716A + P717G | A854C/A854D/A854E/A854F/A854H/A854G/A854L/A854R/A854T/A854K/A854Y |
| YD098 | L715F + Y716A + P717G | A854C/A854D/A854E/A854F/A854H/A854G/A854L/A854R/A854T/A854K/A854Y |
| YD099 | L715H + Y716A + P717G | A854C/A854D/A854E/A854F/A854H/A854G/A854L/A854R/A854T/A854K/A854Y |
| YD100 | L715I + Y716A + P717G | A854C/A854D/A854E/A854F/A854H/A854G/A854L/A854R/A854T/A854K/A854Y |
| YD101 | L715Q + Y716A + P717G | A854C/A854D/A854E/A854F/A854H/A854G/A854L/A854R/A854T/A854K/A854Y |
| YD102 | L715S + Y716A + P717G | A854C/A854D/A854E/A854F/A854H/A854G/A854L/A854R/A854T/A854K/A854Y |
| YD103 | L715W + Y716A + P717G | A854C/A854D/A854E/A854F/A854H/A854G/A854L/A854R/A854T/A854K/A854Y |
| YD104 | L715Y + Y716A + P717G | A854C/A854D/A854E/A854F/A854H/A854G/A854L/A854R/A854T/A854K/A854Y |
| YD105 | L715A + Y716C + P717G | A854C/A854D/A854E/A854F/A854H/A854G/A854L/A854R/A854T/A854K/A854Y |
| YD106 | L715F + Y716C + P717G | A854C/A854D/A854E/A854F/A854H/A854G/A854L/A854R/A854T/A854K/A854Y |
| YD107 | L715H + Y716C + P717G | A854C/A854D/A854E/A854F/A854H/A854G/A854L/A854R/A854T/A854K/A854Y |
| YD108 | L715I + Y716C + P717G | A854C/A854D/A854E/A854F/A854H/A854G/A854L/A854R/A854T/A854K/A854Y |
| YD109 | L715Q + Y716C + P717G | A854C/A854D/A854E/A854F/A854H/A854G/A854L/A854R/A854T/A854K/A854Y |
| YD110 | L715S + Y716C + P717G | A854C/A854D/A854E/A854F/A854H/A854G/A854L/A854R/A854T/A854K/A854Y |
| YD111 | L715W + Y716C + P717G | A854C/A854D/A854E/A854F/A854H/A854G/A854L/A854R/A854T/A854K/A854Y |
| YD112 | L715Y + Y716C + P717G | A854C/A854D/A854E/A854F/A854H/A854G/A854L/A854R/A854T/A854K/A854Y |
| YD113 | L715A + Y716D + P717G | A854C/A854D/A854E/A854F/A854H/A854G/A854L/A854R/A854T/A854K/A854Y |
| YD114 | L715F + Y716D + P717G | A854C/A854D/A854E/A854F/A854H/A854G/A854L/A854R/A854T/A854K/A854Y |
| YD115 | L715H + Y716D + P717G | A854C/A854D/A854E/A854F/A854H/A854G/A854L/A854R/A854T/A854K/A854Y |
| YD116 | L715I + Y716D + P717G | A854C/A854D/A854E/A854F/A854H/A854G/A854L/A854R/A854T/A854K/A854Y |
| YD117 | L715Q + Y716D + P717G | A854C/A854D/A854E/A854F/A854H/A854G/A854L/A854R/A854T/A854K/A854Y |
| YD118 | L715S + Y716D + P717G | A854C/A854D/A854E/A854F/A854H/A854G/A854L/A854R/A854T/A854K/A854Y |
| YD119 | L715W + Y716D + P717G | A854C/A854D/A854E/A854F/A854H/A854G/A854L/A854R/A854T/A854K/A854Y |
| YD120 | L715Y + Y716D + P717G | A854C/A854D/A854E/A854F/A854H/A854G/A854L/A854R/A854T/A854K/A854Y |
| YD121 | L715A + Y716F + P717G | A854C/A854D/A854E/A854F/A854H/A854G/A854L/A854R/A854T/A854K/A854Y |
| YD122 | L715F + Y716F + P717G | A854C/A854D/A854E/A854F/A854H/A854G/A854L/A854R/A854T/A854K/A854Y |
| YD123 | L715H + Y716F + P717G | A854C/A854D/A854E/A854F/A854H/A854G/A854L/A854R/A854T/A854K/A854Y |
| YD124 | L715I + Y716F + P717G | A854C/A854D/A854E/A854F/A854H/A854G/A854L/A854R/A854T/A854K/A854Y |
| YD125 | L715Q + Y716F + P717G | A854C/A854D/A854E/A854F/A854H/A854G/A854L/A854R/A854T/A854K/A854Y |
| YD126 | L715S + Y716F + P717G | A854C/A854D/A854E/A854F/A854H/A854G/A854L/A854R/A854T/A854K/A854Y |
| YD127 | L715W + Y716F + P717G | A854C/A854D/A854E/A854F/A854H/A854G/A854L/A854R/A854T/A854K/A854Y |
| YD128 | L715Y + Y716F + P717G | A854C/A854D/A854E/A854F/A854H/A854G/A854L/A854R/A854T/A854K/A854Y |
| YD129 | L715A + Y716G + P717G | A854C/A854D/A854E/A854F/A854H/A854G/A854L/A854R/A854T/A854K/A854Y |
| YD130 | L715F + Y716G + P717G | A854C/A854D/A854E/A854F/A854H/A854G/A854L/A854R/A854T/A854K/A854Y |
| YD131 | L715H + Y716G + P717G | A854C/A854D/A854E/A854F/A854H/A854G/A854L/A854R/A854T/A854K/A854Y |
| YD132 | L715I + Y716G + P717G | A854C/A854D/A854E/A854F/A854H/A854G/A854L/A854R/A854T/A854K/A854Y |
| YD133 | L715Q + Y716G + P717G | A854C/A854D/A854E/A854F/A854H/A854G/A854L/A854R/A854T/A854K/A854Y |
| YD134 | L715S + Y716G + P717G | A854C/A854D/A854E/A854F/A854H/A854G/A854L/A854R/A854T/A854K/A854Y |
| YD135 | L715W + Y716G + P717G | A854C/A854D/A854E/A854F/A854H/A854G/A854L/A854R/A854T/A854K/A854Y |
| YD136 | L715Y + Y716G + P717G | A854C/A854D/A854E/A854F/A854H/A854G/A854L/A854R/A854T/A854K/A854Y |
| YD137 | L715A + Y716H + P717G | A854C/A854D/A854E/A854F/A854H/A854G/A854L/A854R/A854T/A854K/A854Y |
| YD138 | L715F + Y716H + P717G | A854C/A854D/A854E/A854F/A854H/A854G/A854L/A854R/A854T/A854K/A854Y |
| YD139 | L715H + Y716H + P717G | A854C/A854D/A854E/A854F/A854H/A854G/A854L/A854R/A854T/A854K/A854Y |
| YD140 | L715I + Y716H + P717G | A854C/A854D/A854E/A854F/A854H/A854G/A854L/A854R/A854T/A854K/A854Y |
| YD141 | L715Q + Y716H + P717G | A854C/A854D/A854E/A854F/A854H/A854G/A854L/A854R/A854T/A854K/A854Y |
| YD142 | L715S + Y716H + P717G | A854C/A854D/A854E/A854F/A854H/A854G/A854L/A854R/A854T/A854K/A854Y |
| YD143 | L715W + Y716H + P717G | A854C/A854D/A854E/A854F/A854H/A854G/A854L/A854R/A854T/A854K/A854Y |
| YD144 | L715Y + Y716H + P717G | A854C/A854D/A854E/A854F/A854H/A854G/A854L/A854R/A854T/A854K/A854Y |
| YD145 | L715A + Y716I + P717G | A854C/A854D/A854E/A854F/A854H/A854G/A854L/A854R/A854T/A854K/A854Y |
| YD146 | L715F + Y716I + P717G | A854C/A854D/A854E/A854F/A854H/A854G/A854L/A854R/A854T/A854K/A854Y |
| YD147 | L715H + Y716I + P717G | A854C/A854D/A854E/A854F/A854H/A854G/A854L/A854R/A854T/A854K/A854Y |
| YD148 | L715I + Y716I + P717G | A854C/A854D/A854E/A854F/A854H/A854G/A854L/A854R/A854T/A854K/A854Y |
| YD149 | L715Q + Y716I + P717G | A854C/A854D/A854E/A854F/A854H/A854G/A854L/A854R/A854T/A854K/A854Y |
| YD150 | L715S + Y716I + P717G | A854C/A854D/A854E/A854F/A854H/A854G/A854L/A854R/A854T/A854K/A854Y |
| YD151 | L715W + Y716I + P717G | A854C/A854D/A854E/A854F/A854H/A854G/A854L/A854R/A854T/A854K/A854Y |
| YD152 | L715Y + Y716I + P717G | A854C/A854D/A854E/A854F/A854H/A854G/A854L/A854R/A854T/A854K/A854Y |
| YD153 | L715A + Y716K + P717G | A854C/A854D/A854E/A854F/A854H/A854G/A854L/A854R/A854T/A854K/A854Y |
| YD154 | L715F + Y716K + P717G | A854C/A854D/A854E/A854F/A854H/A854G/A854L/A854R/A854T/A854K/A854Y |
| YD155 | L715H + Y716K + P717G | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD156 | L715I + Y716K + P717G | A854C/A854D/A854E/A854F/A854H/A854G/A854L/A854R/A854T/A854K/A854Y |
| YD157 | L715Q + Y716K + P717G | A854C/A854D/A854E/A854F/A854H/A854G/A854L/A854R/A854T/A854K/A854Y |
| YD158 | L715S + Y716K + P717G | A854C/A854D/A854E/A854F/A854H/A854G/A854L/A854R/A854T/A854K/A854Y |
| YD159 | L715W + Y716K + P717G | A854C/A854D/A854E/A854F/A854H/A854G/A854L/A854R/A854T/A854K/A854Y |
| YD160 | L715Y + Y716K + P717G | A854C/A854D/A854E/A854F/A854H/A854G/A854L/A854R/A854T/A854K/A854Y |
| YD161 | L715A + Y716L + P717G | A854C/A854D/A854E/A854F/A854H/A854G/A854L/A854R/A854T/A854K/A854Y |
| YD162 | L715F + Y716L + P717G | A854C/A854D/A854E/A854F/A854H/A854G/A854L/A854R/A854T/A854K/A854Y |
| YD163 | L715H + Y716L + P717G | A854C/A854D/A854E/A854F/A854H/A854G/A854L/A854R/A854T/A854K/A854Y |
| YD164 | L715I + Y716L + P717G | A854C/A854D/A854E/A854F/A854H/A854G/A854L/A854R/A854T/A854K/A854Y |
| YD165 | L715Q + Y716L + P717G | A854C/A854D/A854E/A854F/A854H/A854G/A854L/A854R/A854T/A854K/A854Y |
| YD166 | L715S + Y716L + P717G | A854C/A854D/A854E/A854F/A854H/A854G/A854L/A854R/A854T/A854K/A854Y |
| YD167 | L715W + Y716L + P717G | A854C/A854D/A854E/A854F/A854H/A854G/A854L/A854R/A854T/A854K/A854Y |
| YD168 | L715Y + Y716L + P717G | A854C/A854D/A854E/A854F/A854H/A854G/A854L/A854R/A854T/A854K/A854Y |
| YD169 | L715A + Y716M + P717G | A854C/A854D/A854E/A854F/A854H/A854G/A854L/A854R/A854T/A854K/A854Y |
| YD170 | L715F + Y716M + P717G | A854C/A854D/A854E/A854F/A854H/A854G/A854L/A854R/A854T/A854K/A854Y |
| YD171 | L715H + Y716M + P717G | A854C/A854D/A854E/A854F/A854H/A854G/A854L/A854R/A854T/A854K/A854Y |
| YD172 | L715I + Y716M + P717G | A854C/A854D/A854E/A854F/A854H/A854G/A854L/A854R/A854T/A854K/A854Y |
| YD173 | L715Q + Y716M + P717G | A854C/A854D/A854E/A854F/A854H/A854G/A854L/A854R/A854T/A854K/A854Y |
| YD174 | L715S + Y716M + P717G | A854C/A854D/A854E/A854F/A854H/A854G/A854L/A854R/A854T/A854K/A854Y |
| YD175 | L715W + Y716M + P717G | A854C/A854D/A854E/A854F/A854H/A854G/A854L/A854R/A854T/A854K/A854Y |
| YD176 | L715Y + Y716M + P717G | A854C/A854D/A854E/A854F/A854H/A854G/A854L/A854R/A854T/A854K/A854Y |
| YD177 | L715A + Y716N + P717G | A854C/A854D/A854E/A854F/A854H/A854G/A854L/A854R/A854T/A854K/A854Y |
| YD178 | L715F + Y716N + P717G | A854C/A854D/A854E/A854F/A854H/A854G/A854L/A854R/A854T/A854K/A854Y |
| YD179 | L715H + Y716N + P717G | A854C/A854D/A854E/A854F/A854H/A854G/A854L/A854R/A854T/A854K/A854Y |
| YD180 | L715I + Y716N + P717G | A854C/A854D/A854E/A854F/A854H/A854G/A854L/A854R/A854T/A854K/A854Y |
| YD181 | L715Q + Y716N + P717G | A854C/A854D/A854E/A854F/A854H/A854G/A854L/A854R/A854T/A854K/A854Y |
| YD182 | L715S + Y716N + P717G | A854C/A854D/A854E/A854F/A854H/A854G/A854L/A854R/A854T/A854K/A854Y |
| YD183 | L715W + Y716N + P717G | A854C/A854D/A854E/A854F/A854H/A854G/A854L/A854R/A854T/A854K/A854Y |
| YD184 | L715Y + Y716N + P717G | A854C/A854D/A854E/A854F/A854H/A854G/A854L/A854R/A854T/A854K/A854Y |
| YD185 | L715A + Y716Q + P717G | A854C/A854D/A854E/A854F/A854H/A854G/A854L/A854R/A854T/A854K/A854Y |
| YD186 | L715F + Y716Q + P717G | A854C/A854D/A854E/A854F/A854H/A854G/A854L/A854R/A854T/A854K/A854Y |
| YD187 | L715H + Y716Q + P717G | A854C/A854D/A854E/A854F/A854H/A854G/A854L/A854R/A854T/A854K/A854Y |
| YD188 | L715I + Y716Q + P717G | A854C/A854D/A854E/A854F/A854H/A854G/A854L/A854R/A854T/A854K/A854Y |
| YD189 | L715Q + Y716Q + P717G | A854C/A854D/A854E/A854F/A854H/A854G/A854L/A854R/A854T/A854K/A854Y |
| YD190 | L715S + Y716Q + P717G | A854C/A854D/A854E/A854F/A854H/A854G/A854L/A854R/A854T/A854K/A854Y |
| YD191 | L715W + Y716Q + P717G | A854C/A854D/A854E/A854F/A854H/A854G/A854L/A854R/A854T/A854K/A854Y |
| YD192 | L715Y + Y716Q + P717G | A854C/A854D/A854E/A854F/A854H/A854G/A854L/A854R/A854T/A854K/A854Y |
| YD193 | L715A + Y716A + P717S | A854C/A854D/A854E/A854F/A854H/A854G/A854L/A854R/A854T/A854K/A854Y |
| YD194 | L715F + Y716A + P717S | A854C/A854D/A854E/A854F/A854H/A854G/A854L/A854R/A854T/A854K/A854Y |
| YD195 | L715H + Y716A + P717S | A854C/A854D/A854E/A854F/A854H/A854G/A854L/A854R/A854T/A854K/A854Y |
| YD196 | L715I + Y716A + P717S | A854C/A854D/A854E/A854F/A854H/A854G/A854L/A854R/A854T/A854K/A854Y |
| YD197 | L715Q + Y716A + P717S | A854C/A854D/A854E/A854F/A854H/A854G/A854L/A854R/A854T/A854K/A854Y |
| YD198 | L715S + Y716A + P717S | A854C/A854D/A854E/A854F/A854H/A854G/A854L/A854R/A854T/A854K/A854Y |
| YD199 | L715W + Y716A + P717S | A854C/A854D/A854E/A854F/A854H/A854G/A854L/A854R/A854T/A854K/A854Y |
| YD200 | L715Y + Y716A + P717S | A854C/A854D/A854E/A854F/A854H/A854G/A854L/A854R/A854T/A854K/A854Y |
| YD201 | L715A + Y716C + P717S | A854C/A854D/A854E/A854F/A854H/A854G/A854L/A854R/A854T/A854K/A854Y |
| YD202 | L715F + Y716C + P717S | A854C/A854D/A854E/A854F/A854H/A854G/A854L/A854R/A854T/A854K/A854Y |
| YD203 | L715H + Y716C + P717S | A854C/A854D/A854E/A854F/A854H/A854G/A854L/A854R/A854T/A854K/A854Y |
| YD204 | L715I + Y716C + P717S | A854C/A854D/A854E/A854F/A854H/A854G/A854L/A854R/A854T/A854K/A854Y |
| YD205 | L715Q + Y716C + P717S | A854C/A854D/A854E/A854F/A854H/A854G/A854L/A854R/A854T/A854K/A854Y |
| YD206 | L715S + Y716C + P717S | A854C/A854D/A854E/A854F/A854H/A854G/A854L/A854R/A854T/A854K/A854Y |
| YD207 | L715W + Y716C + P717S | A854C/A854D/A854E/A854F/A854H/A854G/A854L/A854R/A854T/A854K/A854Y |
| YD208 | L715Y + Y716C + P717S | A854C/A854D/A854E/A854F/A854H/A854G/A854L/A854R/A854T/A854K/A854Y |
| YD209 | L715A + Y716D + P717S | A854C/A854D/A854E/A854F/A854H/A854G/A854L/A854R/A854T/A854K/A854Y |
| YD210 | L715F + Y716D + P717S | A854C/A854D/A854E/A854F/A854H/A854G/A854L/A854R/A854T/A854K/A854Y |
| YD211 | L715H + Y716D + P717S | A854C/A854D/A854E/A854F/A854H/A854G/A854L/A854R/A854T/A854K/A854Y |
| YD212 | L715I + Y716D + P717S | A854C/A854D/A854E/A854F/A854H/A854G/A854L/A854R/A854T/A854K/A854Y |
| YD213 | L715Q + Y716D + P717S | A854C/A854D/A854E/A854F/A854H/A854G/A854L/A854R/A854T/A854K/A854Y |
| YD214 | L715S + Y716D + P717S | A854C/A854D/A854E/A854F/A854H/A854G/A854L/A854R/A854T/A854K/A854Y |
| YD215 | L715W + Y716D + P717S | A854C/A854D/A854E/A854F/A854H/A854G/A854L/A854R/A854T/A854K/A854Y |
| YD216 | L715Y + Y716D + P717S | A854C/A854D/A854E/A854F/A854H/A854G/A854L/A854R/A854T/A854K/A854Y |
| YD217 | L715A + Y716F + P717S | A854C/A854D/A854E/A854F/A854H/A854G/A854L/A854R/A854T/A854K/A854Y |
| YD218 | L715F + Y716F + P717S | A854C/A854D/A854E/A854F/A854H/A854G/A854L/A854R/A854T/A854K/A854Y |
| YD219 | L715H + Y716F + P717S | A854C/A854D/A854E/A854F/A854H/A854G/A854L/A854R/A854T/A854K/A854Y |
| YD220 | L715I + Y716F + P717S | A854C/A854D/A854E/A854F/A854H/A854G/A854L/A854R/A854T/A854K/A854Y |
| YD221 | L715Q + Y716F + P717S | A854C/A854D/A854E/A854F/A854H/A854G/A854L/A854R/A854T/A854K/A854Y |
| YD222 | L715S + Y716F + P717S | A854C/A854D/A854E/A854F/A854H/A854G/A854L/A854R/A854T/A854K/A854Y |
| YD223 | L715W + Y716F + P717S | A854C/A854D/A854E/A854F/A854H/A854G/A854L/A854R/A854T/A854K/A854Y |
| YD224 | L715Y + Y716F + P717S | A854C/A854D/A854E/A854F/A854H/A854G/A854L/A854R/A854T/A854K/A854Y |
| YD225 | L715A + Y716G + P717S | A854C/A854D/A854E/A854F/A854H/A854G/A854L/A854R/A854T/A854K/A854Y |
| YD226 | L715F + Y716G + P717S | A854C/A854D/A854E/A854F/A854H/A854G/A854L/A854R/A854T/A854K/A854Y |
| YD227 | L715H + Y716G + P717S | A854C/A854D/A854E/A854F/A854H/A854G/A854L/A854R/A854T/A854K/A854Y |
| YD228 | L715I + Y716G + P717S | A854C/A854D/A854E/A854F/A854H/A854G/A854L/A854R/A854T/A854K/A854Y |
| YD229 | L715Q + Y716G + P717S | A854C/A854D/A854E/A854F/A854H/A854G/A854L/A854R/A854T/A854K/A854Y |
| YD230 | L715S + Y716G + P717S | A854C/A854D/A854E/A854F/A854H/A854G/A854L/A854R/A854T/A854K/A854Y |
| YD231 | L715W + Y716G + P717S | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD232 | L715Y + Y716G + P717S | A854C/A854D/A854E/A854F/A854H/A854G/A854L/A854R/A854T/A854K/A854Y |
| YD233 | L715A + Y716H + P717S | A854C/A854D/A854E/A854F/A854H/A854G/A854L/A854R/A854T/A854K/A854Y |
| YD234 | L715F + Y716H + P717S | A854C/A854D/A854E/A854F/A854H/A854G/A854L/A854R/A854T/A854K/A854Y |
| YD235 | L715H + Y716H + P717S | A854C/A854D/A854E/A854F/A854H/A854G/A854L/A854R/A854T/A854K/A854Y |
| YD236 | L715I + Y716H + P717S | A854C/A854D/A854E/A854F/A854H/A854G/A854L/A854R/A854T/A854K/A854Y |
| YD237 | L715Q + Y716H + P717S | A854C/A854D/A854E/A854F/A854H/A854G/A854L/A854R/A854T/A854K/A854Y |
| YD238 | L715S + Y716H + P717S | A854C/A854D/A854E/A854F/A854H/A854G/A854L/A854R/A854T/A854K/A854Y |
| YD239 | L715W + Y716H + P717S | A854C/A854D/A854E/A854F/A854H/A854G/A854L/A854R/A854T/A854K/A854Y |
| YD240 | L715Y + Y716H + P717S | A854C/A854D/A854E/A854F/A854H/A854G/A854L/A854R/A854T/A854K/A854Y |
| YD241 | L715A + Y716I + P717S | A854C/A854D/A854E/A854F/A854H/A854G/A854L/A854R/A854T/A854K/A854Y |
| YD242 | L715F + Y716I + P717S | A854C/A854D/A854E/A854F/A854H/A854G/A854L/A854R/A854T/A854K/A854Y |
| YD243 | L715H + Y716I + P717S | A854C/A854D/A854E/A854F/A854H/A854G/A854L/A854R/A854T/A854K/A854Y |
| YD244 | L715I + Y716I + P717S | A854C/A854D/A854E/A854F/A854H/A854G/A854L/A854R/A854T/A854K/A854Y |
| YD245 | L715Q + Y716I + P717S | A854C/A854D/A854E/A854F/A854H/A854G/A854L/A854R/A854T/A854K/A854Y |
| YD246 | L715S + Y716I + P717S | A854C/A854D/A854E/A854F/A854H/A854G/A854L/A854R/A854T/A854K/A854Y |
| YD247 | L715W + Y716I + P717S | A854C/A854D/A854E/A854F/A854H/A854G/A854L/A854R/A854T/A854K/A854Y |
| YD248 | L715Y + Y716I + P717S | A854C/A854D/A854E/A854F/A854H/A854G/A854L/A854R/A854T/A854K/A854Y |
| YD249 | L715A + Y716K + P717S | A854C/A854D/A854E/A854F/A854H/A854G/A854L/A854R/A854T/A854K/A854Y |
| YD250 | L715F + Y716K + P717S | A854C/A854D/A854E/A854F/A854H/A854G/A854L/A854R/A854T/A854K/A854Y |
| YD251 | L715H + Y716K + P717S | A854C/A854D/A854E/A854F/A854H/A854G/A854L/A854R/A854T/A854K/A854Y |
| YD252 | L715I + Y716K + P717S | A854C/A854D/A854E/A854F/A854H/A854G/A854L/A854R/A854T/A854K/A854Y |
| YD253 | L715Q + Y716K + P717S | A854C/A854D/A854E/A854F/A854H/A854G/A854L/A854R/A854T/A854K/A854Y |
| YD254 | L715S + Y716K + P717S | A854C/A854D/A854E/A854F/A854H/A854G/A854L/A854R/A854T/A854K/A854Y |
| YD255 | L715W + Y716K + P717S | A854C/A854D/A854E/A854F/A854H/A854G/A854L/A854R/A854T/A854K/A854Y |
| YD256 | L715Y + Y716K + P717S | A854C/A854D/A854E/A854F/A854H/A854G/A854L/A854R/A854T/A854K/A854Y |
| YD257 | L715A + Y716L + P717S | A854C/A854D/A854E/A854F/A854H/A854G/A854L/A854R/A854T/A854K/A854Y |
| YD258 | L715F + Y716L + P717S | A854C/A854D/A854E/A854F/A854H/A854G/A854L/A854R/A854T/A854K/A854Y |
| YD259 | L715H + Y716L + P717S | A854C/A854D/A854E/A854F/A854H/A854G/A854L/A854R/A854T/A854K/A854Y |
| YD260 | L715I + Y716L + P717S | A854C/A854D/A854E/A854F/A854H/A854G/A854L/A854R/A854T/A854K/A854Y |
| YD261 | L715Q + Y716L + P717S | A854C/A854D/A854E/A854F/A854H/A854G/A854L/A854R/A854T/A854K/A854Y |
| YD262 | L715S + Y716L + P717S | A854C/A854D/A854E/A854F/A854H/A854G/A854L/A854R/A854T/A854K/A854Y |
| YD263 | L715W + Y716L + P717S | A854C/A854D/A854E/A854F/A854H/A854G/A854L/A854R/A854T/A854K/A854Y |
| YD264 | L715Y + Y716L + P717S | A854C/A854D/A854E/A854F/A854H/A854G/A854L/A854R/A854T/A854K/A854Y |
| YD265 | L715A + Y716M + P717S | A854C/A854D/A854E/A854F/A854H/A854G/A854L/A854R/A854T/A854K/A854Y |
| YD266 | L715F + Y716M + P717S | A854C/A854D/A854E/A854F/A854H/A854G/A854L/A854R/A854T/A854K/A854Y |
| YD267 | L715H + Y716M + P717S | A854C/A854D/A854E/A854F/A854H/A854G/A854L/A854R/A854T/A854K/A854Y |
| YD268 | L715I + Y716M + P717S | A854C/A854D/A854E/A854F/A854H/A854G/A854L/A854R/A854T/A854K/A854Y |
| YD269 | L715Q + Y716M + P717S | A854C/A854D/A854E/A854F/A854H/A854G/A854L/A854R/A854T/A854K/A854Y |
| YD270 | L715S + Y716M + P717S | A854C/A854D/A854E/A854F/A854H/A854G/A854L/A854R/A854T/A854K/A854Y |
| YD271 | L715W + Y716M + P717S | A854C/A854D/A854E/A854F/A854H/A854G/A854L/A854R/A854T/A854K/A854Y |
| YD272 | L715Y + Y716M + P717S | A854C/A854D/A854E/A854F/A854H/A854G/A854L/A854R/A854T/A854K/A854Y |
| YD273 | L715A + Y716N + P717S | A854C/A854D/A854E/A854F/A854H/A854G/A854L/A854R/A854T/A854K/A854Y |
| YD274 | L715F + Y716N + P717S | A854C/A854D/A854E/A854F/A854H/A854G/A854L/A854R/A854T/A854K/A854Y |
| YD275 | L715H + Y716N + P717S | A854C/A854D/A854E/A854F/A854H/A854G/A854L/A854R/A854T/A854K/A854Y |
| YD276 | L715I + Y716N + P717S | A854C/A854D/A854E/A854F/A854H/A854G/A854L/A854R/A854T/A854K/A854Y |
| YD277 | L715Q + Y716N + P717S | A854C/A854D/A854E/A854F/A854H/A854G/A854L/A854R/A854T/A854K/A854Y |
| YD278 | L715S + Y716N + P717S | A854C/A854D/A854E/A854F/A854H/A854G/A854L/A854R/A854T/A854K/A854Y |
| YD279 | L715W + Y716N + P717S | A854C/A854D/A854E/A854F/A854H/A854G/A854L/A854R/A854T/A854K/A854Y |
| YD280 | L715Y + Y716N + P717S | A854C/A854D/A854E/A854F/A854H/A854G/A854L/A854R/A854T/A854K/A854Y |
| YD281 | L715A + Y716Q + P717S | A854C/A854D/A854E/A854F/A854H/A854G/A854L/A854R/A854T/A854K/A854Y |
| YD282 | L715F + Y716Q + P717S | A854C/A854D/A854E/A854F/A854H/A854G/A854L/A854R/A854T/A854K/A854Y |
| YD283 | L715H + Y716Q + P717S | A854C/A854D/A854E/A854F/A854H/A854G/A854L/A854R/A854T/A854K/A854Y |
| YD284 | L715I + Y716Q + P717S | A854C/A854D/A854E/A854F/A854H/A854G/A854L/A854R/A854T/A854K/A854Y |
| YD285 | L715Q + Y716Q + P717S | A854C/A854D/A854E/A854F/A854H/A854G/A854L/A854R/A854T/A854K/A854Y |
| YD286 | L715S + Y716Q + P717S | A854C/A854D/A854E/A854F/A854H/A854G/A854L/A854R/A854T/A854K/A854Y |
| YD287 | L715W + Y716Q + P717S | A854C/A854D/A854E/A854F/A854H/A854G/A854L/A854R/A854T/A854K/A854Y |
| YD288 | L715Y + Y716Q + P717S | A854C/A854D/A854E/A854F/A854H/A854G/A854L/A854R/A854T/A854K/A854Y |
| YD289 | L715A + Y716A + P717T | A854C/A854D/A854E/A854F/A854H/A854G/A854L/A854R/A854T/A854K/A854Y |
| YD290 | L715F + Y716A + P717T | A854C/A854D/A854E/A854F/A854H/A854G/A854L/A854R/A854T/A854K/A854Y |
| YD291 | L715H + Y716A + P717T | A854C/A854D/A854E/A854F/A854H/A854G/A854L/A854R/A854T/A854K/A854Y |
| YD292 | L715I + Y716A + P717T | A854C/A854D/A854E/A854F/A854H/A854G/A854L/A854R/A854T/A854K/A854Y |
| YD293 | L715Q + Y716A + P717T | A854C/A854D/A854E/A854F/A854H/A854G/A854L/A854R/A854T/A854K/A854Y |
| YD294 | L715S + Y716A + P717T | A854C/A854D/A854E/A854F/A854H/A854G/A854L/A854R/A854T/A854K/A854Y |
| YD295 | L715W + Y716A + P717T | A854C/A854D/A854E/A854F/A854H/A854G/A854L/A854R/A854T/A854K/A854Y |
| YD296 | L715Y + Y716A + P717T | A854C/A854D/A854E/A854F/A854H/A854G/A854L/A854R/A854T/A854K/A854Y |
| YD297 | L715A + Y716C + P717T | A854C/A854D/A854E/A854F/A854H/A854G/A854L/A854R/A854T/A854K/A854Y |
| YD298 | L715F + Y716C + P717T | A854C/A854D/A854E/A854F/A854H/A854G/A854L/A854R/A854T/A854K/A854Y |
| YD299 | L715H + Y716C + P717T | A854C/A854D/A854E/A854F/A854H/A854G/A854L/A854R/A854T/A854K/A854Y |
| YD300 | L715I + Y716C + P717T | A854C/A854D/A854E/A854F/A854H/A854G/A854L/A854R/A854T/A854K/A854Y |
| YD301 | L715Q + Y716C + P717T | A854C/A854D/A854E/A854F/A854H/A854G/A854L/A854R/A854T/A854K/A854Y |
| YD302 | L715S + Y716C + P717T | A854C/A854D/A854E/A854F/A854H/A854G/A854L/A854R/A854T/A854K/A854Y |
| YD303 | L715W + Y716C + P717T | A854C/A854D/A854E/A854F/A854H/A854G/A854L/A854R/A854T/A854K/A854Y |
| YD304 | L715Y + Y716C + P717T | A854C/A854D/A854E/A854F/A854H/A854G/A854L/A854R/A854T/A854K/A854Y |
| YD305 | L715A + Y716D + P717T | A854C/A854D/A854E/A854F/A854H/A854G/A854L/A854R/A854T/A854K/A854Y |
| YD306 | L715F + Y716D + P717T | A854C/A854D/A854E/A854F/A854H/A854G/A854L/A854R/A854T/A854K/A854Y |
| YD307 | L715H + Y716D + P717T | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD308 | L715I + Y716D + P717T | A854C/A854D/A854E/A854F/A854H/A854G/A854L/A854R/A854T/A854K/A854Y |
| YD309 | L715Q + Y716D + P717T | A854C/A854D/A854E/A854F/A854H/A854G/A854L/A854R/A854T/A854K/A854Y |
| YD310 | L715S + Y716D + P717T | A854C/A854D/A854E/A854F/A854H/A854G/A854L/A854R/A854T/A854K/A854Y |
| YD311 | L715W + Y716D + P717T | A854C/A854D/A854E/A854F/A854H/A854G/A854L/A854R/A854T/A854K/A854Y |
| YD312 | L715Y + Y716D + P717T | A854C/A854D/A854E/A854F/A854H/A854G/A854L/A854R/A854T/A854K/A854Y |
| YD313 | L715A + Y716F + P717T | A854C/A854D/A854E/A854F/A854H/A854G/A854L/A854R/A854T/A854K/A854Y |
| YD314 | L715F + Y716F + P717T | A854C/A854D/A854E/A854F/A854H/A854G/A854L/A854R/A854T/A854K/A854Y |
| YD315 | L715H + Y716F + P717T | A854C/A854D/A854E/A854F/A854H/A854G/A854L/A854R/A854T/A854K/A854Y |
| YD316 | L715I + Y716F + P717T | A854C/A854D/A854E/A854F/A854H/A854G/A854L/A854R/A854T/A854K/A854Y |
| YD317 | L715Q + Y716F + P717T | A854C/A854D/A854E/A854F/A854H/A854G/A854L/A854R/A854T/A854K/A854Y |
| YD318 | L715S + Y716F + P717T | A854C/A854D/A854E/A854F/A854H/A854G/A854L/A854R/A854T/A854K/A854Y |
| YD319 | L715W + Y716F + P717T | A854C/A854D/A854E/A854F/A854H/A854G/A854L/A854R/A854T/A854K/A854Y |
| YD320 | L715Y + Y716F + P717T | A854C/A854D/A854E/A854F/A854H/A854G/A854L/A854R/A854T/A854K/A854Y |
| YD321 | L715A + Y716G + P717T | A854C/A854D/A854E/A854F/A854H/A854G/A854L/A854R/A854T/A854K/A854Y |
| YD322 | L715F + Y716G + P717T | A854C/A854D/A854E/A854F/A854H/A854G/A854L/A854R/A854T/A854K/A854Y |
| YD323 | L715H + Y716G + P717T | A854C/A854D/A854E/A854F/A854H/A854G/A854L/A854R/A854T/A854K/A854Y |
| YD324 | L715I + Y716G + P717T | A854C/A854D/A854E/A854F/A854H/A854G/A854L/A854R/A854T/A854K/A854Y |
| YD325 | L715Q + Y716G + P717T | A854C/A854D/A854E/A854F/A854H/A854G/A854L/A854R/A854T/A854K/A854Y |
| YD326 | L715S + Y716G + P717T | A854C/A854D/A854E/A854F/A854H/A854G/A854L/A854R/A854T/A854K/A854Y |
| YD327 | L715W + Y716G + P717T | A854C/A854D/A854E/A854F/A854H/A854G/A854L/A854R/A854T/A854K/A854Y |
| YD328 | L715Y + Y716G + P717T | A854C/A854D/A854E/A854F/A854H/A854G/A854L/A854R/A854T/A854K/A854Y |
| YD329 | L715A + Y716H + P717T | A854C/A854D/A854E/A854F/A854H/A854G/A854L/A854R/A854T/A854K/A854Y |
| YD330 | L715F + Y716H + P717T | A854C/A854D/A854E/A854F/A854H/A854G/A854L/A854R/A854T/A854K/A854Y |
| YD331 | L715H + Y716H + P717T | A854C/A854D/A854E/A854F/A854H/A854G/A854L/A854R/A854T/A854K/A854Y |
| YD332 | L715I + Y716H + P717T | A854C/A854D/A854E/A854F/A854H/A854G/A854L/A854R/A854T/A854K/A854Y |
| YD333 | L715Q + Y716H + P717T | A854C/A854D/A854E/A854F/A854H/A854G/A854L/A854R/A854T/A854K/A854Y |
| YD334 | L715S + Y716H + P717T | A854C/A854D/A854E/A854F/A854H/A854G/A854L/A854R/A854T/A854K/A854Y |
| YD335 | L715W + Y716H + P717T | A854C/A854D/A854E/A854F/A854H/A854G/A854L/A854R/A854T/A854K/A854Y |
| YD336 | L715Y + Y716H + P717T | A854C/A854D/A854E/A854F/A854H/A854G/A854L/A854R/A854T/A854K/A854Y |
| YD337 | L715A + Y716I + P717T | A854C/A854D/A854E/A854F/A854H/A854G/A854L/A854R/A854T/A854K/A854Y |
| YD338 | L715F + Y716I + P717T | A854C/A854D/A854E/A854F/A854H/A854G/A854L/A854R/A854T/A854K/A854Y |
| YD339 | L715H + Y716I + P717T | A854C/A854D/A854E/A854F/A854H/A854G/A854L/A854R/A854T/A854K/A854Y |
| YD340 | L715I + Y716I + P717T | A854C/A854D/A854E/A854F/A854H/A854G/A854L/A854R/A854T/A854K/A854Y |
| YD341 | L715Q + Y716I + P717T | A854C/A854D/A854E/A854F/A854H/A854G/A854L/A854R/A854T/A854K/A854Y |
| YD342 | L715S + Y716I + P717T | A854C/A854D/A854E/A854F/A854H/A854G/A854L/A854R/A854T/A854K/A854Y |
| YD343 | L715W + Y716I + P717T | A854C/A854D/A854E/A854F/A854H/A854G/A854L/A854R/A854T/A854K/A854Y |
| YD344 | L715Y + Y716I + P717T | A854C/A854D/A854E/A854F/A854H/A854G/A854L/A854R/A854T/A854K/A854Y |
| YD345 | L715A + Y716K + P717T | A854C/A854D/A854E/A854F/A854H/A854G/A854L/A854R/A854T/A854K/A854Y |
| YD346 | L715F + Y716K + P717T | A854C/A854D/A854E/A854F/A854H/A854G/A854L/A854R/A854T/A854K/A854Y |
| YD347 | L715H + Y716K + P717T | A854C/A854D/A854E/A854F/A854H/A854G/A854L/A854R/A854T/A854K/A854Y |
| YD348 | L715I + Y716K + P717T | A854C/A854D/A854E/A854F/A854H/A854G/A854L/A854R/A854T/A854K/A854Y |
| YD349 | L715Q + Y716K + P717T | A854C/A854D/A854E/A854F/A854H/A854G/A854L/A854R/A854T/A854K/A854Y |
| YD350 | L715S + Y716K + P717T | A854C/A854D/A854E/A854F/A854H/A854G/A854L/A854R/A854T/A854K/A854Y |
| YD351 | L715W + Y716K + P717T | A854C/A854D/A854E/A854F/A854H/A854G/A854L/A854R/A854T/A854K/A854Y |
| YD352 | L715Y + Y716K + P717T | A854C/A854D/A854E/A854F/A854H/A854G/A854L/A854R/A854T/A854K/A854Y |
| YD353 | L715A + Y716L + P717T | A854C/A854D/A854E/A854F/A854H/A854G/A854L/A854R/A854T/A854K/A854Y |
| YD354 | L715F + Y716L + P717T | A854C/A854D/A854E/A854F/A854H/A854G/A854L/A854R/A854T/A854K/A854Y |
| YD355 | L715H + Y716L + P717T | A854C/A854D/A854E/A854F/A854H/A854G/A854L/A854R/A854T/A854K/A854Y |
| YD356 | L715I + Y716L + P717T | A854C/A854D/A854E/A854F/A854H/A854G/A854L/A854R/A854T/A854K/A854Y |
| YD357 | L715Q + Y716L + P717T | A854C/A854D/A854E/A854F/A854H/A854G/A854L/A854R/A854T/A854K/A854Y |
| YD358 | L715S + Y716L + P717T | A854C/A854D/A854E/A854F/A854H/A854G/A854L/A854R/A854T/A854K/A854Y |
| YD359 | L715W + Y716L + P717T | A854C/A854D/A854E/A854F/A854H/A854G/A854L/A854R/A854T/A854K/A854Y |
| YD360 | L715Y + Y716L + P717T | A854C/A854D/A854E/A854F/A854H/A854G/A854L/A854R/A854T/A854K/A854Y |
| YD361 | L715A + Y716M + P717T | A854C/A854D/A854E/A854F/A854H/A854G/A854L/A854R/A854T/A854K/A854Y |
| YD362 | L715F + Y716M + P717T | A854C/A854D/A854E/A854F/A854H/A854G/A854L/A854R/A854T/A854K/A854Y |
| YD363 | L715H + Y716M + P717T | A854C/A854D/A854E/A854F/A854H/A854G/A854L/A854R/A854T/A854K/A854Y |
| YD364 | L715I + Y716M + P717T | A854C/A854D/A854E/A854F/A854H/A854G/A854L/A854R/A854T/A854K/A854Y |
| YD365 | L715Q + Y716M + P717T | A854C/A854D/A854E/A854F/A854H/A854G/A854L/A854R/A854T/A854K/A854Y |
| YD366 | L715S + Y716M + P717T | A854C/A854D/A854E/A854F/A854H/A854G/A854L/A854R/A854T/A854K/A854Y |
| YD367 | L715W + Y716M + P717T | A854C/A854D/A854E/A854F/A854H/A854G/A854L/A854R/A854T/A854K/A854Y |
| YD368 | L715Y + Y716M + P717T | A854C/A854D/A854E/A854F/A854H/A854G/A854L/A854R/A854T/A854K/A854Y |
| YD369 | L715A + Y716N + P717T | A854C/A854D/A854E/A854F/A854H/A854G/A854L/A854R/A854T/A854K/A854Y |
| YD370 | L715F + Y716N + P717T | A854C/A854D/A854E/A854F/A854H/A854G/A854L/A854R/A854T/A854K/A854Y |
| YD371 | L715H + Y716N + P717T | A854C/A854D/A854E/A854F/A854H/A854G/A854L/A854R/A854T/A854K/A854Y |
| YD372 | L715I + Y716N + P717T | A854C/A854D/A854E/A854F/A854H/A854G/A854L/A854R/A854T/A854K/A854Y |
| YD373 | L715Q + Y716N + P717T | A854C/A854D/A854E/A854F/A854H/A854G/A854L/A854R/A854T/A854K/A854Y |
| YD374 | L715S + Y716N + P717T | A854C/A854D/A854E/A854F/A854H/A854G/A854L/A854R/A854T/A854K/A854Y |
| YD375 | L715W + Y716N + P717T | A854C/A854D/A854E/A854F/A854H/A854G/A854L/A854R/A854T/A854K/A854Y |
| YD376 | L715Y + Y716N + P717T | A854C/A854D/A854E/A854F/A854H/A854G/A854L/A854R/A854T/A854K/A854Y |
| YD377 | L715A + Y716Q + P717T | A854C/A854D/A854E/A854F/A854H/A854G/A854L/A854R/A854T/A854K/A854Y |
| YD378 | L715F + Y716Q + P717T | A854C/A854D/A854E/A854F/A854H/A854G/A854L/A854R/A854T/A854K/A854Y |
| YD379 | L715H + Y716Q + P717T | A854C/A854D/A854E/A854F/A854H/A854G/A854L/A854R/A854T/A854K/A854Y |
| YD380 | L715I + Y716Q + P717T | A854C/A854D/A854E/A854F/A854H/A854G/A854L/A854R/A854T/A854K/A854Y |
| YD381 | L715Q + Y716Q + P717T | A854C/A854D/A854E/A854F/A854H/A854G/A854L/A854R/A854T/A854K/A854Y |
| YD382 | L715S + Y716Q + P717T | A854C/A854D/A854E/A854F/A854H/A854G/A854L/A854R/A854T/A854K/A854Y |
| YD383 | L715W + Y716Q + P717T | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD384 | L715Y + Y716Q + P717T | A854C/A854D/A854E/A854F/A854H/A854G/A854L/A854R/A854T/A854K/A854Y |
| YD385 | L715A | A854C/A854D/A854E/A854F/A854H/A854G/A854L/A854R/A854T/A854K/A854Y |
| YD386 | L715F | A854C/A854D/A854E/A854F/A854H/A854G/A854L/A854R/A854T/A854K/A854Y |
| YD387 | L715H | A854C/A854D/A854E/A854F/A854H/A854G/A854L/A854R/A854T/A854K/A854Y |
| YD388 | L715I | A854C/A854D/A854E/A854F/A854H/A854G/A854L/A854R/A854T/A854K/A854Y |
| YD389 | L715Q | A854C/A854D/A854E/A854F/A854H/A854G/A854L/A854R/A854T/A854K/A854Y |
| YD390 | L715S | A854C/A854D/A854E/A854F/A854H/A854G/A854L/A854R/A854T/A854K/A854Y |
| YD391 | L715W | A854C/A854D/A854E/A854F/A854H/A854G/A854L/A854R/A854T/A854K/A854Y |
| YD392 | L715Y | A854C/A854D/A854E/A854F/A854H/A854G/A854L/A854R/A854T/A854K/A854Y |
| YD393 | L715A + Y716A | A854C/A854D/A854E/A854F/A854H/A854G/A854L/A854R/A854T/A854K/A854Y |
| YD394 | L715F + Y716A | A854C/A854D/A854E/A854F/A854H/A854G/A854L/A854R/A854T/A854K/A854Y |
| YD395 | L715H + Y716A | A854C/A854D/A854E/A854F/A854H/A854G/A854L/A854R/A854T/A854K/A854Y |
| YD396 | L715I + Y716A | A854C/A854D/A854E/A854F/A854H/A854G/A854L/A854R/A854T/A854K/A854Y |
| YD397 | L715Q + Y716A | A854C/A854D/A854E/A854F/A854H/A854G/A854L/A854R/A854T/A854K/A854Y |
| YD398 | L715S + Y716A | A854C/A854D/A854E/A854F/A854H/A854G/A854L/A854R/A854T/A854K/A854Y |
| YD399 | L715W + Y716A | A854C/A854D/A854E/A854F/A854H/A854G/A854L/A854R/A854T/A854K/A854Y |
| YD400 | L715Y + Y716A | A854C/A854D/A854E/A854F/A854H/A854G/A854L/A854R/A854T/A854K/A854Y |
| YD401 | L715A + Y716C | A854C/A854D/A854E/A854F/A854H/A854G/A854L/A854R/A854T/A854K/A854Y |
| YD402 | L715F + Y716C | A854C/A854D/A854E/A854F/A854H/A854G/A854L/A854R/A854T/A854K/A854Y |
| YD403 | L715H + Y716C | A854C/A854D/A854E/A854F/A854H/A854G/A854L/A854R/A854T/A854K/A854Y |
| YD404 | L715I + Y716C | A854C/A854D/A854E/A854F/A854H/A854G/A854L/A854R/A854T/A854K/A854Y |
| YD405 | L715Q + Y716C | A854C/A854D/A854E/A854F/A854H/A854G/A854L/A854R/A854T/A854K/A854Y |
| YD406 | L715S + Y716C | A854C/A854D/A854E/A854F/A854H/A854G/A854L/A854R/A854T/A854K/A854Y |
| YD407 | L715W + Y716C | A854C/A854D/A854E/A854F/A854H/A854G/A854L/A854R/A854T/A854K/A854Y |
| YD408 | L715Y + Y716C | A854C/A854D/A854E/A854F/A854H/A854G/A854L/A854R/A854T/A854K/A854Y |
| YD409 | L715A + Y716D | A854C/A854D/A854E/A854F/A854H/A854G/A854L/A854R/A854T/A854K/A854Y |
| YD410 | L715F + Y716D | A854C/A854D/A854E/A854F/A854H/A854G/A854L/A854R/A854T/A854K/A854Y |
| YD411 | L715H + Y716D | A854C/A854D/A854E/A854F/A854H/A854G/A854L/A854R/A854T/A854K/A854Y |
| YD412 | L715I + Y716D | A854C/A854D/A854E/A854F/A854H/A854G/A854L/A854R/A854T/A854K/A854Y |
| YD413 | L715Q + Y716D | A854C/A854D/A854E/A854F/A854H/A854G/A854L/A854R/A854T/A854K/A854Y |
| YD414 | L715S + Y716D | A854C/A854D/A854E/A854F/A854H/A854G/A854L/A854R/A854T/A854K/A854Y |
| YD415 | L715W + Y716D | A854C/A854D/A854E/A854F/A854H/A854G/A854L/A854R/A854T/A854K/A854Y |
| YD416 | L715Y + Y716D | A854C/A854D/A854E/A854F/A854H/A854G/A854L/A854R/A854T/A854K/A854Y |
| YD417 | L715A + Y716F | A854C/A854D/A854E/A854F/A854H/A854G/A854L/A854R/A854T/A854K/A854Y |
| YD418 | L715F + Y716F | A854C/A854D/A854E/A854F/A854H/A854G/A854L/A854R/A854T/A854K/A854Y |
| YD419 | L715H + Y716F | A854C/A854D/A854E/A854F/A854H/A854G/A854L/A854R/A854T/A854K/A854Y |
| YD420 | L715I + Y716F | A854C/A854D/A854E/A854F/A854H/A854G/A854L/A854R/A854T/A854K/A854Y |
| YD421 | L715Q + Y716F | A854C/A854D/A854E/A854F/A854H/A854G/A854L/A854R/A854T/A854K/A854Y |
| YD422 | L715S + Y716F | A854C/A854D/A854E/A854F/A854H/A854G/A854L/A854R/A854T/A854K/A854Y |
| YD423 | L715W + Y716F | A854C/A854D/A854E/A854F/A854H/A854G/A854L/A854R/A854T/A854K/A854Y |
| YD424 | L715Y + Y716F | A854C/A854D/A854E/A854F/A854H/A854G/A854L/A854R/A854T/A854K/A854Y |
| YD425 | L715A + Y716G | A854C/A854D/A854E/A854F/A854H/A854G/A854L/A854R/A854T/A854K/A854Y |
| YD426 | L715F + Y716G | A854C/A854D/A854E/A854F/A854H/A854G/A854L/A854R/A854T/A854K/A854Y |
| YD427 | L715H + Y716G | A854C/A854D/A854E/A854F/A854H/A854G/A854L/A854R/A854T/A854K/A854Y |
| YD428 | L715I + Y716G | A854C/A854D/A854E/A854F/A854H/A854G/A854L/A854R/A854T/A854K/A854Y |
| YD429 | L715Q + Y716G | A854C/A854D/A854E/A854F/A854H/A854G/A854L/A854R/A854T/A854K/A854Y |
| YD430 | L715S + Y716G | A854C/A854D/A854E/A854F/A854H/A854G/A854L/A854R/A854T/A854K/A854Y |
| YD431 | L715W + Y716G | A854C/A854D/A854E/A854F/A854H/A854G/A854L/A854R/A854T/A854K/A854Y |
| YD432 | L715Y + Y716G | A854C/A854D/A854E/A854F/A854H/A854G/A854L/A854R/A854T/A854K/A854Y |
| YD433 | L715A + Y716H | A854C/A854D/A854E/A854F/A854H/A854G/A854L/A854R/A854T/A854K/A854Y |
| YD434 | L715F + Y716H | A854C/A854D/A854E/A854F/A854H/A854G/A854L/A854R/A854T/A854K/A854Y |
| YD435 | L715H + Y716H | A854C/A854D/A854E/A854F/A854H/A854G/A854L/A854R/A854T/A854K/A854Y |
| YD436 | L715I + Y716H | A854C/A854D/A854E/A854F/A854H/A854G/A854L/A854R/A854T/A854K/A854Y |
| YD437 | L715Q + Y716H | A854C/A854D/A854E/A854F/A854H/A854G/A854L/A854R/A854T/A854K/A854Y |
| YD438 | L715S + Y716H | A854C/A854D/A854E/A854F/A854H/A854G/A854L/A854R/A854T/A854K/A854Y |
| YD439 | L715W + Y716H | A854C/A854D/A854E/A854F/A854H/A854G/A854L/A854R/A854T/A854K/A854Y |
| YD440 | L715Y + Y716H | A854C/A854D/A854E/A854F/A854H/A854G/A854L/A854R/A854T/A854K/A854Y |
| YD441 | L715A + Y716I | A854C/A854D/A854E/A854F/A854H/A854G/A854L/A854R/A854T/A854K/A854Y |
| YD442 | L715F + Y716I | A854C/A854D/A854E/A854F/A854H/A854G/A854L/A854R/A854T/A854K/A854Y |
| YD443 | L715H + Y716I | A854C/A854D/A854E/A854F/A854H/A854G/A854L/A854R/A854T/A854K/A854Y |
| YD444 | L715I + Y716I | A854C/A854D/A854E/A854F/A854H/A854G/A854L/A854R/A854T/A854K/A854Y |
| YD445 | L715Q + Y716I | A854C/A854D/A854E/A854F/A854H/A854G/A854L/A854R/A854T/A854K/A854Y |
| YD446 | L715S + Y716I | A854C/A854D/A854E/A854F/A854H/A854G/A854L/A854R/A854T/A854K/A854Y |
| YD447 | L715W + Y716I | A854C/A854D/A854E/A854F/A854H/A854G/A854L/A854R/A854T/A854K/A854Y |
| YD448 | L715Y + Y716I | A854C/A854D/A854E/A854F/A854H/A854G/A854L/A854R/A854T/A854K/A854Y |
| YD449 | L715A + Y716K | A854C/A854D/A854E/A854F/A854H/A854G/A854L/A854R/A854T/A854K/A854Y |
| YD450 | L715F + Y716K | A854C/A854D/A854E/A854F/A854H/A854G/A854L/A854R/A854T/A854K/A854Y |
| YD451 | L715H + Y716K | A854C/A854D/A854E/A854F/A854H/A854G/A854L/A854R/A854T/A854K/A854Y |
| YD452 | L715I + Y716K | A854C/A854D/A854E/A854F/A854H/A854G/A854L/A854R/A854T/A854K/A854Y |
| YD453 | L715Q + Y716K | A854C/A854D/A854E/A854F/A854H/A854G/A854L/A854R/A854T/A854K/A854Y |
| YD454 | L715S + Y716K | A854C/A854D/A854E/A854F/A854H/A854G/A854L/A854R/A854T/A854K/A854Y |
| YD455 | L715W + Y716K | A854C/A854D/A854E/A854F/A854H/A854G/A854L/A854R/A854T/A854K/A854Y |
| YD456 | L715Y + Y716K | A854C/A854D/A854E/A854F/A854H/A854G/A854L/A854R/A854T/A854K/A854Y |
| YD457 | L715A + Y716L | A854C/A854D/A854E/A854F/A854H/A854G/A854L/A854R/A854T/A854K/A854Y |
| YD458 | L715F + Y716L | A854C/A854D/A854E/A854F/A854H/A854G/A854L/A854R/A854T/A854K/A854Y |
| YD459 | L715H + Y716L | A854C/A854D/A854E/A854F/A854H/A854G/A854L/A854R/A854T/A854K/A854Y |

TABLE 1-continued

List of PolB variants having the amino acid substitutions according to SEQ ID NO: 1.

| Name | Essential substitutions | Reinforceable substitutions |
|---|---|---|
| YD460 | L715I + Y716L | A854C/A854D/A854E/A854F/A854H/A854G/A854L/A854R/A854T/A854K/A854Y |
| YD461 | L715Q + Y716L | A854C/A854D/A854E/A854F/A854H/A854G/A854L/A854R/A854T/A854K/A854Y |
| YD462 | L715S + Y716L | A854C/A854D/A854E/A854F/A854H/A854G/A854L/A854R/A854T/A854K/A854Y |
| YD463 | L715W + Y716L | A854C/A854D/A854E/A854F/A854H/A854G/A854L/A854R/A854T/A854K/A854Y |
| YD464 | L715Y + Y716L | A854C/A854D/A854E/A854F/A854H/A854G/A854L/A854R/A854T/A854K/A854Y |
| YD465 | L715A + Y716M | A854C/A854D/A854E/A854F/A854H/A854G/A854L/A854R/A854T/A854K/A854Y |
| YD466 | L715F + Y716M | A854C/A854D/A854E/A854F/A854H/A854G/A854L/A854R/A854T/A854K/A854Y |
| YD467 | L715H + Y716M | A854C/A854D/A854E/A854F/A854H/A854G/A854L/A854R/A854T/A854K/A854Y |
| YD468 | L715I + Y716M | A854C/A854D/A854E/A854F/A854H/A854G/A854L/A854R/A854T/A854K/A854Y |
| YD469 | L715Q + Y716M | A854C/A854D/A854E/A854F/A854H/A854G/A854L/A854R/A854T/A854K/A854Y |
| YD470 | L715S + Y716M | A854C/A854D/A854E/A854F/A854H/A854G/A854L/A854R/A854T/A854K/A854Y |
| YD471 | L715W + Y716M | A854C/A854D/A854E/A854F/A854H/A854G/A854L/A854R/A854T/A854K/A854Y |
| YD472 | L715Y + Y716M | A854C/A854D/A854E/A854F/A854H/A854G/A854L/A854R/A854T/A854K/A854Y |
| YD473 | L715A + Y716N | A854C/A854D/A854E/A854F/A854H/A854G/A854L/A854R/A854T/A854K/A854Y |
| YD474 | L715F + Y716N | A854C/A854D/A854E/A854F/A854H/A854G/A854L/A854R/A854T/A854K/A854Y |
| YD475 | L715H + Y716N | A854C/A854D/A854E/A854F/A854H/A854G/A854L/A854R/A854T/A854K/A854Y |
| YD476 | L715I + Y716N | A854C/A854D/A854E/A854F/A854H/A854G/A854L/A854R/A854T/A854K/A854Y |
| YD477 | L715Q + Y716N | A854C/A854D/A854E/A854F/A854H/A854G/A854L/A854R/A854T/A854K/A854Y |
| YD478 | L715S + Y716N | A854C/A854D/A854E/A854F/A854H/A854G/A854L/A854R/A854T/A854K/A854Y |
| YD479 | L715W + Y716N | A854C/A854D/A854E/A854F/A854H/A854G/A854L/A854R/A854T/A854K/A854Y |
| YD480 | L715Y + Y716N | A854C/A854D/A854E/A854F/A854H/A854G/A854L/A854R/A854T/A854K/A854Y |
| YD481 | L715A + Y716Q | A854C/A854D/A854E/A854F/A854H/A854G/A854L/A854R/A854T/A854K/A854Y |
| YD482 | L715F + Y716Q | A854C/A854D/A854E/A854F/A854H/A854G/A854L/A854R/A854T/A854K/A854Y |
| YD483 | L715H + Y716Q | A854C/A854D/A854E/A854F/A854H/A854G/A854L/A854R/A854T/A854K/A854Y |
| YD484 | L715I + Y716Q | A854C/A854D/A854E/A854F/A854H/A854G/A854L/A854R/A854T/A854K/A854Y |
| YD485 | L715Q + Y716Q | A854C/A854D/A854E/A854F/A854H/A854G/A854L/A854R/A854T/A854K/A854Y |
| YD486 | L715S + Y716Q | A854C/A854D/A854E/A854F/A854H/A854G/A854L/A854R/A854T/A854K/A854Y |
| YD487 | L715W + Y716Q | A854C/A854D/A854E/A854F/A854H/A854G/A854L/A854R/A854T/A854K/A854Y |
| YD488 | L715Y + Y716Q | A854C/A854D/A854E/A854F/A854H/A854G/A854L/A854R/A854T/A854K/A854Y |
| YD489 | L715A + P717A | A854C/A854D/A854E/A854F/A854H/A854G/A854L/A854R/A854T/A854K/A854Y |
| YD490 | L715F + P717A | A854C/A854D/A854E/A854F/A854H/A854G/A854L/A854R/A854T/A854K/A854Y |
| YD491 | L715H + P717A | A854C/A854D/A854E/A854F/A854H/A854G/A854L/A854R/A854T/A854K/A854Y |
| YD492 | L715I + P717A | A854C/A854D/A854E/A854F/A854H/A854G/A854L/A854R/A854T/A854K/A854Y |
| YD493 | L715Q + P717A | A854C/A854D/A854E/A854F/A854H/A854G/A854L/A854R/A854T/A854K/A854Y |
| YD494 | L715S + P717A | A854C/A854D/A854E/A854F/A854H/A854G/A854L/A854R/A854T/A854K/A854Y |
| YD495 | L715W + P717A | A854C/A854D/A854E/A854F/A854H/A854G/A854L/A854R/A854T/A854K/A854Y |
| YD496 | L715Y + P717A | A854C/A854D/A854E/A854F/A854H/A854G/A854L/A854R/A854T/A854K/A854Y |
| YD497 | L715A + P717G | A854C/A854D/A854E/A854F/A854H/A854G/A854L/A854R/A854T/A854K/A854Y |
| YD498 | L715F + P717G | A854C/A854D/A854E/A854F/A854H/A854G/A854L/A854R/A854T/A854K/A854Y |
| YD499 | L715H + P717G | A854C/A854D/A854E/A854F/A854H/A854G/A854L/A854R/A854T/A854K/A854Y |
| YD500 | L715I + P717G | A854C/A854D/A854E/A854F/A854H/A854G/A854L/A854R/A854T/A854K/A854Y |
| YD501 | L715Q + P717G | A854C/A854D/A854E/A854F/A854H/A854G/A854L/A854R/A854T/A854K/A854Y |
| YD502 | L715S + P717G | A854C/A854D/A854E/A854F/A854H/A854G/A854L/A854R/A854T/A854K/A854Y |
| YD503 | L715W + P717G | A854C/A854D/A854E/A854F/A854H/A854G/A854L/A854R/A854T/A854K/A854Y |
| YD504 | L715Y + P717G | A854C/A854D/A854E/A854F/A854H/A854G/A854L/A854R/A854T/A854K/A854Y |
| YD505 | L715A + P717S | A854C/A854D/A854E/A854F/A854H/A854G/A854L/A854R/A854T/A854K/A854Y |
| YD506 | L715F + P717S | A854C/A854D/A854E/A854F/A854H/A854G/A854L/A854R/A854T/A854K/A854Y |
| YD507 | L715H + P717S | A854C/A854D/A854E/A854F/A854H/A854G/A854L/A854R/A854T/A854K/A854Y |
| YD508 | L715I + P717S | A854C/A854D/A854E/A854F/A854H/A854G/A854L/A854R/A854T/A854K/A854Y |
| YD509 | L715Q + P717S | A854C/A854D/A854E/A854F/A854H/A854G/A854L/A854R/A854T/A854K/A854Y |
| YD510 | L715S + P717S | A854C/A854D/A854E/A854F/A854H/A854G/A854L/A854R/A854T/A854K/A854Y |
| YD511 | L715W + P717S | A854C/A854D/A854E/A854F/A854H/A854G/A854L/A854R/A854T/A854K/A854Y |
| YD512 | L715Y + P717S | A854C/A854D/A854E/A854F/A854H/A854G/A854L/A854R/A854T/A854K/A854Y |
| YD513 | L715A + P717T | A854C/A854D/A854E/A854F/A854H/A854G/A854L/A854R/A854T/A854K/A854Y |
| YD514 | L715F + P717T | A854C/A854D/A854E/A854F/A854H/A854G/A854L/A854R/A854T/A854K/A854Y |
| YD515 | L715H + P717T | A854C/A854D/A854E/A854F/A854H/A854G/A854L/A854R/A854T/A854K/A854Y |
| YD516 | L715I + P717T | A854C/A854D/A854E/A854F/A854H/A854G/A854L/A854R/A854T/A854K/A854Y |
| YD517 | L715Q + P717T | A854C/A854D/A854E/A854F/A854H/A854G/A854L/A854R/A854T/A854K/A854Y |
| YD518 | L715S + P717T | A854C/A854D/A854E/A854F/A854H/A854G/A854L/A854R/A854T/A854K/A854Y |
| YD519 | L715W + P717T | A854C/A854D/A854E/A854F/A854H/A854G/A854L/A854R/A854T/A854K/A854Y |
| YD520 | L715Y + P717T | A854C/A854D/A854E/A854F/A854H/A854G/A854L/A854R/A854T/A854K/A854Y |

In accordance with some embodiments, the B-family DNA polymerase variant is modified from a wild-type B-family DNA polymerase having an amino acid sequence selected from the group consisting of SEQ ID NOs: 2, 3, 4, 5, 6, 7, 8, 9, 10, 11, 12, 13, 14, 15, 16 and 17, which are derived from the wild-type B-family DNA polymerase of Thermococcus gorgonarius DNA polymerase (Tgo), Thermococcus kodakarensis DNA polymerase (Kod1), Thermococcus sp. (strain 9°N-7) DNA polymerase (9°N), Pyrococcus furiosus DNA polymerase (Pfu), Thermococcus litoralis DNA polymerase (Vent), Methanosarcina acetivorans DNA polymerase (Mac), Pyrobaculum islandicum DNA polymerase (Pis), Sulfolobus solfataricus DNA polymerase (Sso), Methanococcus maripaludis DNA polymerase (Mma), human DNA polymerase delta catalytic p125 subunit (hPOLD), Saccharomyces cerevisiae DNA polymerase delta catalytic subunit (SecPOLD), Pseudomonas aeruginosa DNA polymerase II (Pae), Escherichia coli DNA polymerase II (Eco), Escherichia phage RB69 DNA polymerase (RB69), Escherichia phage T4 DNA polymerase (T4), and Bacillus phage Phi29 DNA polymerase (Phi29), respectively.

In accordance with some embodiments, the polymerases substantially lack a 3'-exonuclease or other editing activities; therefore, the PolB variants provided herein have deficient 3' to 5' exonuclease activity. The 3' to 5' exonuclease activity deficiency can be reached by any means. For example, practically, the 3' to 5' exonuclease activity can be reduced, attenuated, removed or inactivated by modifying the 3' to 5' exonucleolytic domain of the polymerase to generate a polymerase that is deficient in or absence of the 3' to 5' exonuclease activity. Preferably, the means of amino acid substitution is adapted to modify the 3' to 5' exonucleolytic domain. For example, the PolB variants may have functionally equivalent or positionally equivalent substitutions of the native D with A at position 354 (D354A) and the native E with A at position 356 (E356A) in the motif Exo I of SEQ ID NO:1, thereby causing a 3'-5' exonuclease deficiency.

In accordance with certain embodiments, the amino acid L or M corresponding to position 715 of SEQ ID NO:1 is substituted with A, F, H, I, Q, S, W, or Y; the amino acid Y corresponding to position 716 of SEQ ID NO:1 is not substituted or substituted with A, C, D, F, G, H, I, K, L, M, N, or Q; and the amino acid P of corresponding to position 717 of SEQ ID NO:1 is not substituted or substituted with A, G, S, or T.

In accordance with some embodiments, the B-family DNA polymerase variant having deficient 3' to 5' exonuclease activity is derived from *Thermococcus gorgonarius* DNA polymerase (Tgo) having a wild-type amino acid sequence of SEQ ID NO:2; and wherein the amino acid L at position 408 of SEQ ID NO: 2 is substituted with A, F, H, I, Q, S, W, or Y; the amino acid Y at position 409 of SEQ ID NO: 2 is not substituted or substituted with A, C, D, F, G, H, I, K, L, M, N, or Q; and the amino acid P at position 410 of SEQ ID NO: 2 is not substituted or substituted with A, G, S, or T.

In accordance with some embodiments, the B-family DNA polymerase variant having deficient 3' to 5' exonuclease activity is derived from *Thermococcus gorgonarius* DNA polymerase (Tgo) having a wild-type amino acid sequence of SEQ ID NO: 2; and wherein the amino acid L at position 408 of SEQ ID NO: 2 is substituted with A, F, H, I, Q, S, W, or Y; the amino acid Y at position 409 of SEQ ID NO: 2 is not substituted or substituted with A, C, D, F, G, H, I, K, L, M, N, or Q; the amino acid P at position 410 of SEQ ID NO: 2 is not substituted or substituted with A, G, S, or T; and the amino acid A at position 485 of SEQ ID NO: 2 is substituted with C, D, E, F, G, H, K, L, R, T, or Y.

In accordance with some embodiments, the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein the amino acid L at position 408 of SEQ ID NO: 3 is substituted with A, F, H, I, Q, S, W, or Y; the amino acid Y at position 409 of SEQ ID NO: 3 is not substituted or substituted with A, C, D, F, G, H, I, K, L, M, N, or Q; and the amino acid P at position 410 of SEQ ID NO: 3 is not substituted or substituted with A, G, S, or T.

In accordance with some embodiments, the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein the amino acid L at position 408 of SEQ ID NO: 3 is substituted with A, F, H, I, Q, S, W, or Y; the amino acid Y at position 409 of SEQ ID NO: 3 is not substituted or substituted with A, C, D, F, G, H, I, K, L, M, N, or Q; the amino acid P at position 410 of SEQ ID NO: 3 is not substituted or substituted with A, G, S, or T; and the amino acid A at position 485 of SEQ ID NO: 3 is substituted with C, D, E, F, G, H, K, L, R, T, or Y.

In accordance with some embodiments, the B-family DNA polymerase variant having deficient 3' to 5' exonuclease activity is derived from *Thermococcus* sp. (strain 9°N-7) DNA polymerase (9°N) having a wild-type amino acid sequence of SEQ ID NO: 4; and wherein the amino acid L at position 408 of SEQ ID NO: 4 is substituted with A, F, H, I, Q, S, W, or Y; the amino acid Y at position 409 of SEQ ID NO: 4 is not substituted or substituted with A, C, D, F, G, H, I, K, L, M, N, or Q; and the amino acid P at position 410 of SEQ ID NO: 4 is not substituted or substituted with A, G, S, or T.

In accordance with some embodiments, the B-family DNA polymerase variant having deficient 3' to 5' exonuclease activity is derived from *Thermococcus* sp. (strain 9°N-7) DNA polymerase (9°N) having a wild-type amino acid sequence of SEQ ID NO: 4; and wherein the amino acid L at position 408 of SEQ ID NO: 4 is substituted with A, F, H, I, Q, S, W, or Y; the amino acid Y at position 409 of SEQ ID NO: 4 is not substituted or substituted with A, C, D, F, G, H, I, K, L, M, N, or Q; the amino acid P at position 410 of SEQ ID NO: 4 is not substituted or substituted with A, G, S, or T; and the amino acid A at position 485 of SEQ ID NO: 4 is substituted with C, D, E, F, G, H, K, L, R, T, or Y.

In accordance with some embodiments, the B-family DNA polymerase variant having inactive 3' to 5' exonuclease activity is derived from *Pyrococcus furiosus* DNA polymerase (Pfu) having a wild-type amino acid sequence of SEQ ID NO: 5; and wherein the amino acid L at position 409 of SEQ ID NO: 5 is substituted with A, F, H, I, Q, S, W, or Y; the amino acid Y at position 410 of SEQ ID NO: 5 is not substituted or substituted with A, C, D, F, G, H, I, K, L, M, N, or Q; and the amino acid P at position 411 of SEQ ID NO: 5 is not substituted or substituted with A, G, S, or T.

In accordance with some embodiments, the B-family DNA polymerase variant having deficient 3' to 5' exonuclease activity is derived from *Pyrococcus furiosus* DNA polymerase (Pfu) having a wild-type amino acid sequence of SEQ ID NO: 5; and wherein the amino acid L at position 409 of SEQ ID NO: 5 is substituted with A, F, H, I, Q, S, W, or Y; the amino acid Y at position 410 of SEQ ID NO: 5 is not substituted or substituted with A, C, D, F, G, H, I, K, L, M, N, or Q; the amino acid P at position 411 of SEQ ID NO: 5 is not substituted or substituted with A, G, S, or T; and the amino acid A at position 486 of SEQ ID NO: 5 is substituted with C, D, E, F, G, H, K, L, R, T, or Y.

In accordance with some embodiments, the B-family DNA polymerase variant having deficient 3' to 5' exonuclease activity is derived from *Thermococcus litoralis* DNA polymerase (Vent) having a wild-type amino acid sequence of SEQ ID NO: 6; and wherein the amino acid L at position 411 of SEQ ID NO: 6 is substituted with A, F, H, I, Q, S, W, or Y; the amino acid Y at position 412 of SEQ ID NO: 6 is not substituted or substituted with A, C, D, F, G, H, I, K, L, M, N, or Q; and the amino acid P at position 413 of SEQ ID NO: 6 is not substituted or substituted with A, G, S, or T.

In accordance with some embodiments, the B-family DNA polymerase variant having deficient 3' to 5' exonuclease activity is derived from *Thermococcus litoralis* DNA polymerase (Vent) having a wild-type amino acid sequence of SEQ ID NO: 6; and wherein the amino acid L at position 411 of SEQ ID NO: 6 is substituted with A, F, H, I, Q, S, W, or Y; the amino acid Y at position 412 of SEQ ID NO: 6 is not substituted or substituted with A, C, D, F, G, H, I, K, L, M, N, or Q; the amino acid P at position 413 of SEQ ID NO: 6 is not substituted or substituted with A, G, S, or T; and the amino acid A at position 488 of SEQ ID NO: 6 is substituted with C, D, E, F, G, H, K, L, R, T, or Y.

In accordance with some embodiments, the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein the amino acid L at position 485 of SEQ ID NO: 7 is substituted with A, F, H, I, Q, S, W, or Y; the amino acid Y at position 486 of SEQ ID NO: 7 is not substituted or substituted with A, C, D, F, G, H, I, K, L, M, N, or Q; and the amino acid P at position 487 of SEQ ID NO: 7 is not substituted or substituted with A, G, S, or T.

In accordance with some embodiments, the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein the amino acid L at position 485 of SEQ ID NO: 7 is substituted with A, F, H, I, Q, S, W, or Y; the amino acid Y at position 486 of SEQ ID NO: 7 is not substituted or substituted with A, C, D, F, G, H, I, K, L, M, N, or Q; the amino acid P at position 487 of SEQ ID NO: 7 is not substituted or substituted with A, G, S, or T; and the amino acid A at position 565 of SEQ ID NO: 7 is substituted with C, D, E, F, G, H, K, L, R, T, or Y.

In accordance with some embodiments, the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein the amino acid M at position 426 of SEQ ID NO: 8 is substituted with A, F, H, I, Q, S, W, or Y; the amino acid Y at position 427 of SEQ ID NO: 8 is not substituted or substituted with A, C, D, F, G, H, I, K, L, M, N, or Q; and the amino acid P at position 428 of SEQ ID NO: 8 is not substituted or substituted with A, G, S, or T.

In accordance with some embodiments, the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein the amino acid M at position 426 of SEQ ID NO: 8 is substituted with A, F, H, I, Q, S, W, or Y; the amino acid Y at position 427 of SEQ ID NO: 8 is not substituted or substituted with A, C, D, F, G, H, I, K, L, M, N, or Q; the amino acid P at position 428 of SEQ ID NO: 8 is not substituted or substituted with A, G, S, or T; and the amino acid A at position 508 of SEQ ID NO: 8 is substituted with C, D, E, F, G, H, K, L, R, T, or Y.

In accordance with some embodiments, the B-family DNA polymerase variant having deficient 3' to 5' exonuclease activity is derived from *Sulfolobus solfataricus* DNA polymerase (S so) having a wild-type amino acid sequence of SEQ ID NO: 9; and wherein the amino acid L at position 518 of SEQ ID NO: 9 is substituted with A, F, H, I, Q, S, W, or Y; the amino acid Y at position 519 of SEQ ID NO: 9 is not substituted or substituted with A, C, D, F, G, H, I, K, L, M, N, or Q; and the amino acid P at position 520 of SEQ ID NO: 9 is not substituted or substituted with A, G, S, or T.

In accordance with some embodiments, the B-family DNA polymerase variant having deficient 3' to 5' exonuclease activity is derived from *Sulfolobus solfataricus* DNA polymerase (Sso) having a wild-type amino acid sequence of SEQ ID NO: 9; and wherein the amino acid L at position 518 of SEQ ID NO: 9 is substituted with A, F, H, I, Q, S, W, or Y; the amino acid Y at position 519 of SEQ ID NO: 9 is not substituted or substituted with A, C, D, F, G, H, I, K, L, M, N, or Q; the amino acid P at position 520 of SEQ ID NO: 9 is not substituted or substituted with A, G, S, or T; and the amino acid A at position 601 of SEQ ID NO: 9 is substituted with C, D, E, F, G, H, K, L, R, T, or Y.

In accordance with some embodiments, the B-family DNA polymerase variant exhibits activity of synthesizing nucleic acids in a template-independent manner by adding at least one nucleotide selected from the group of naturally occurring nucleotides, nucleotide analogues, or a mixture thereof, to an extendible initiator.

In certain embodiments, the extendible initiator comprises a single-stranded oligonucleotide initiator, a blunt ended double-stranded oligonucleotide initiator, or a mixture thereof. In certain embodiments, the extendible initiator is a free form nucleic acid and can be reacted in a liquid phase.

In certain embodiments, the extendible initiator is immobilized on a solid support, wherein the solid support comprises a particle, bead, slide, array surface, membrane, flow cell, well, microwell, nano-well, chamber, microfluidic chamber, channel, microfluidic channel, or any other surfaces.

In certain embodiments, the at least one nucleotide is linked with a detectable label, such as fluorophores, enzymes, radioactive phosphates, digoxygenin, or biotin.

In accordance with some embodiments, the B-family DNA polymerase variant exhibits the template-independent nucleic acid synthesis activity at reaction temperatures ranging from 10° C. to 100° C. For example, the reaction temperature is between 10° C. and 20° C., between 20° C. and 30° C., between 30° C. and 40° C., between 40° C. and 50° C., between 50° C. and 60° C., between 60° C. and 70° C., between 70° C. and 80° C., between 80° C. and 90° C., between 90° C. and 95° C., between 95° C. and 100° C., or any reaction temperatures within a range defined by an upper limit of 15° C., 20° C., 25° C., 30° C., 35° C., 37° C., 40° C., 45° C., 50° C., 55° C., 60° C., 65° C., 70° C., 75° C., 80° C., 85° C., 90° C., 95° C., or 100° C. and an lower limit of 10° C., 15° C., 20° C., 25° C., 30° C., 35° C., 37° C., 40° C., 45° C., 50° C., 55° C., 60° C., 65° C., 70° C., 75° C., 80° C., 85° C., 90° C., or 95° C.

Creation of Polymerase Variants

Various types of mutagenesis techniques are optionally used in the present disclosure to modify polymerases to create the variants of the subject application, for instance, using random or semi-random mutational approaches. In general, any available mutagenesis procedure can be used for making polymerase mutants. Such mutagenesis procedures optionally include selection of altered nucleic acids and polypeptides for one or more activity of interest. Procedures that can be used include, but are not limited to: the site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gaped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to skilled person.

Kit for Performing Template-Independent Nucleic Acid Synthesis Reaction

The present invention also provides a kit that includes the PolB variant described herein, for performing de novo enzymatic nucleic acid synthesis reaction, which comprises: a B-family DNA polymerase variant as described above, wherein the PolB variant exhibits activity of synthesizing nucleic acids in a template-independent manner by adding at least one nucleotide selected from the group of naturally occurring nucleotides, nucleotide analogues, or a mixture thereof, to an extendible initiator, thereby synthesizing a desired or predetermined nucleic acid sequence.

Optionally, other reagents such as buffers and solutions required for the PolB variant and nucleotide solution are also included. Instructions for use of the assembled or packaged components are also typically but not necessarily included.

Uses of B-Family DNA Polymerase Variant

In some embodiments, the PolB variants described herein can be used to add natural nucleotides or 3'-modified nucleotide analogues to the 3'-hydroxyl (3'-OH) terminus of a single-stranded or a blunt-end, duplex nucleic acids initiator in a template-independent synthesis manner to produce polynucleotides with desired or predetermined sequences.

In some embodiments, the PolB variants described herein can be used to add nucleotides or nucleotide analogues to the 3'-OH termini of arrays of clustered single-stranded or a blunt-end, duplex nucleic acids initiators, which are immobilized or physically confined, and separated on a solid support as described previously; and preferably, the solid support is made of glass and implemented in the form of silicon wafer. Thus, a multiplexing, parallel de novo nucleic acid synthesis can be performed to synthesize large numbers of various polynucleotides or nucleic acids with distinct sequences.

The PolB variant-based method of large-scale, parallel de novo enzymatic nucleic acid synthesis can drive down the overall costs of de novo nucleic acids synthesis, while shortening the time for manufacturing oligonucleotides, synthetic gene constructs, or genomes for emerging bio-economical applications, such as the nucleic acid-based molecular diagnostics, vaccine and pharmaceutical product development, genome editing, synthetic biology applications, and DNA-based digital data storage. In certain embodiments, the PolB variants described herein can be used to add natural nucleotides or 3'-modified nucleotide analogues to the 3'-OH terminus of the extendible initiator or polynucleotide chain in a template-independent synthesis manner to generate polynucleotides with desired sequences.

In certain embodiments, the PolB variants described herein can be used to incorporate the nucleotide conjugates (one of the types of nucleotide analogue defined previously) covalently linked with an enzyme, an antibody, a chemical moiety/group, such as a biotin, a desthiobiotin, or a fluorophore on the base, phosphate moiety, or pentose sugar of nucleotide, to the 3'-terminus of the nucleic acid initiator in a template-independent synthesis manner.

The incorporation of these nucleotide analogues into the nucleic acids by PolB variants during the nucleic acid synthesis concurrently add the desired component, such as an enzyme, an antibody, or a chemical moiety/group to the newly synthesized nucleic acids in a base-specific, site-specific, or sequence-specific manner. Common components used to label or generate nucleic acid probes and conjugates are known in the art, which include, but are not limited to, radiolabeled nucleotides and nucleotide analogues, modified linkers, such as a biotin, a thiol, an azido, or an amine group, fluorophores, enzymes, and antibodies.

Alternatively, in other embodiments, to label or generate nucleic acid probes, the post-synthetic modifications of nucleic acids can be achieved by covalently or non-covalently coupling with an enzyme, an antibody, a chemical moiety/group, or a fluorophore via a modified linker on the base, the phosphate moiety, or the pentose sugar of synthesis nucleotide. As a result, the desired component can be covalently or non-covalently associated with the specific base or connected to newly synthesized nucleic acids.

In some embodiments, the PolB variant-dependent incorporation of linker-modified nucleotide analogues may be used to facilitate the newly synthesized polynucleotides or nucleic acids to be attached, immobilized or physically confined on various solid surfaces, for broadening the application of de novo enzymatic nucleic acid synthesis. Retrospectively, in other embodiments, the newly synthesized sequence-specific nucleic acids with unique labels, tags, or fluorophores can be used in various nucleic acid-based molecular detections, which include, but are not limited to, the fluorescence in situ hybridization (FISH), TaqMan real-time PCR (RT-PCR), real-time fluorescence ligase chain reaction (RT-LCR), real-time fluorescence recombinase-polymerase amplification (RPA) assay, and real-time fluorescence loop-mediated isothermal amplification assay.

EXAMPLES

Example 1: Preparation of PolB Variants

The gene synthesis approach and mutagenesis technique are adapted to create exemplary PolB variants according to the properties of conserved/consensus amino acids in the conserved and semi-conserved regions of selective PolBs, which are disclosed herein. For instance, the well-known site-directed mutagenesis approach is conducted to change the amino acid residues in the motif Exo I, motif Exo II, motif Exo III, motif A, motif B, and motif C regions of an exemplary wild-type PolBs listed herein.

In some embodiments, the procedure for obtaining PolB variants is generally divided into three steps, including Step 1: Gene synthesis of wild-type PolB and its 3' to 5' exonuclease-deficient (Exo$^-$) mutant, Step 2: Construction of the specific PolB variant having the predetermined mutation(s) in the desired region, and Step 3: Expression and purification of wild-type PolB, Exo$^-$ mutant, and PolB variant. As described in more detail below, the techniques used in said procedure are well-known to those skilled in the art.

In Step 1, the codon-optimized gene fragment encoding the wild-type, intein-free PolB polymerase is synthesized by Genomics BioSci & Tech Co. (New Taipei City, Taiwan). The 3' to 5' exonuclease-deficient (designated as Exo$^-$) PolB polymerase is also provided by the same vendor. The superscript "exo$^-$" following an abbreviated name of any PolB listed herein means that the designated wild-type PolB has been modified to remove the intrinsic 3' to 5' exonuclease activity, which indicates said PolB is a 3' to 5' exonuclease-deficient PolB. Preferably, in the Examples of this disclosure, the Exo$^-$ means a PolB mutant carrying combinatory mutations at the positions corresponding to D354 of SEQ ID NO: 1, which is substituted with an alanine residue (D354A), and E356 of SEQ ID NO: 1, which is also substituted with an alanine residue (E356A), respectively.

In Step 2, the synthetic wild-type and Exo$^-$ PolB genes are respectively subcloned into the pET28b vector using the flanking NdeI and NotI restriction sites. The sequences of recombinant plasmids are confirmed by DNA sequencing. To create the polymerase variant at the desired motif region of the PolB Exo$^-$ protein backbone, the site-directed mutagenesis, is conducted. Briefly, the site-directed mutagenesis PCR is performed with the recombinant plasmids using the Q5 Site-directed Mutagenesis Kit from New England Biolabs (Ipswich, Mass.) to introduce the amino acid substitution. The products are first analyzed by 1% agarose gel to confirm the amplicon size and the rest of PCR reaction mixture is then treated with DpnI at 37° C. for an hour. The mixture is further incubated at 70° C. for 10 mins to inactivate the DpnI function. The DpnI-treated PCR reaction mixture is then purified by the Qiagen's QIAquick PCR Purification Kit (Whatman, Mass.). The purified DNA fragment is treated with the mixture of T4 PNK and T4 DNA ligase. The re-circularized PCR-amplified DNA is transformed back into the E. coli cells. The plasmid DNA was later extracted from the E. coli cells using the Qiagen Plasmid Mini Kit (Whatman, Mass.). The mutated sequences of the polymerase variants at the desired motif region, or regions, are confirmed by DNA sequencing.

In Step 3, E. coli Acella cells harboring the plasmid DNA carrying specific polymerase variant gene are grown in 2 L of LB medium supplemented with 0.5% glucose and 50 µg/ml carbenicillin at 37° C. When the cell density reaches an absorbance value at OD600 nm around 0.6~0.8, an 1 mM of isopropyl β-D-1-thiogalactopyranoside (IPTG) is added to induce protein expression. Cells are grown for additional 4 hours at 37° C. and then harvested by centrifugation at 4° C. for 10 min at 7,000×g. Cell pellets are resuspended with buffer A [50 mM Tris-HCl (pH 7.5), 300 mM NaCl, 0.5 mM EDTA, 1 mM DTT, 5% (v/v) glycerol] containing 1 mM benzamidine hydrochloride. Cell lysis is achieved by incubation with 50 mg lysozyme on ice for 1 hour followed by sonication. The cell lysate is clarified by centrifugation at 18,000×g for 25 min at 4° C. The clarified crude cell extract is incubated at 70° C. for 30 minutes and then cooled down at 4° C. The heat-treated cell extract is further clarified by centrifugation at 18,000×g for 25 minutes at 4° C. After centrifugation, the supernatant is diluted with buffer A without NaCl and loaded onto a HiTrap Heparin column (Cytiva Life Sciences, Marlborough, Mass., USA) pre-equilibrated in buffer A in the ÄKTA pure chromatography system (Cytiva Life Sciences, Marlborough, Mass., USA). The protein is eluted with the linear 100 mM to 1 M NaCl gradient using the buffer B [50 mM Tris-HCl (pH 8.0), 1 M NaCl, 0.5 mM EDTA, 1 mM DTT, 5% (v/v) glycerol]. Column fractions are analyzed by 10% SDS-PAGE. Fractions containing desired protein are pooled and dialyzed against the storage buffer [50 mM Tris-HCl (pH 7.5), 250 mM NaCl, 0.5 mM EDTA, 1 mM DTT, 5% (v/v) glycerol] at 4° C. overnight. The dialyzed protein fraction pool containing the target protein is concentrated using an Amicon filter unit (MW cut-off 50,000). The concentrated protein pool is aliquoted and stored at −20° C. Each mutant polymerase variant was purified with the same procedures as described above. The final protein concentration is determined by the Bradford reaction (Bradford, 1976) using the Bio-Rad Protein Assay (Hercules, Calif.) with bovine serum albumin as a standard.

Example 2: Template-Independent DNA Synthesis Assay

The PolB variants provided herein are tested for template-independent DNA synthesis approach. To further evaluate the activities (performance on incorporating naturally occurring nucleotide and nucleotide analogues) of the PolB variants, normal dNTPs or modified nucleotides and a single-stranded DNA initiator or a blunt-end duplex DNA initiator are used herein.

In this example, the following synthetic oligonucleotides are used to determine the template-independent DNA synthesis activity of PolB variants.

FAM-45-mer DNA initiator: 5'-CTCGGCCTGGCACAGGTCCGTTCAGTGCTGC-GGCGACCACCGAGG-3' (SEQ ID NO: 18). This single-stranded oligonucleotide is labeled with a fluorescent fluorescein amidite (FAM) dye at the 5'-end.

Blunt-end duplex DNA initiator: a duplex DNA composed of a 38-mer primer labeled with a fluorescent Cyanine5 (Cy5) dye at the 5'-end (Cy5-38-mer primer) and its complementary 38-mer oligonucleotide (complementary 38-mer DNA). The sequences are listed as below.

```
Cy5-38-mer primer:
                                  (SEQ ID NO: 19)
5'-GCTTGCACAAGTTCGTTCAATGATACGGCGACCACCGA-3'

Complementary 38-mer DNA:
                                 (SEQ ID NO.: 20)
5'-TCGGTGGTCGCCGTATCATTGAACGAACTTGTGCAAGC-3'
```

The blunt-end duplex DNA initiator is formed by annealing the Cy5-38-mer primer with the complementary 38-mer DNA at a molar ratio of 1:1.5 in the 1× TE buffer [10 mM Tris-HCl (pH 8.0) and 1 mM EDTA] containing 100 mM NaCl. The DNA annealing reaction is performed in the Bio-Rad Thermal Cycler (Hercules, Calif.) by first heating up the sample mixture to 98° C. for 3 minutes and then gradually cooling it down (5° C./30 seconds) to 4° C. The annealed product without overhang is used as the blunt-end duplex DNA initiator.

The template-independent DNA synthesis reaction is performed in the reaction mixtures (10 µl) containing 100 nM of the FAM-45-mer DNA initiator or the blunt-end duplex DNA initiator, 0.25 mM manganese chloride ($MnCl_2$), and 200 nM of selective PolB variants. The de novo enzymatic DNA synthesis reactions is initiated by the addition of 200 µM of canonical nucleotide mixtures (dNTPs) or nucleotide analogues (such as 3'-O-azidomethyl-dNTP and dye nucleotides). The reactions are allowed to proceed for a certain period (e.g., 5 minutes for conducting the Examples in the following context) and then terminated by adding 10 µl of 2× quench solution (95% de-ionized formamide and 25 mM EDTA) at a predetermined reaction temperature. The sample mixtures are denatured at 95° C. for 10 min and analyzed by 20% polyacrylamide gel electrophoresis containing 8M urea (Urea-PAGE). The de novo enzymatic DNA synthesis reaction products are then visualized by imaging the gel on the Amersham Typhoon Laser Scanner (Cytiva Life Sciences, Marlborough, Mass., USA).

Alternatively, the template-independent DNA synthesis assay is performed in the reaction mixture (10 µl) containing 50 nM of FAM-45-mer DNA initiator and 200 nM of terminal deoxynucleotidyl transferase (Tdt) obtained from New England BioLabs (Ipswich, Mass., USA) in the Tdt reaction buffer [50 mM potassium acetate, 20 mM Tris-acetate, 10 mM magnesium acetate (pH 7.9), and 0.25 mM $CoCl_2$]. The de novo enzymatic DNA synthesis reactions is initiated by adding 200 µM of dNTP mixture at various temperatures, ranging from 10° C., 20° C., 30° C., 35° C., 40° C., 45° C., 50° C., 55° C., 60° C., 70° C., 80° C. to 90° C., respectively. Each reaction is allowed to proceed for 30 minutes (or for a certain period such as 5 and 10 minutes) and then stopped by adding 10 µl of 2× quench solution (95% de-ionized formamide and 25 mM EDTA). The sample mixtures are denatured at 95° C. for 10 min and analyzed by 20% polyacrylamide gel electrophoresis containing 8M urea (Urea-PAGE). The de novo enzymatic DNA synthesis reaction products is then visualized by imaging the gel on the Amersham Typhoon Laser Scanner (Cytiva Life Sciences, Marlborough, Mass., USA).

Example 3: Template-Independent DNA Synthesis Activity of Exonuclease-Deficient PolB Variants In this example, the Tgo$^{exo-}$, Kod1$^{exo-}$, 9°N$^{exo-}$, Pfu$^{exo-}$, Vent$^{exo-}$, Mac$^{exo-}$, Pis$^{exo-}$, and Sso$^{exo-}$ were selected as exonuclease-deficient enzymes constructed as described in Example 1. For brevity, the Kod1$^{exo-}$, Vent$^{exo-}$, and Pfu$^{exo-}$ were used as exemplary exonuclease-deficient PolB variant for demonstrating the baseline of template-independent enzymatic DNA synthesis activity. The template-independent enzymatic DNA synthesis activity of commercially available Tdt was also evaluated. The procedures for evaluating the template-independent enzymatic DNA synthesis activity were performed as set forth in Example 2.

Figure 2A:
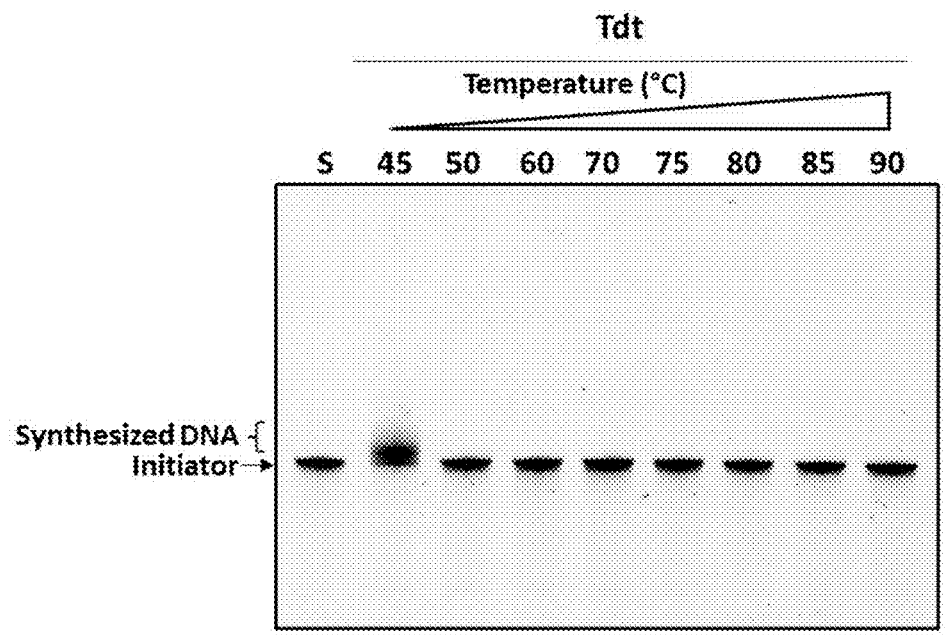
FIGS. 2A and 2B show the results of the reactions described in Example 3.
Figure 2B:
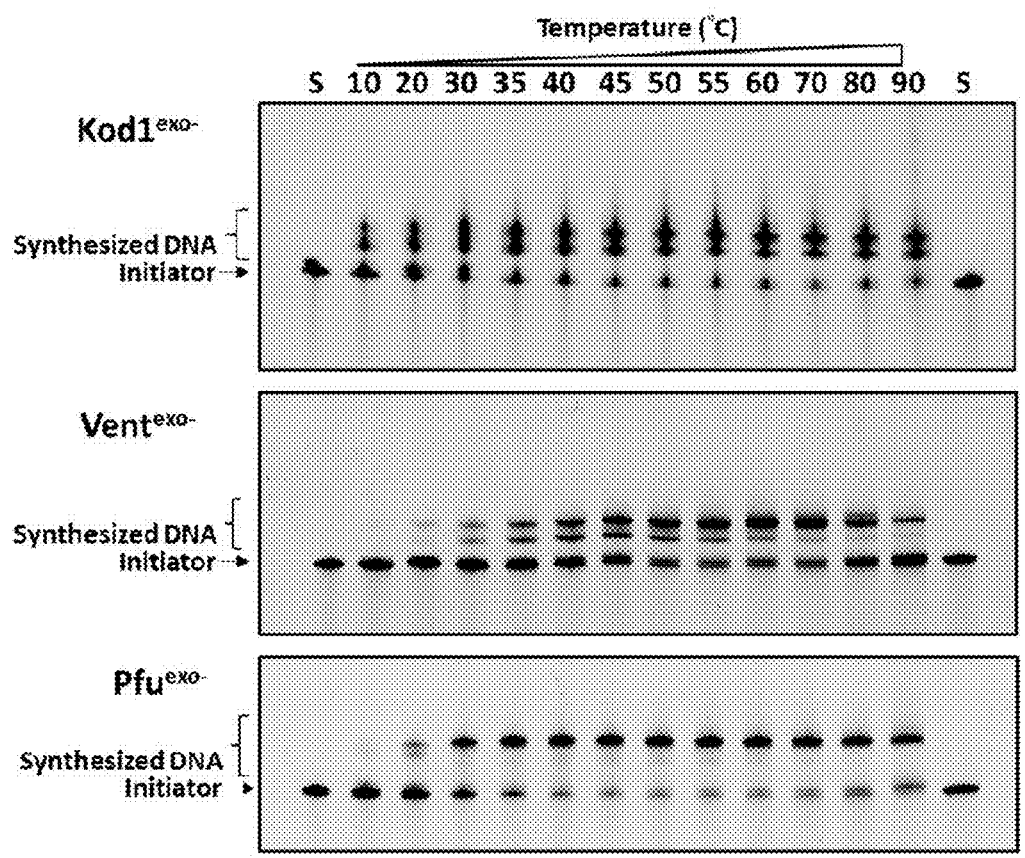

The assay results are shown in FIGS. 2A and 2B, where "S" stands for using the substrate (FAM-45-mer DNA initiator) as a blank (no enzyme) control. The results showed that the Kod1$^{exo-}$, Vent$^{exo-}$, and Pfu$^{exo-}$ each exerts the template-independent enzymatic DNA synthesis activity using single-strand DNA as the initiator at incremental reaction temperatures (FIG. 2B), while Tdt rapidly loses its activity when the reaction temperature is raised to around 45° C. (FIG. 2A). The results demonstrated that the exonuclease-deficient PolB variants possessed better thermotolerant properties for template-independent nucleic acid synthesis than that of the conventional Tdt enzyme.

Figure 3A:
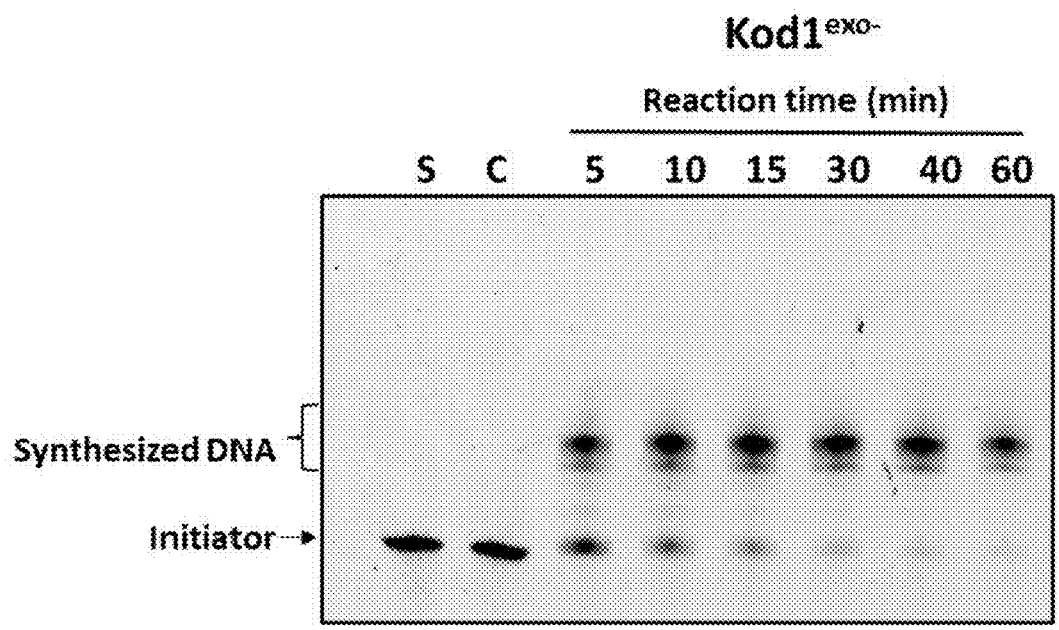
FIGS. 3A and 3B show the results of the reactions described in Example 4.
Figure 3B:
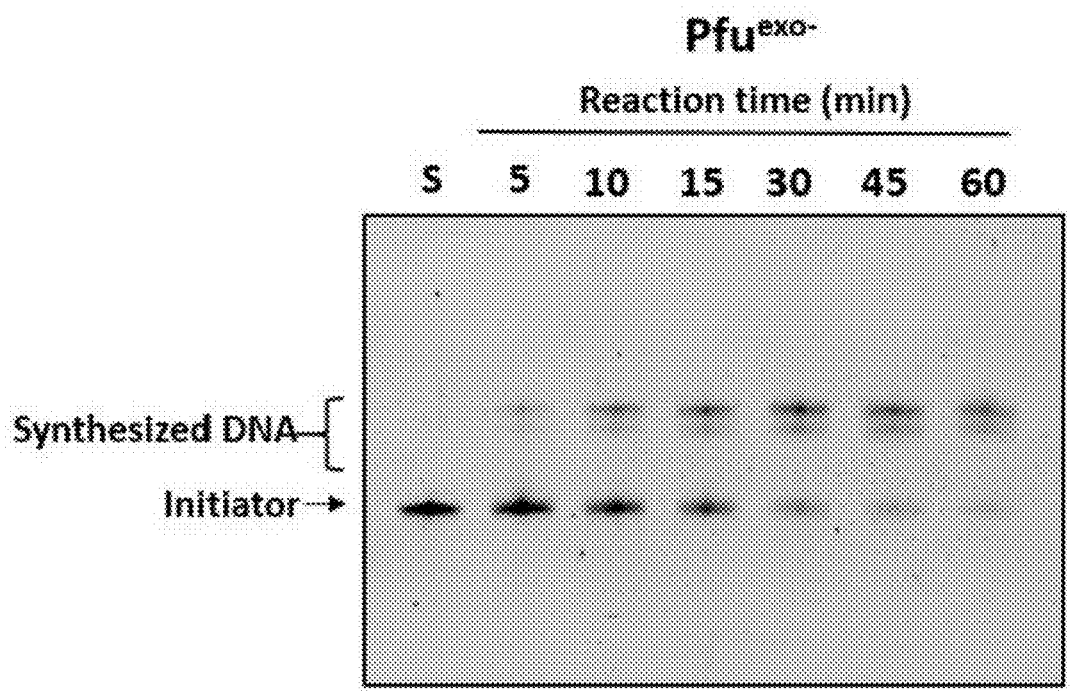

Example 4: Template-Independent DNA Synthesis Activity of Exonuclease-Deficient PolB B Variants In this example, the Kod1$^{exo-}$ and Pfu$^{exo-}$ as described in Example 3 were further used as exemplary exonuclease-deficient PolB variant for demonstrating the catalytic efficiency PolB variants. The catalytic efficiency was evaluated using the same activity assay as described above, and the DNA synthesis activity was monitored over a defined course of time (e.g., 60 minutes). The results are shown in FIGS. 3A and 3B. As shown in FIGS. 3A and 3B, where "S" stands for the substrate (FAM-45-mer DNA initiator) and serves as a blank DNA control; and "C" stands for the reaction without the addition of dNTPs as a negative control. The newly synthesized DNA was clearly observed after 5-minute reaction, indicating the enzymatic DNA synthesis reactions were efficient. In addition, it was observed that the amount of newly synthesized DNA product accumulated while the FAM-45-mer DNA initiator prominently diminished over time, indicating the enzymatic DNA synthesis reactions were completed within around 30 minutes. Based on these results, it can be concluded that the exonuclease-deficient PolB variants can effectively and efficiently perform a template-independent enzymatic DNA synthesis.

Example 5: Catalytic Activity of PolB Variants on Incorporating Canonical Nucleotides to the FAM-45-mer DNA Initiator Based on the improved template-independent DNA synthesis properties of exonuclease-deficient PolBs, the selected exonuclease-deficient PolBs (e.g., Tgo$^{exo-}$, Kod1$^{exo-}$, 9°N$^{exo-}$, Pfu$^{exo-}$, Vent$^{exo-}$, Mac$^{exo-}$, Pis$^{exo-}$, and Sso$^{exo-}$) were further modified to include more amino acid substitutions with different amino acids in varied conserved regions or motifs of each protein.

Example 5.1: Template-Independent DNA Synthesis Activity of Sso Variants

In this example, the PolB variants derived from Sso (SEQ ID NO: 9) is used exemplarily for evaluating the template-independent DNA synthesis activity of the PolB variant carrying combinatory substitutions in the motif Exo I, the motif A, and the motif B. Additionally, the U.S. Pat. No. 11,136,564B2 disclosed an AAI motif for substituting the conserved motif of some archaeal DNA polymerases to improve the incorporation of nucleotide analogues for template-dependent DNA synthesis reactions (i.e., DNA sequencing). The conserved motif is functionally and positionally equivalent to the L715, Y716, and P717 residing in the motif A of the consensus sequence (SEQ ID NO: 1) as defined herein. Therefore, the conserved motif is also functionally and positionally equivalent to the L518, Y519, and P520 residing in the motif A of the wild-type Sso (SEQ ID NO: 9). Thus, in view of the effects of the AAI motif on the template-directed nucleotide incorporation, the AAI motif substitution is equivalently included in this example for comparison.

Figure 4:
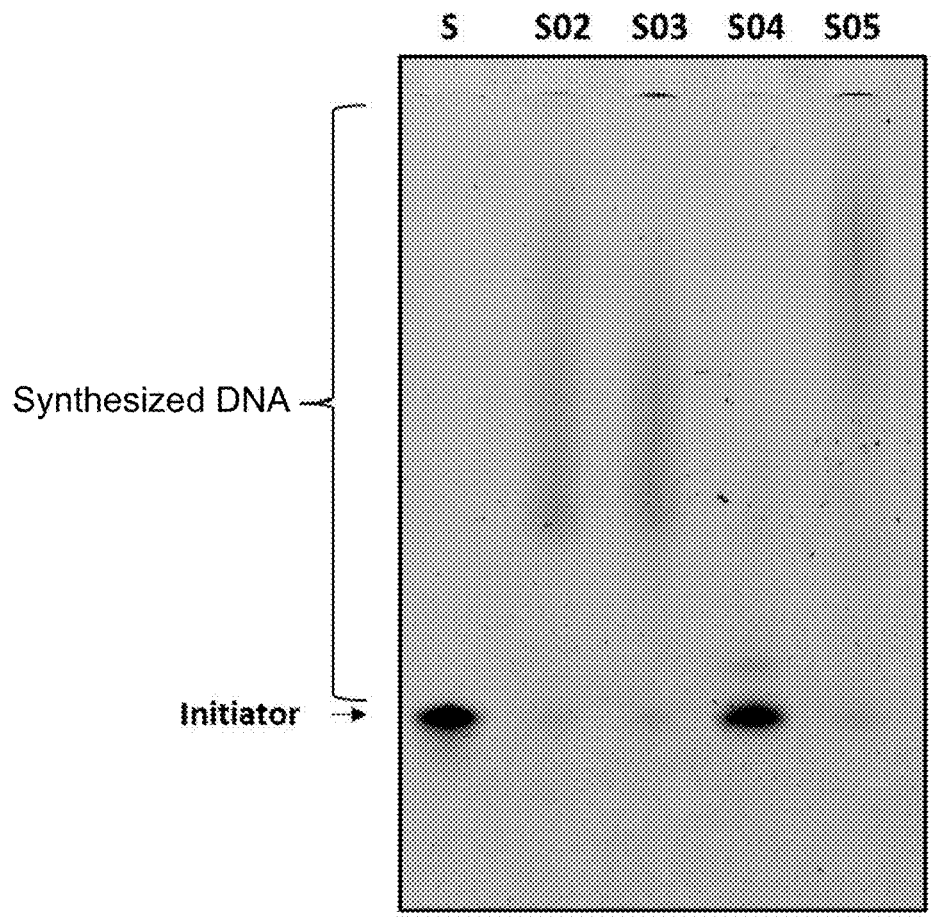
FIG. 4 shows the results of the reactions described in Example 5.1.

In this example, the variants modified from Sso$^{exo-}$ (S01) backbone exemplified are numbered and listed in Table 5.1. The template-independent enzymatic DNA synthesis activities of these Sso variants are evaluated using the same activity assay as described above. The results are shown in FIG. 4, where "S" stands for the substrate (FAM-45-mer DNA initiator) and serves as a blank DNA control. As shown in FIG. 4, the variant S02 carrying amino acid substitutions in the motif Exo I (D231A+E233A) and motif A (L518Y+Y519A+P520G) and variant S03 carrying amino acid substitutions in the motif Exo I (D231A+E233A) and motif B (A601L) both exerted prominent catalytic activity of template-independent DNA synthesis; and most of the initiator (>95%) substrate was reacted to yield a great quantity of newly synthesized DNA products. Moreover, the variant S05 carrying combinatory amino acid substitutions in the motif Exo I (D231A+E233A), motif A (L518Y+Y519A+P520G), and motif B (A601L) further enhanced the said catalytic activity and produced the longer length of newly synthesized DNA products as compared to the variants S02 and S03. However, the variant S04 carrying combinatory amino acid substitutions in the motif Exo I (D231A+E233A), motif A (L518A+Y519A+P520I) and motif B (A601L) showed a marginal activity.

TABLE 5.1

List of amino acid substitutions in the PolB variants derived from Sso.

| Type of PolB Enzyme | Variant No. | Modification Substitutions |
|---|---|---|
| Sso | S01 | Exo⁻(D231A + E233A) |
|  | S02 | D231A + E233A + L518Y + Y519A + P520G |
|  | S03 | D231A + E233A + A601L |
|  | S04 | D231A + E233A + L518A + Y519A + P520I + A601L |
|  | S05 | D231A + E233A + L518Y + Y519A + P520G + A601L |

Example 5.2: Template-Independent DNA Synthesis Activity of Vent Variants

In this example, the PolB variants derived from Vent (SEQ ID NO: 6) is used exemplarily for evaluating the template-independent DNA synthesis activity of the PolB variant carrying combinatory substitutions in the motif Exo I, the motif A, and the motif B.

Figure 5A:
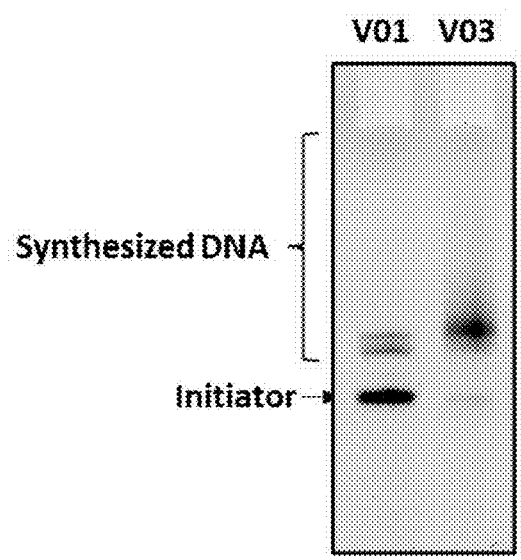
FIGS. 5A, 5B, 5C, and 5D show the results of the reactions described in Example 5.2.
Figure 5B:
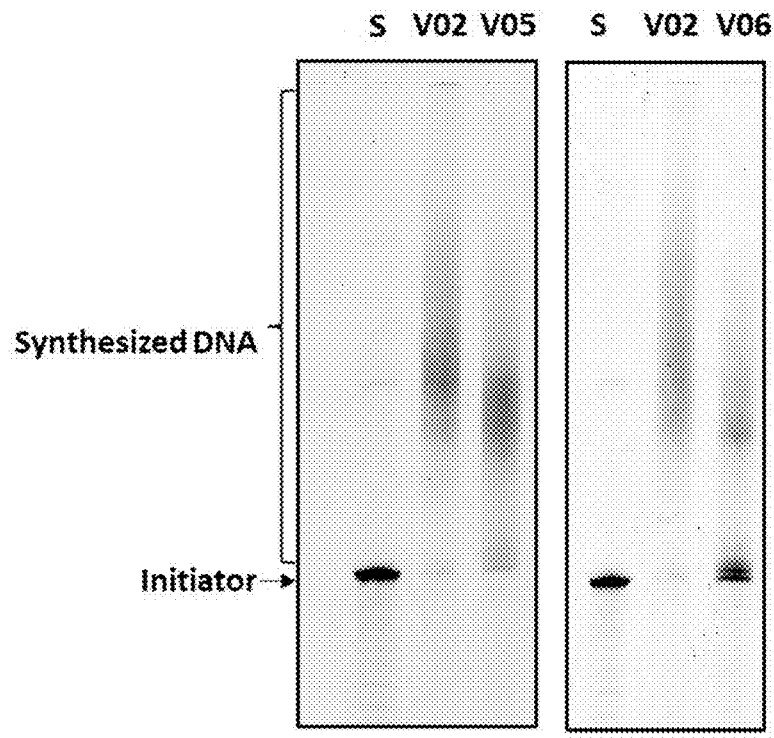
Figure 5C:
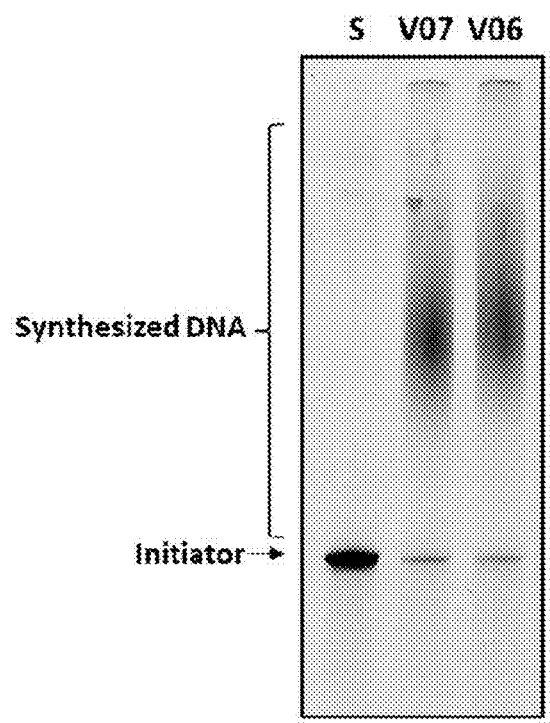
Figure 5D:
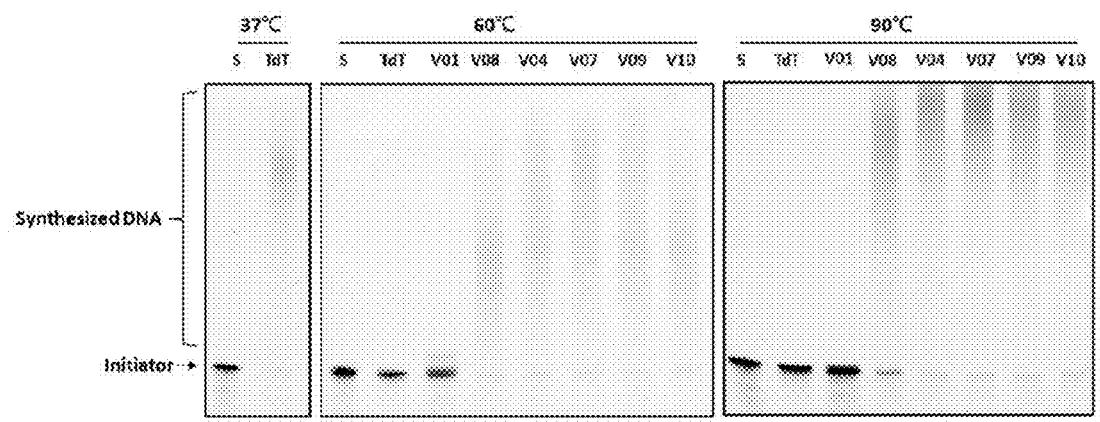

In this example, the variants modified from Vent$^{exo-}$ (V01) backbone exemplified are numbered and listed in Table 5.2. The template-independent enzymatic DNA synthesis activities of these Vent variants are evaluated using the same activity assay as described above. The results are shown in FIGS. 5A, 5B, 5C and 5D, where "S" stands for the substrate (FAM-45-mer DNA initiator) and serves as a blank DNA control. As shown in FIG. 5A, the variant V01 carrying amino acid substitutions in the motif Exo I (D141A+E143A) exerted baseline catalytic activity of template-independent enzymatic DNA synthesis at the reaction temperature of 55° C.; and the variant V03 carrying amino acid substitutions in the motif Exo I (D141A+E143A) and motif B (A488L) exerted an improved DNA synthesis activity as compared to variant V01. Furthermore, as shown in FIG. 5B, the variants V02, V05, and V06 carrying amino acid substitutions in the motif Exo I and motif A (detail substitutions are shown in Table 5.2) also exhibited a robust DNA synthesis activity at the hyperthermal reaction temperature of 70° C. Moreover, as shown in FIG. 5C, the variant V06 and the variant V07 carrying combinatory amino acid substitutions in the motif Exo I, motif A and motif B (detail amino acid substitutions are shown in Table 5.2) also exhibited significant DNA synthesis activity at the hyperthermal reaction temperature of 70° C. Additionally, the variants V08, V09, and V10 (detail amino acid substitutions are shown in Table 5.2) carrying combinatory amino acid substitutions in the motif Exo I, motif A and motif B were also exemplified in this example to demonstrate functional substitutions in the motif Exo I, motif A and motif B as compared to the control enzyme (Tdt). As shown in FIG. 5D, the variants having combinatory substitutions in both motif A and motif B, such as V04, V07, V08, V09, and V10, exhibit superior catalytic activity at wide hyperthermal reaction temperatures (i.e., 60° C. to 90° C.).

TABLE 5.2

List of amino acid substitutions in the PolB variants derived from Vent.

| Type of PolB Enzyme | Variant No. | Modification Substitutions |
|---|---|---|
| Vent | V01 | Exo$^-$(D141A + E143A) |
|  | V02 | D141A + E143A + L411Y + Y412A + P413G |
|  | V03 | D141A + E143A + A488L |
|  | V04 | D141A + E143A + L411Y + Y412A + P413G + A488L |
|  | V05 | D141A + E143A + L411C + Y412A + P413G |
|  | V06 | D141A + E143A + L411V + Y412A + P413G |
|  | V07 | D141A + E143A + L411Y + Y412A + A488L |
|  | V08 | D141A + E143A + L411Q + Y412A + P413G + A488L |
|  | V09 | D141A + E143A + L411Y + Y412A + P413G + A488E |
|  | V10 | D141A + E143A + L411Y + Y412A + P413G + A488F |

Example 5.3: Template-Independent DNA Synthesis Activity of 9°N Variants

In this example, the PolB variants derived from 9°N (SEQ ID NO: 4) is used exemplarily for evaluating the template-independent DNA synthesis activity of the PolB variant carrying combinatory substitutions in the motif Exo I and the motif A.

Figure 6:
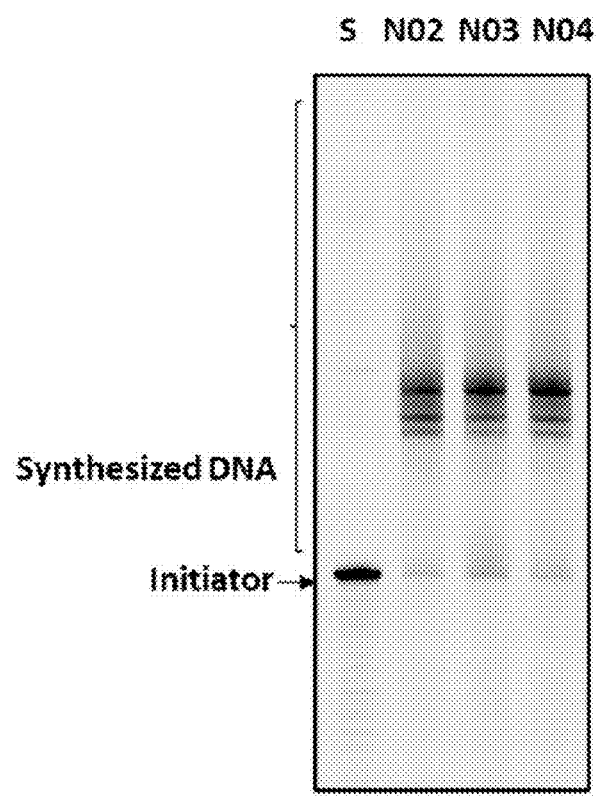
FIG. 6 shows the results of the reactions described in Example 5.3.

Similarly, the variants modified from 9°N$^{exo-}$ (N01) backbone exemplified are numbered and listed in Table 5.3. The template-independent DNA synthesis activities of these 9°N variants are evaluated using the same activity assay as described above. The results are shown in FIG. 6, where "S" stands for the substrate (FAM-45-mer DNA initiator) and serves as a blank DNA control. As shown in FIG. 6, the variants N02, N03 and N04 carrying amino acid substitutions in the motif Exo I (D141A+E143A) and motif A (detail amino acid substitutions are shown in Table 5.3) exerted robust DNA synthesis activity at the hyperthermal reaction temperature of 70° C.

TABLE 5.3

List of amino acid substitutions in the PolB variants derived from 9° N.

| Type of PolB Enzyme | Variant No. | Modification Substitutions |
|---|---|---|
| 9° N | N01 | Exo$^-$(D141A + E143A) |
|  | N02 | D141A + E143A + L408Y + Y409A + P410G |
|  | N03 | D141A + E143A + L408Y + Y409A + P410T |
|  | N04 | D141A + E143A + L408Y + Y409A + P410V |

Example 5.4: Template-Independent DNA Synthesis Activity of Kod1 Variants

In this example, the PolB variants derived from Kod1 (SEQ ID NO: 3) is used exemplarily for evaluating the template-independent DNA synthesis activity of the PolB variant carrying combinatory substitutions in the motif Exo I, the motif A, and the motif B. Additionally, as the rationale described previously in Example 5.1, the AAI motif substitution is also functionally and positionally equivalent to the conserved motif of L715, Y716, and P717 residing in the motif A of the consensus sequence (SEQ ID NO: 1). Therefore, the conserved motif is also functionally and positionally equivalent to the L408, Y409, and P410 residing in the motif A of the wild-type Kod1 (SEQ ID NO: 3); and the AAI motif substitution is equivalently included in this example for comparison.

Figure 7A:
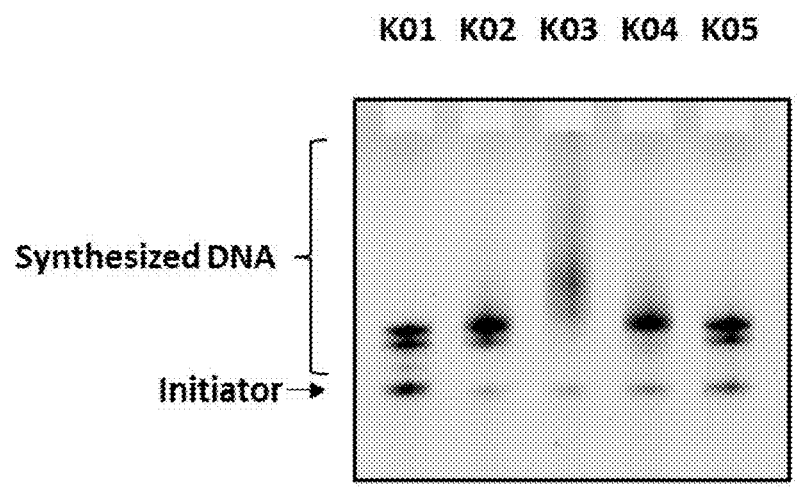
FIGS. 7A and 7B show the results of the reactions described in Example 5.4.
Figure 7B:
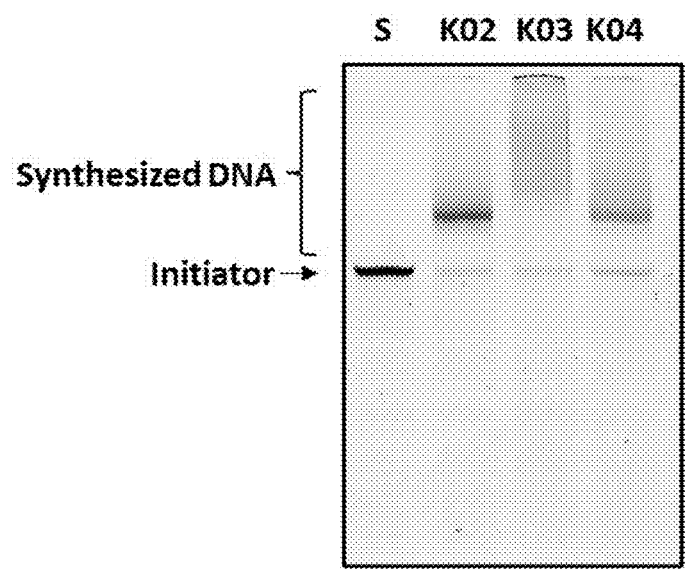

Similarly, the exemplified variants modified from Kod1$^{exo-}$ (K01) backbone are numbered and listed in Table 5.4. The template-independent enzymatic DNA synthesis activities of these Kod1 variants are evaluated using the same activity assay as described above. The results are shown in FIG. 7A (the synthesis reactions were performed at 55° C.) and 7B (reactions performed at 70° C.). As shown in FIG. 7A, the variant K02, which carries amino acid substitutions in the motif Exo I (D141A+E143A) and motif B (A485L) and the variant K05, which carries amino acid substitutions in the motif Exo I (D141A+E143A) and motif A (L408Y+Y409A+P410G) both exerted a template-independent DNA synthesis activity; and the variant K03 carrying combinatory amino acid substitutions in motif Exo I (D141A+E143A), motif A (L408Y+Y409A+P410G), and motif B (A485L) exhibited an improved DNA synthesis activity as compared to the variants K02 and K05. The variant K04 carrying combinatory amino acid substitutions in the motif Exo I (D141A+E143A), motif A (L408A+Y409A+P410I), and motif B (A485L) showed a lower DNA synthesis activity as compared to the variants K02, K03 and K05. Additionally, as shown in FIG. 7B, where "S" stands for the substrate (FAM-45-mer DNA initiator) and serves as a blank DNA control, the comparable results for these variants were observed even at the hyperthermal reaction temperature of 70° C.

TABLE 5.4

List of amino acid substitutions in the PolB variants derived from Kod1.

| Type of PolB Enzyme | Variant No. | Modification Substitutions |
|---|---|---|
| Kod1 | K01 | Exo⁻(D141A + E143A) |
|  | K02 | D141A + E143A + A485L |
|  | K03 | D141A + E143A + L408Y + Y409A + P410G + A485L |
|  | K04 | D141A + E143A + L408A + Y409A + P410I + A485L |
|  | K05 | D141A + E143A + L408Y + Y409A + P410G |

Example 5.5: Template-Independent DNA Synthesis Activity of Pfu Variants

In this example, the PolB variants derived from Pfu (SEQ ID NO: 5) is used exemplarily for evaluating the template-independent DNA synthesis activity of the PolB variant carrying combinatory substitutions in the motif Exo I, the motif A, and the motif B. Likewise, as described previously in Example 5.1, the AAI motif substitution is also functionally and positionally equivalent to the conserved motif of L715, Y716, and P717 residing in the motif A of the consensus sequence (SEQ ID NO: 1). Therefore, the conserved motif is also functionally and positionally equivalent to the L409, Y410, and P411 residing in the motif A of the wild-type Pfu (SEQ ID NO: 5); and the AAI motif substitution is equivalently included in this example for comparison.

Figure 8:
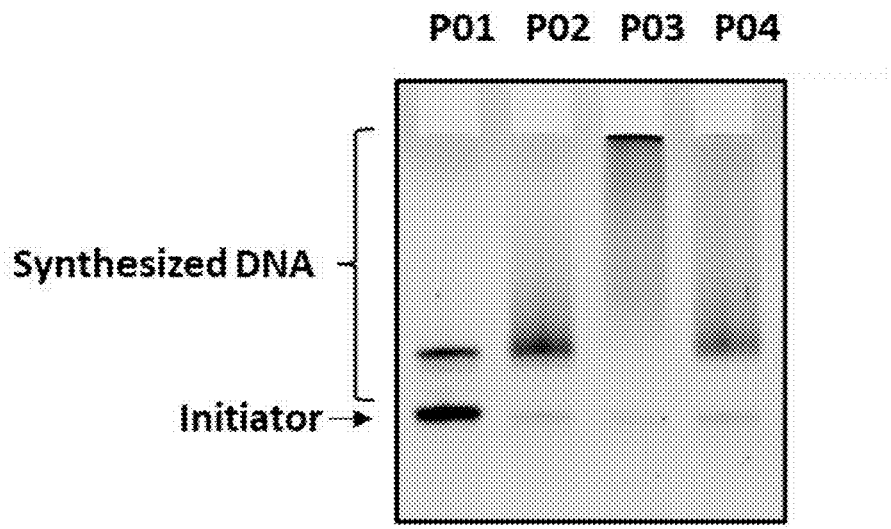
FIG. 8 shows the results of the reactions described in Example 5.5.

Similarly, the variants modified from Pfu$^{exo-}$ (P01) backbone exemplified are numbered and listed in Table 5.5. The template-independent enzymatic DNA synthesis activities of these Pfu variants are evaluated at the reaction temperature of 55° C. using the same activity assay as described above. The results are shown in FIG. 8. As shown in FIG. 8, the variant P02 carrying amino acid substitutions in the motif Exo I (D141A+E143A) and motif B (A486L) exerted a template-independent DNA synthesis activity. Furthermore, the variant P03 carrying combinatory amino acid substitutions in motif Exo I (D141A+E143A), motif A (L409Y+Y410A+P411G), and motif B (A486L) exhibited an improved DNA synthesis activity as compared to the variants P02 and P04. The variant P04 carrying combinatory amino acid substitutions in the motif Exo I (D141A+E143A), motif A (L409A+Y410A+P411I; AAI motif), and motif B (A486L) shows a lower DNA synthesis activity as compared to the variants P02 and P03.

TABLE 5.5

List of Amino Acid Substitutions in the PolB variants derived from Pfu.

| Type of PolB Enzyme | Variant No. | Modification Substitutions |
|---|---|---|
| Pfu | P01 | Exo⁻(D141A + E143A) |
|  | P02 | D141A + E143A + A486L |
|  | P03 | D141A + E143A + L409Y + Y410A + P411G + A486L |
|  | P04 | D141A + E143A + L409A + Y410A + P411I + A486L |

Example 5.6: Summary of Template-Independent DNA Synthesis Activity of PolB Variants In view of above Examples and other comparable template-independent DNA synthesis activity of various PolB variants (data not shown), these results indicate that the amino acid substitutions as provided herein are crucial for conferring or improving the template-independent DNA synthesis activities of the PolB variants.

The functionally or positionally substitutions residing in the motif A and motif B of selected PolB variants are summarized and listed in Table 5.6.

TABLE 5.6

List of amino acid substitutions in the exemplary PolB variants

| Type of PolB Enzymes | SEQ ID NO | Equivalent substitutions in the motif A and/or motif B corresponding to the consensus sequence (SEQ ID NO: 1) | | | |
|---|---|---|---|---|---|
|  |  | Position 715 (motif A) | Position 716 (motif A) | Position 717 (motif A) | Position 854 (motif B) |
| Tgo | 2 | L408A, L408F, L408H, L408I, L408Q, L408S, L408W, L408Y | Y409A, Y409C, Y409D, Y409F, Y409G, Y409H, Y409I, Y409K, Y409L, Y409M, Y409N, Y409Q | P410A, P410G, P410S, P410T | A485C, A485D, A485E, A485F, A485H, A485G, A485L, A485R, A485T, A485K, A485Y |

TABLE 5.6-continued

List of amino acid substitutions in the exemplary PolB variants

| Type of PolB Enzymes | SEQ ID NO | Equivalent substitutions in the motif A and/or motif B corresponding to the consensus sequence (SEQ ID NO: 1) | | | |
|---|---|---|---|---|---|
| | | Position 715 (motif A) | Position 716 (motif A) | Position 717 (motif A) | Position 854 (motif B) |
| Kod1 | 3 | L408A, L408F, L408H, L408I, L408Q, L408S, L408W, L408Y | Y409A, Y409C, Y409D, Y409F, Y409G, Y409H, Y409I, Y409K, Y409L, Y409M, Y409N, Y409Q | P410A, P410G, P410S, P410T | A485C, A485D, A485E, A485F, A485H, A485G, A485L, A485R, A485T, A485K, A485Y |
| 9° N | 4 | L408A, L408F, L408H, L408I, L408Q, L408S, L408W, L408Y | Y409A, Y409C, Y409D, Y409F, Y409G, Y409H, Y409I, Y409K, Y409L, Y409M, Y409N, Y409Q | P410A, P410G, P410S, P410T | A485C, A485D, A485E, A485F, A485H, A485G, A485L, A485R, A485T, A485K, A485Y |
| Pfu | 5 | L409A, L409F, L409H, L409I, L409Q, L409S, L409W, L409Y | Y410A, Y410C, Y410D, Y410F, Y410G, Y410H, Y410I, Y410K, Y410L, Y410M, Y410N, Y410Q | P411A, P411G, P411S, P411T | A486C, A486D, A486E, A486F, A486H, A486G, A486L, A486R, A486T, A486K, A486Y |
| Vent | 6 | L411A, L411F, L411H, L411I, L411Q, L411S, L411W, L411Y | Y412A, Y412C, Y412D, Y412F, Y412G, Y412H, Y412I, Y412K, Y412L, Y412M, Y412N, Y412Q | P413A, P413G, P413S, P413T | A488C, A488D, A488E, A488F, A488H, A488G, A488L, A488R, A488T, A488K, A488Y |
| Mac | 7 | L485A, L485F, L485H, L485I, L485Q, L485S, L485W, L485Y | Y486A, Y486C, Y486D, Y486F, Y486G, Y486H, Y486I, Y486K, Y486L, Y486M, Y486N, Y486Q | P487A, P487G, P487S, P487T | A565C, A565D, A565E, A565F, A565H, A565G, A565L, A565R, A565T, A565K, A565Y |
| Pis | 8 | M426A, M426F, M426H, M426I, M426Q, M426S, M426W, M426Y | Y427A, Y427C, Y427D, Y427F, Y427G, Y427H, Y427I, Y427K, Y427L, Y427M, Y427N, Y427Q | P428A, P428G, P428S, P428T | A508C, A508D, A508E, A508F, A508H, A508G, A508L, A508R, A508T, A508K, A508Y |
| Sso | 9 | L518A, L518F, L518H, L518I, L518Q, L518S, L518W, L518Y | Y519A, Y519C, Y519D, Y519F, Y519G, Y519H, Y519I, Y519K, Y519L, Y519M, Y519N, Y519Q | P520A, P520G, P520S, P520T | A601C, A601D, A601E, A601F, A601H, A601G, A601L, A601R, A601T, A601K, A601Y |

Example 6: Template-Independent DNA Synthesis Activity of PolB Variants on the Blunt-End Duplex DNA Initiator in the Presence of Canonical Nucleotides Based on the improved template-independent DNA synthesis properties of exonuclease-deficient PolBs, the selected exonuclease-deficient PolBs (e.g., Tgo$^{exo-}$, Kod1$^{exo-}$, 9°N$^{exo-}$, Pfu$^{exo-}$, Vent$^{exo-}$, Mac$^{exo-}$, Pis$^{exo-}$, and Sso$^{exo-}$) were further modified to include additional amino acid substitutions in varied regions of the protein.

Figure 9:
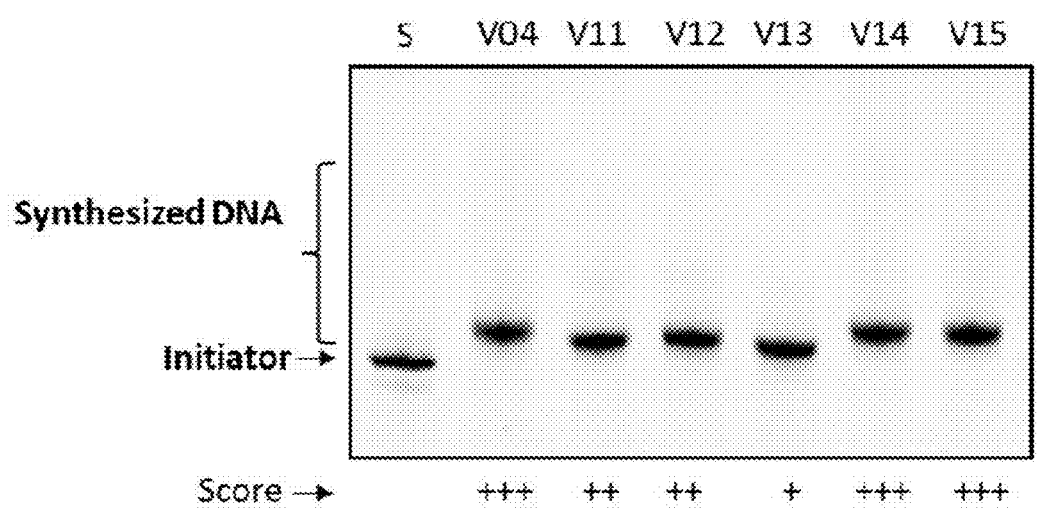
FIG. 9 shows the results of the reactions described in Example 6.

For the sake of brevity, in this Example, only the variants modified from Vent$^{exo-}$ (V01) backbone are selected and exemplified. The template-independent DNA synthesis activities of these Vent variants to extend the blunt-end duplex DNA initiator were evaluated using the same activity assay as described above. Only the exemplary results for the representative Vent variants are shown (FIG. 9). The list of these variants and their corresponding amino acid substitutions are listed in Table 6.1. The result of gel images for variants V04 and V11-V15 are showed in FIG. 9. As shown in FIG. 9, the "S" stands for the substrate (blunt-end duplex DNA initiator) and serves as a blank DNA control, which is also used as a baseline for scoring relative DNA synthesis activity of each variant as described in more details below.

TABLE 6.1

List of amino acid substitutions in the PolB variants derived from Vent.

| Type of PolB Enzyme | Variant No. | Modification Substitutions |
|---|---|---|
| Vent | V04 | D141A + E143A + L411Y + Y412A + P413G + A488L |
| | V11 | D141A + E143A + L411Y + Y412C + P413G + A488L |
| | V12 | D141A + E143A + L411Y + Y412D + P413G + A488L |
| | V13 | D141A + E143A + L411Y + Y412E + P413G + A488L |
| | V14 | D141A + E143A + L411Y + Y412F + P413G + A488L |

TABLE 6.1-continued

List of amino acid substitutions in
the PolB variants derived from Vent.

| Type of PolB Enzyme | Variant No. | Modification Substitutions |
|---|---|---|
| | V15 | D141A + E143A + L411Y + Y412G + P413G + A488L |

The relative template-independent DNA synthesis activity of each variant is scored and represented by the number of symbol "+". The overall activity score for each variant is divided into 4 distinct levels: 1) the "+++" indicates that the initiator is completely converted to various lengths of newly synthesized DNA as compared to the band intensity and position of the substrate control. Hence, the variant is considered to possess an 100% of DNA synthesis activity; 2) the "++" indicates that the initiator is converted around 50% to 100% to various lengths of newly synthesized DNA as compared to the band intensity and position of the substrate control. Hence, the variant is considered to possess a 50% to an 100% of DNA synthesis activity; 3) the "+" indicates that the initiator is converted around 10% to 50% to various lengths of newly synthesized DNA as compared to the band intensity and position of the substrate control. Hence, the variant is considered to possess a 10% to 50% of DNA synthesis activity; and 4) the "+/−" indicates that the initiator is less than 10% converted to various lengths of newly synthesized DNA as compared to the band intensity and position of the substrate control. Therefore, the variant is considered to possess <10% of DNA synthesis activity.

Based on the criteria described above, the activity scoring results of each functional/selected Vent variants are tabulated in Table 6.2.

TABLE 6.2

List of amino acid substitutions and the relative template-independent
DNA synthesis activity scoring of PolB variants derived from Vent
on blunt-end duplex DNA initiator in the presence of normal dNTPs.

| Variant No. | Residues and Amino Acid Substitutions | Activity score |
|---|---|---|
| V04 | D141A + E143A + L411Y + Y412A + P413G + A488L | +++ |
| V07 | D141A + E143A + L411Y + Y412A + A488L | +++ |
| V08 | D141A + E143A + L411Q + Y412A + P413G + A488L | +++ |
| V11 | D141A + E143A + L411Y + Y412C + P413G + A488L | ++ |
| V12 | D141A + E143A + L411Y + Y412D + P413G + A488L | ++ |
| V13 | D141A + E143A + L411Y + Y412E + P413G + A488L | + |
| V14 | D141A + E143A + L411Y + Y412F + P413G + A488L | +++ |
| V15 | D141A + E143A + L411Y + Y412G + P413G + A488L | +++ |
| V16 | D141A + E143A + L411C + Y412A + P413G + A488L | +++ |
| V17 | D141A + E143A + L411A + Y412A + P413G + A488L | +++ |
| V18 | D141A + E143A + L411F + Y412A + P413G + A488L | +++ |
| V19 | D141A + E143A + L411H + Y412A + P413G + A488L | +++ |
| V20 | D141A + E143A + L411I + Y412A + P413G + A488L | +/− |
| V21 | D141A + E143A + L411S + Y412A + P413G + A488L | +++ |
| V22 | D141A + E143A + L411T + Y412A + P413G + A488L | +++ |
| V23 | D141A + E143A + L411W + Y412A + P413G + A488L | +++ |
| V24 | D141A + E143A + L411Y + Y412H + P413G + A488L | +++ |
| V25 | D141A + E143A + L411Y + Y412I + P413G + A488L | +++ |
| V26 | D141A + E143A + L411Y + Y412K + P413G + A488L | +++ |
| V27 | D141A + E143A + L411Y + Y412L + P413G + A488L | +++ |
| V28 | D141A + E143A + L411Y + Y412M + P413G + A488L | +++ |
| V29 | D141A + E143A + L411Y + Y412N + P413G + A488L | +++ |
| V30 | D141A + E143A + L411Y + Y412Q + P413G + A488L | + |
| V31 | D141A + E143A + L411Y + Y412R + P413G + A488L | + |
| V32 | D141A + E143A + L411Y + Y412S + P413G + A488L | +++ |
| V33 | D141A + E143A + L411Y + Y412T + P413G + A488L | +++ |
| V34 | D141A + E143A + L411Y + Y412V + P413G + A488L | +++ |
| V35 | D141A + E143A + L411Y + Y412W + P413G + A488L | +++ |
| V36 | D141A + E143A + L411Y + P413G + A488L | +++ |
| V37 | D141A + E143A + L411Y + Y412A + P413A + A488L | +++ |
| V38 | D141A + E143A + L411Y + Y412A + P413C + A488L | +++ |
| V39 | D141A + E143A + L411Y + Y412A + P413D + A488L | +++ |
| V40 | D141A + E143A + L411Y + Y412A + P413E + A488L | +++ |
| V41 | D141A + E143A + L411Y + Y412A + P413F + A488L | +++ |
| V42 | D141A + E143A + L411Y + Y412A + P413H + A488L | +++ |
| V43 | D141A + E143A + L411Y + Y412A + P413I + A488L | +++ |
| V44 | D141A + E143A + L411Y + Y412A + P413K + A488L | +++ |
| V45 | D141A + E143A + L411Y + Y412A + P413L + A488L | +++ |
| V46 | D141A + E143A + L411Y + Y412A + P413M + A488L | +++ |
| V47 | D141A + E143A + L411Y + Y412A + P413N + A488L | +++ |
| V48 | D141A + E143A + L411Y + Y412A + P413Q + A488L | ++ |
| V49 | D141A + E143A + L411Y + Y412A + P413R + A488L | + |
| V50 | D141A + E143A + L411Y + Y412A + P413S + A488L | ++ |
| V51 | D141A + E143A + L411Y + Y412A + P413T + A488L | ++ |
| V52 | D141A + E143A + L411Y + Y412A + P413V + A488L | +++ |
| V53 | D141A + E143A + L411Y + Y412A + P413W + A488L | +++ |
| V54 | D141A + E143A + L411Y + Y412A + P413Y + A488L | +++ |

Example 7: Template-Independent DNA Synthesis Activity of PolB Variants on FAM-45-mer DNA Initiator in the Presence of Nucleotide Analogues (3'-O-azidomethyl-dNTPs)

Based on the improved template-independent DNA synthesis properties of exonuclease-deficient PolBs, the selected exonuclease-deficient PolBs (e.g., $Tgo^{exo-}$, $Kod1^{exo-}$, $9°N^{exo-}$, $Pfu^{exo-}$, $Vent^{exo-}$, $Mac^{exo-}$, $Pis^{exo-}$, and $Sso^{exo-}$) were further modified to include more additional amino acid substitutions in varied protein regions. In this example, exemplary nucleotide analogues 3'-O-azidomethyl-dNTPs (3'-O-AZ-dNTPs), which are well-known reversible terminator nucleotides in the DNA sequencing-by-synthesis chemistry, are used to demonstrate the ability of the PolB variants to utilize non-canonical nucleotides to perform the template-independent nucleic acid synthesis.

Example 7.1: Template-Independent DNA Synthesis Activity of 9°N Variants

For the sake of brevity, in this Example, the variants modified from $9°N^{exo-}$ (N01) backbone are selected and exemplified. The template-independent DNA synthesis activities of these 9°N variants to extend the FAM-45-mer DNA initiator in the presence of 3'-O-AZ-dCTP are evaluated using the same activity assay as described above. The 9°N derived variants are listed in Table 7.1. Moreover, according to the relative DNA synthesis activity scoring criteria as described in Example 6, the scoring results of each 9°N variants are also illustrated side by side in FIG. 10, where "S" stands for the substrate (FAM-45-mer DNA initiator) and serves as a blank DNA control.

Figure 10:
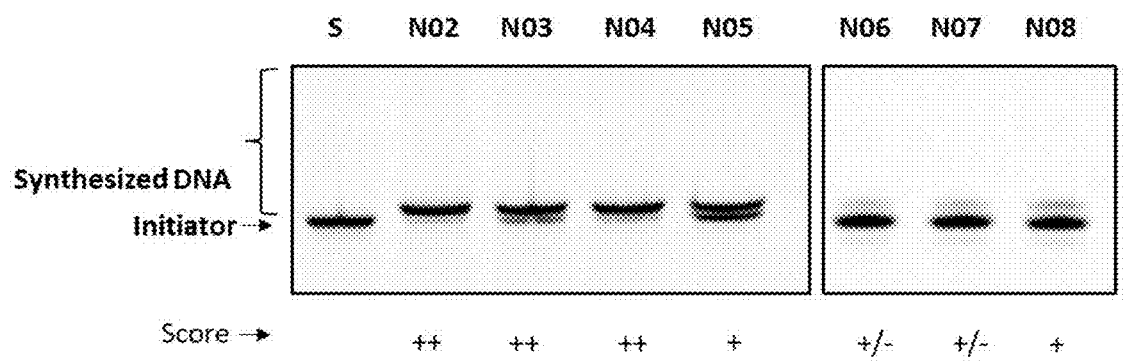
FIG. 10 shows the results of the reactions described in Example 7.1.

As shown in FIG. 10, the variants N02, N03, and N04 carrying substitutions in the motif Exo I and motif A exhibited around 50% to 95% of DNA synthesis activity in the presence of 3'-O-AZ-dCTP. The addition of 3'-O-AZ-dCMP to the FAM-45-mer DNA generates a 46-mer DNA product.

TABLE 7.1

List of amino acid substitutions in the PolB variants derived from 9° N.

| Type of PolB Enzyme | Variant No. | Residues and Amino Acid Substitutions |
|---|---|---|
| 9° N DNA polymerase | N05 | D141A + E143A + L408Y + P410G + A485V |
| | N06 | D141A + E143A + L408Y + Y409A + P410H + A485V |
| | N07 | D141A + E143A + L408Y + Y409C + P410G + A485V |
| | N08 | D141A + E143A + L408Y + Y409G + P410G + A485V |

Example 7.2: Template-Independent DNA Synthesis Activity of Vent Variants

In this Example, the variants modified from $Vent^{exo-}$ (V01) backbone is selected and exemplified. The template-independent DNA synthesis activities of these Vent variants to extend the FAM-45-mer DNA initiator in the presence of 3'-O-AZ-dATP are evaluated using the same activity assay as described above. The Vent-derived variants are listed in Table 7.2. Moreover, according to the relative DNA synthesis activity scoring criteria as described in Example 6, the relative DNA synthesis activity scoring of each variant are also illustrated in FIG. 11, where "S" stands for the substrate (FAM-45-mer DNA initiator) and serves as a blank DNA control.

Figure 11:
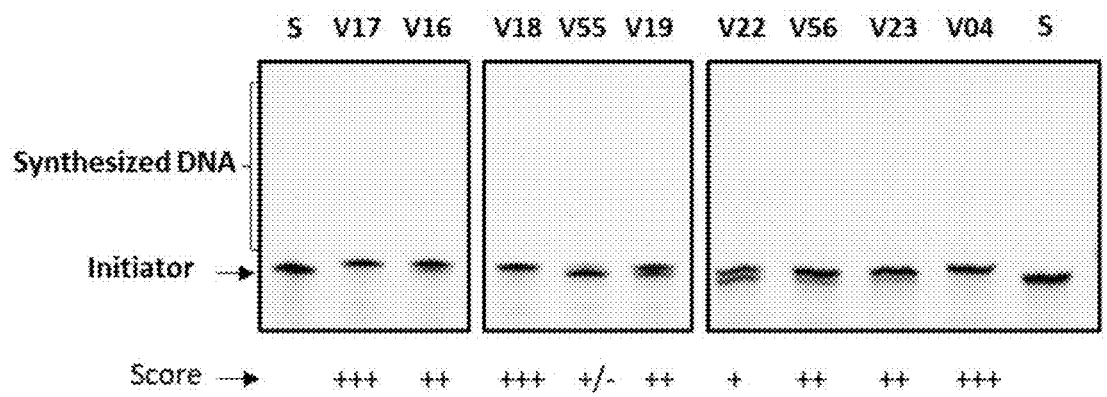
FIG. 11 shows the results of the reactions described in Example 7.2.

As shown in FIG. 11, the variants V04, V17, and V18 carrying combinatory substitutions in the motif Exo I, motif A, and motif B exhibited 100% DNA synthesis activity in the presence of 3'-O-AZ-dATP and produced a 46-mer DNA product.

TABLE 7.2

List of amino acid substitutions in the PolB valiants derived from Vent.

| Type of PolB Enzyme | Variant No. | Residues and Amino Acid Substitutions |
|---|---|---|
| Vent | V04 | D141A + E143A + L411Y + Y412A + P413G + A488L |
| | V16 | D141A + E143A + L411C + Y412A + P413G + A488L |
| | V17 | D141A + E143A + L411A + Y412A + P413G + A488L |
| | V18 | D141A + E143A + L411F + Y412A + P413G + A488L |
| | V19 | D141A + E143A + L411H + Y412A + P413G + A488L |
| | V22 | D141A + E143A + L411T + Y412A + P413G + A488L |
| | V23 | D141A + E143A + L411W + Y412A + P413G + A488L |
| | V55 | D141A + E143A + L411G + Y412A + P413G + A488L |
| | V56 | D141A + E143A + L411V + Y412A + P413G + A488L |

In view of above results, a robust template-independent DNA synthesis activity in the presence of 3'-O-AZ-dNTPs were commonly observed on various PolB variants derived from different sources of PolB s provided by the present invention. Accordingly, the Vent variants are further selected to demonstrate the ability of this variants for the template-independent DNA synthesis function. The list of these variants is shown in Table 7.3. The score of relative DNA synthesis activity of each variant in the presence of 3'-O-AZ-dNTP are also shown in Table 7.3 as described above.

TABLE 7.3

List of amino acid substitutions and the relative activity scoring of Vent variants.

| Variant No. | Residue and Amino Acid Substitutions | 3'-O-AZ-dNTP | Activity score |
|---|---|---|---|
| V03 | D141A + E143A + A488L | 3'-O-AZ-dATP | +/− |
| V04 | D141A + E143A + L411Y + Y412A + P413G + A488L | 3'-O-AZ-dCTP | +++ |
| V08 | D141A + E143A + L411Q + Y412A + P413G + A488L | 3'-O-AZ-dCTP | +++ |
| V09 | D141A + E143A + L411Y + Y412A + P413G + A488E | 3'-O-AZ-dGTP | +++ |
| V10 | D141A + E143A + L411Y + Y412A + P413G + A488F | 3'-O-AZ-dGTP | +++ |
| V11 | D141A + E143A + L411Y + Y412C + P413G + A488L | 3'-O-AZ-dTTP | +/− |
| V12 | D141A + E143A + L411Y + Y412D + P413G + A488L | 3'-O-AZ-dTTP | +/− |
| V14 | D141A + E143A + L411Y + Y412F + P413G + A488L | 3'-O-AZ-dTTP | + |
| V15 | D141A + E143A + L411Y + Y412G + P413G + A488L | 3'-O-AZ-dTTP | +++ |
| V17 | D141A + E143A + L411A + Y412A + P413G + A488L | 3'-O-AZ-dCTP | +++ |
| V18 | D141A + E143A + L411F + Y412A + P413G + A488L | 3'-O-AZ-dCTP | +++ |
| V19 | D141A + E143A + L411H + Y412A + P413G + A488L | 3'-O-AZ-dCTP | +++ |
| V20 | D141A + E143A + L411I + Y412A + P413G + A488L | 3'-O-AZ-dCTP | ++ |
| V21 | D141A + E143A + L411S + Y412A + P413G + A488L | 3'-O-AZ-dCTP | +++ |
| V23 | D141A + E143A + L411W + Y412A + P413G + A488L | 3'-O-AZ-dCTP | +++ |
| V24 | D141A + E143A + L411Y + Y412H + P413G + A488L | 3'-O-AZ-dTTP | +/− |
| V25 | D141A + E143A + L411Y + Y412I + P413G + A488L | 3'-O-AZ-dTTP | +/− |
| V26 | D141A + E143A + L411Y + Y412K + P413G + A488L | 3'-O-AZ-dTTP | +/− |
| V27 | D141A + E143A + L411Y + Y412L + P413G + A488L | 3'-O-AZ-dTTP | + |
| V28 | D141A + E143A + L411Y + Y412M + P413G + A488L | 3'-O-AZ-dTTP | + |
| V29 | D141A + E143A + L411Y + Y412N + P413G + A488L | 3'-O-AZ-dTTP | + |
| V30 | D141A + E143A + L411Y + Y412Q + P413G + A488L | 3'-O-AZ-dTTP | +/− |
| V37 | D141A + E143A + L411Y + Y412A + P413A + A488L | 3'-O-AZ-dCTP | +++ |
| V50 | D141A + E143A + L411Y + Y412A + P413S + A488L | 3'-O-AZ-dCTP | +++ |
| V51 | D141A + E143A + L411Y + Y412A + P413T + A488L | 3'-O-AZ-dCTP | ++ |
| V57 | D141A + E143A + A488C | 3'-O-AZ-dATP | +++ |
| V58 | D141A + E143A + A488D | 3'-O-AZ-dATP | +++ |
| V59 | D141A + E143A + A488E | 3'-O-AZ-dATP | +++ |
| V60 | D141A + E143A + A488F | 3'-O-AZ-dATP | +++ |
| V61 | D141A + E143A + A488G | 3'-O-AZ-dATP | +++ |
| V62 | D141A + E143A + A488H | 3'-O-AZ-dATP | +/− |
| V63 | D141A + E143A + A488K | 3'-O-AZ-dATP | +/− |
| V64 | D141A + E143A + A488R | 3'-O-AZ-dATP | +/− |
| V65 | D141A + E143A + A488T | 3'-O-AZ-dATP | +++ |
| V66 | D141A + E143A + A488Y | 3'-O-AZ-dATP | +/− |
| V67 | D141A + E143A + L411Y + Y412A + P413G + A488C | 3'-O-AZ-dGTP | ++ |
| V68 | D141A + E143A + L411Y + Y412A + P413G + A488D | 3'-O-AZ-dGTP | +++ |
| V69 | D141A + E143A + L411Y + Y412A + P413G + A488G | 3'-O-AZ-dGTP | ++ |
| V70 | D141A + E143A + L411Y + Y412A + P413G + A488H | 3'-O-AZ-dGTP | +++ |
| V71 | D141A + E143A + L411Y + Y412A + P413G + A488K | 3'-O-AZ-dGTP | +++ |
| V72 | D141A + E143A + L411Y + Y412A + P413G + A488R | 3'-O-AZ-dGTP | ++ |
| V73 | D141A + E143A + L411Y + Y412A + P413G + A488T | 3'-O-AZ-dGTP | +++ |
| V74 | D141A + E143A + L411Y + Y412A + P413G + A488Y | 3'-O-AZ-dGTP | +++ |

Example 7.3: Template-Independent DNA Synthesis Activity of Pfu, Kod1, and Sso Variants In this Example, the variants modified from Pfu$^{exo-}$ (P01), Kod1$^{exo-}$ (K01), and Sso$^{exo-}$ (S01) backbone are selected and exemplified. The template-independent DNA synthesis activities of these variants to extend the FAM-45-mer DNA initiator in the presence of 3'-O-AZ-dATP are evaluated using the same activity assay as described above. The list of variants used in this example and their relative DNA synthesis activity thereof are listed in Table 7.4.

The results show that Pfu$^{exo-}$, Kod1$^{exo-}$, and Sso$^{exo-}$ variants carrying combinatory substitutions exhibited 100% DNA synthesis activity in the presence of 3'-O-AZ-dATP. However, the variant K04 carrying combinatory amino acid substitutions in the motif Exo I (D141A+E143A), motif A (L408A+Y409A+P410I) and motif B (A485L) showed a marginal activity as compared to K03.

TABLE 7.4

List of amino acid substitutions and relative activity scores of Pfu$^{exo-}$, Kod1$^{exo-}$, and Sso$^{exo-}$ variants.

| Variant No. | Type of PolB with Amino Acid Substitutions | Activity score |
|---|---|---|
| P03 | Pfu$^{exo-}$ + L409Y + Y410A + P411G + A486L | ++ |
| K03 | Kod1$^{exo-}$ + L408Y + Y409A + P410G + A485L | ++ |
| K04 | Kod1$^{exo-}$ + L408A + Y409A + P410I + A485L | + |
| S05 | Sso$^{exo-}$ + L518Y + Y519A + P520G + A601L | ++ |

Figure 12:
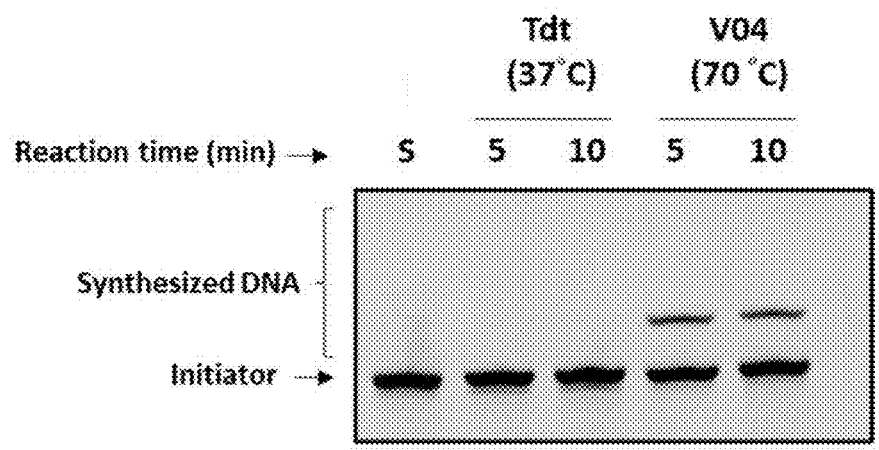
FIG. 12 shows the results of the reactions described in Example 8.

Example 8: Template-Independent DNA Synthesis Activity of PolB Variants on FAM-45-mer DNA Initiator in the Presence of Dye-Labeled Nucleotide Analogues In this Example, the ability of PolB variants to utilize a dye-labeled nucleotide analogue for the template-independent DNA synthesis is further demonstrated by the exemplary PolB variants. The variants modified from Vent$^{exo-}$ (V01) backbone are selected and exemplified. The template-independent DNA synthesis activities of these Vent variants to extend the FAM-45-mer DNA initiator in the presence of a Cy5-labeled dTTP (Cy5-dTTP) are evaluated using the same activity assay as described above. The DNA synthesis activity assay is conducted at the hyperthermal reaction temperature of 70° C. Meanwhile, the Tdt enzyme was also used for direct comparison. The activity assay for Tdt enzyme was conducted at the reaction temperature of 37° C., which is the standard working temperature for the Tdt enzyme. For the sake of brevity, the variant V04 was selected to demonstrate the template-independent DNA synthesis activity in the presence of Cy5-dTTP. The results are shown in FIG. 12, where "S" stands for the substrate (FAM-45-mer DNA initiator) and serves as a blank DNA control. As shown in FIG. 12, the variant V04 shows a robust DNA synthesis activity by incorporating Cy5-dTTP to the FAM-45-mer DNA initiator.

In view of the results observed above, the PolB variants and the kit provided herein have been further proven to incorporate a variety of nucleotides effectively and efficiently for de novo enzymatic nucleic acid synthesis; and they are also proven to successfully exert the conferred template-independent DNA synthesis function under broader reaction temperatures covering from atmospheric temperatures to the hyperthermal conditions, demonstrating a higher thermotolerance. Therefore, the PolB variants and the kit within the scope of the present disclosure can broaden the scope of various applications of template-independent enzymatic nucleic acids synthesis in different reaction conditions.

The present disclosure has been described with embodiments thereof, and it is understood that various modifications, without departing from the scope of the present disclosure, are in accordance with the embodiments of the present disclosure. Hence, the embodiments described are intended to cover the modifications within the scope of the present disclosure, rather than to limit the present disclosure. The scope of the claims therefore should be accorded the broadest interpretation so as to encompass all such modifications.

What is claimed is:

1. A B-family DNA polymerase variant modified from a wild-type B-family DNA polymerase having an amino acid sequence selected from the group consisting of SEQ ID NOs: 2, 3, 4, 5, 6, 7, 8, 9, 10, 11, 12, 13, 14, 15, 16, and 17, wherein
   an amino acid L at position 408 of SEQ ID NOs: 2, 3, or 4 is substituted with F, H, I, Q, S, W, or Y;
   an amino acid L at position 409 of SEQ ID NO: 5 is substituted with F, H, I, Q, S, W, or Y;
   an amino acid L at position 411 of SEQ ID NO: 6 is substituted with F, H, I, Q, S, W, or Y;
   an amino acid L at position 485 of SEQ ID NO: 7 is substituted with F, H, I, Q, S, W, or Y;
   an amino acid M at position 426 of SEQ ID NO: 8 is substituted with F, H, I, Q, S, W, or Y;
   an amino acid L at position 518 of SEQ ID NO: 9 is substituted with F, H, I, Q, S, W, or Y;
   an amino acid L at position 417 of SEQ ID NO: 10 is substituted with F, H, I, Q, S, W, or Y;
   an amino acid L at position 606 of SEQ ID NO: 11 is substituted with F, H, I, Q, S, W, or Y;
   an amino acid L at position 612 of SEQ ID NO: 12 is substituted with F, H, I, Q, S, W, or Y;
   an amino acid L at position 425 of SEQ ID NO: 13 is substituted with F, H, I, Q, S, W, or Y;
   an amino acid L at position 423 of SEQ ID NO: 14 is substituted with F, H, I, Q, S, W, or Y;
   an amino acid L at position 415 of SEQ ID NO: 15 is substituted with F, H, I, Q, S, W, or Y;
   an amino acid L at position 412 of SEQ ID NO: 16 is substituted with F, H, I, Q, S, W, or Y; or an amino acid L at position 253 of SEQ ID NO: 17 is substituted with F, H, I, Q, S, W, or Y.

2. The B-family DNA polymerase variant of claim 1, wherein the B-family DNA polymerase variant is modified from a wild-type B-family DNA polymerase having an amino acid sequence selected from the group consisting of SEQ ID NOs: 2, 3, 4, 5, 6, 7, 8, and 9.

3. The B-family DNA polymerase variant of claim 1, wherein the wild-type B-family DNA polymerase is *Thermococcus gorgonarius* DNA polymerase (Tgo), *Thermococcus kodakarensis* DNA polymerase (Kod1), *Thermococcus* sp. (strain 9° N-7) DNA polymerase (9° N), *Pyrococcus furiosus* DNA polymerase (Pfu), *Thermococcus litoralis* DNA polymerase (Vent), *Methanococcus maripaludis* DNA polymerase (Mma), *Methanosarcina acetivorans* DNA polymerase (Mac), human DNA polymerase delta catalytic p125 subunit (hPOLD), *Saccharomyces cerevisiae* DNA polymerase delta catalytic subunit (ScePOLD), *Pyrobaculum islandicum* DNA polymerase (Pis), *Sulfolobus solfataricus* DNA polymerase (Sso), *Pseudomonas aeruginosa* DNA polymerase II (Pae), *Escherichia coli* DNA polymerase II (Eco), *Escherichia* phage RB69 DNA polymerase (RB69), *Escherichia* phage T4 DNA polymerase (T4), or *Bacillus* phage Phi29 DNA polymerase (Phi29).

4. The B-family DNA polymerase variant of claim 3, wherein the B-family DNA polymerase variant has deficient 3' to 5' exonuclease activity.

5. The B-family DNA polymerase variant of claim 4, wherein the B-family DNA polymerase variant having deficient 3' to 5' exonuclease activity is derived from *Thermococcus gorgonarius* DNA polymerase (Tgo) having a wild-type amino acid sequence of SEQ ID NO: 2; and wherein
  ii. an amino acid Y at position 409 of SEQ ID NO: 2 is not substituted or substituted with A, C, D, F, G, H, I, K, L, M, N, or Q; and
  iii. an amino acid P at position 410 of SEQ ID NO: 2 is not substituted or substituted with A, G, S, or T.

6. The B-family DNA polymerase variant of claim 4, wherein the B-family DNA polymerase variant having deficient 3' to 5' exonuclease activity is derived from *Thermococcus gorgonarius* DNA polymerase (Tgo) having a wild-type amino acid sequence of SEQ ID NO: 2; and wherein
  ii. an amino acid Y at position 409 of SEQ ID NO: 2 is not substituted or substituted with A, C, D, F, G, H, I, K, L, M, N, or Q;
  iii. an amino acid P at position 410 of SEQ ID NO: 2 is not substituted or substituted with A, G, S, or T; and
  iv. an amino acid A at position 485 of SEQ ID NO: 2 is substituted with C, D, E, F, G, H, K, L, R, T, or Y.

7. The B-family DNA polymerase variant of claim 4, wherein the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein:
  ii. an amino acid Y at position 409 of SEQ ID NO: 3 is not substituted or substituted with A, C, D, F, G, H, I, K, L, M, N, or Q; and
  iii. an amino acid P at position 410 of SEQ ID NO: 3 is not substituted or substituted with A, G, S, or T.

8. The B-family DNA polymerase variant of claim 4, wherein the B-family DNA polymerase variant having deficient 3' to 5' exonuclease activity is derived from *Thermococcus kodakarensis* DNA polymerase (Kod1) having a wild-type amino acid sequence of SEQ ID NO: 3; and wherein
  ii. an amino acid Y at position 409 of SEQ ID NO: 3 is not substituted or substituted with A, C, D, F, G, H, I, K, L, M, N, or Q;
  iii. an amino acid P at position 410 of SEQ ID NO: 3 is not substituted or substituted with A, G, S, or T; and
  iv. an amino acid A at position 485 of SEQ ID NO: 3 is substituted with C, D, E, F, G, H, K, L, R, T, or Y.

9. The B-family DNA polymerase variant of claim 4, wherein the B-family DNA polymerase variant having deficient 3' to 5' exonuclease activity is derived from *Thermococcus* sp. (strain 9° N-7) DNA polymerase (9° N) having a wild-type amino acid sequence of SEQ ID NO: 4; and wherein
  ii. an amino acid Y at position 409 of SEQ ID NO: 4 is not substituted or substituted with A, C, D, F, G, H, I, K, L, M, N, or Q; and
  iii. an amino acid P at position 410 of SEQ ID NO: 4 is not substituted or substituted with A, G, S, or T.

10. The B-family DNA polymerase variant of claim 4, wherein the B-family DNA polymerase variant having deficient 3' to 5' exonuclease activity is derived from *Thermococcus* sp. (strain 9° N-7) DNA polymerase (9° N) having a wild-type amino acid sequence of SEQ ID NO: 4; and wherein
  ii. an amino acid Y at position 409 of SEQ ID NO: 4 is not substituted or substituted with A, C, D, F, G, H, I, K, L, M, N, or Q;
  iii. an amino acid P at position 410 of SEQ ID NO: 4 is not substituted or substituted with A, G, S, or T; and
  iv. an amino acid A at position 485 of SEQ ID NO: 4 is substituted with C, D, E, F, G, H, K, L, R, T, or Y.

11. The B-family DNA polymerase variant of claim 4, wherein the B-family DNA polymerase variant having deficient 3' to 5' exonuclease activity is derived from *Pyrococcus furiosus* DNA polymerase (Pfu) having a wild-type amino acid sequence of SEQ ID NO: 4; and wherein
  ii. an amino acid Y at position 410 of SEQ ID NO: 5 is not substituted or substituted with A, C, D, F, G, H, I, K, L, M, N, or Q; and
  iii. an amino acid P at position 411 of SEQ ID NO: 5 is not substituted or substituted with A, G, S, or T.

12. The B-family DNA polymerase variant of claim 4, wherein the B-family DNA polymerase variant having deficient 3' to 5' exonuclease activity is derived from *Pyrococcus furiosus* DNA polymerase (Pfu) having a wild-type amino acid sequence of SEQ ID NO: 4; and wherein
  ii. an amino acid Y at position 410 of SEQ ID NO: 5 is not substituted or substituted with A, C, D, F, G, H, I, K, L, M, N, or Q;
  iii. an amino acid P at position 411 of SEQ ID NO: 5 is not substituted or substituted with A, G, S, or T; and
  iv. an amino acid A at position 486 of SEQ ID NO: 5 is substituted with C, D, E, F, G, H, K, L, R, T, or Y.

13. The B-family DNA polymerase variant of claim 4, wherein the B-family DNA polymerase variant having deficient 3' to 5' exonuclease activity is derived from *Thermococcus litoralis* DNA polymerase (Vent) having a wild-type amino acid sequence of SEQ ID NO: 6; and wherein
  ii. an amino acid Y at position 412 of SEQ ID NO: 6 is not substituted or substituted with A, C, D, F, G, H, I, K, L, M, N, or Q; and
  iii. an amino acid P at position 413 of SEQ ID NO: 6 is not substituted or substituted with A, G, S, or T.

14. The B-family DNA polymerase variant of claim 4, wherein the B-family DNA polymerase variant having deficient 3' to 5' exonuclease activity is derived from *Thermo-*

*coccus litoralis* DNA polymerase (Vent) having a wild-type amino acid sequence of SEQ ID NO: 6; and wherein
  ii. an amino acid Y at position 412 of SEQ ID NO: 6 is not substituted or substituted with A, C, D, F, G, H, I, K, L, M, N, or Q;
  iii an amino acid P at position 413 of SEQ ID NO: 6 is not substituted or substituted with A, G, S, or T; and
  iv. an amino acid A at position 488 of SEQ ID NO: 6 is substituted with C, D, E, F, G, H, K, L, R, T, or Y.

15. The B-family DNA polymerase variant of claim 4, wherein the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein
  ii. an amino acid Y at position 486 of SEQ ID NO: 7 is not substituted or substituted with A, C, D, F, G, H, I, K, L, M, N, or Q; and
  iii. an amino acid P at position 487 of SEQ ID NO: 7 is not substituted or substituted with A, G, S, or T.

16. The B-family DNA polymerase variant of claim 4, wherein the B-family DNA polymerase variant having deficient 3' to 5' exonuclease activity is derived from *Methanosarcina acetivorans* DNA polymerase (Mac) having a wild-type amino acid sequence of SEQ ID NO: 7; and wherein
  ii. an amino acid Y at position 486 of SEQ ID NO: 7 is not substituted or substituted with A, C, D, F, G, H, I, K, L, M, N, or Q;
  iii. an amino acid P at position 487 of SEQ ID NO: 7 is not substituted or substituted with A, G, S, or T; and
  iv. the amino acid A at position 565 of SEQ ID NO: 7 is substituted with C, D, E, F, G, H, K, L, R, T, or Y.

17. The B-family DNA polymerase variant of claim 4, wherein the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein
  ii. an amino acid Y at position 427 of SEQ ID NO: 8 is not substituted or substituted with A, C, D, F, G, H, I, K, L, M, N, or Q; and
  iii. an amino acid P at position 428 of SEQ ID NO: 8 is not substituted or substituted with A, G, S, or T.

18. The B-family DNA polymerase variant of claim 4, wherein the B-family DNA polymerase variant having deficient 3' to 5' exonuclease activity is derived from *Pyrobaculum islandicum* DNA polymerase (Pis) having a wild-type amino acid sequence of SEQ ID NO: 8; and wherein
  ii. an amino acid Y at position 427 of SEQ ID NO: 8 is not substituted or substituted with A, C, D, F, G, H, I, K, L, M, N, or Q;
  iii. an amino acid P at position 428 of SEQ ID NO: 8 is not substituted or substituted with A, G, S, or T; and
  iv. an amino acid A at position 508 of SEQ ID NO: 8 is substituted with C, D, E, F, G, H, K, L, R, T, or Y.

19. The B-family DNA polymerase variant of claim 4, wherein the B-family DNA polymerase variant having deficient 3' to 5' exonuclease activity is derived from *Sulfolobus solfataricus* DNA polymerase (Sso) having a wild-type amino acid sequence of SEQ ID NO: 9; and wherein
  ii. an amino acid Y at position 519 of SEQ ID NO: 9 is not substituted or substituted with A, C, D, F, G, H, I, K, L, M, N, or Q; and
  iii. an amino acid P at position 520 of SEQ ID NO: 9 is not substituted or substituted with A, G, S, or T.

20. The B-family DNA polymerase variant of claim 4, wherein the B-family DNA polymerase variant having deficient 3' to 5' exonuclease activity is derived from *Sulfolobus solfataricus* DNA polymerase (Sso) having a wild-type amino acid sequence of SEQ ID NO: 9; and wherein
  ii. an amino acid Y at position 519 of SEQ ID NO: 9 is not substituted or substituted with A, C, D, F, G, H, I, K, L, M, N, or Q;
  iii. an amino acid P at position 520 of SEQ ID NO: 9 is not substituted or substituted with A, G, S, or T; and
  iv. an amino acid A at position 601 of SEQ ID NO: 9 is substituted with C, D, E, F, G, H, K, L, R, T, or Y.

21. The B-family DNA polymerase variant of claim 4, wherein the B-family DNA polymerase variant exhibits an activity of synthesizing nucleic acids in a template-independent manner by adding at least one nucleotide selected from the group of naturally occurring nucleotide, nucleotide analogue, or a mixture thereof, to an extendible initiator.

22. The B-family DNA polymerase variant of claim 21, wherein the extendible initiator comprises a single-stranded oligonucleotide initiator, a blunt-ended double-stranded oligonucleotide initiator, or a mixture thereof.

23. The B-family DNA polymerase variant of claim 21, wherein the extendible initiator is free form nucleic acid to be reacted in a liquid phase.

24. The B-family DNA polymerase variant of claim 21, wherein the extendible initiator is immobilized on a solid support, wherein the solid support comprises a particle, bead, slide, array surface, membrane, flow cell, well, microwell, nano-well, chamber, microfluidic chamber, channel, microfluidic channel, or any other surfaces.

25. The B-family DNA polymerase variant of claim 21, wherein the at least one nucleotide is linked with a detectable label.

26. The B-family DNA polymerase variant of claim 21, wherein the B-family DNA polymerase variant exhibits the activity at reaction temperatures from 10° C. to 100° C.

27. A kit for performing de novo enzymatic nucleic acid synthesis, comprising a B-family DNA polymerase variant derived from a wild-type B-family DNA polymerase having an amino acid sequence selected from the group consisting of SEQ ID NOs: 2, 3, 4, 5, 6, 7, 8, 9, 10, 11, 12, 13, 14, 15, 16, and 17, wherein the B-family DNA polymerase variant exhibits activity of synthesizing nucleic acids in a template-independent manner by adding at least one nucleotide selected from the group of naturally occurring nucleotide, nucleotide analogue, or a mixture thereof, to an extendible initiator, thereby synthesizing a desired nucleic acid sequence, and wherein an amino acid L at position 408 of SEQ ID NOs: 2, 3, or 4 is substituted with F, H, I, Q, S, W, or Y;
  an amino acid L at position 409 of SEQ ID NO: 5 is substituted with F, H, I, Q, S, W, or Y;
  an amino acid L at position 411 of SEQ ID NO: 6 is substituted with F, H, I, Q, S, W, or Y;
  an amino acid L at position 485 of SEQ ID NO: 7 is substituted with F, H, I, Q, S, W, or Y;
  an amino acid M at position 426 of SEQ ID NO: 8 is substituted with F, H, I, Q, S, W, or Y;
  an amino acid L at position 518 of SEQ ID NO: 9 is substituted with F, H, I, Q, S, W, or Y;
  an amino acid L at position 417 of SEQ ID NO: 10 is substituted with F, H, I, Q, S, W, or Y;
  an amino acid L at position 606 of SEQ ID NO: 11 is substituted with F, H, I, Q, S, W, or Y;
  an amino acid L at position 612 of SEQ ID NO: 12 is substituted with F, H, I, Q, S, W, or Y;
  an amino acid L at position 425 of SEQ ID NO: 13 is substituted with F, H, I, Q, S, W, or Y;

an amino acid L at position 423 of SEQ ID NO: 14 is substituted with F, H, I, Q, S, W, or Y;

an amino acid L at position 415 of SEQ ID NO: 15 is substituted with F, H, I, Q, S, W, or Y;

an amino acid L at position 412 of SEQ ID NO: 16 is substituted with F, H, I, Q, S, W, or Y; or an amino acid L at position 253 of SEQ ID NO: 17 is substituted with F, H, I, Q, S, W, or Y.

\* \* \* \* \*

UNITED STATES PATENT AND TRADEMARK OFFICE
CERTIFICATE OF CORRECTION

PATENT NO. : 12,098,396 B2
APPLICATION NO. : 17/936816
DATED : September 24, 2024
INVENTOR(S) : Cheng-Yao Chen et al.

Page 1 of 1

It is certified that error appears in the above-identified patent and that said Letters Patent is hereby corrected as shown below:

In the Claims

Column 76, Line 37, the recitation "SEQ ID NO: 4" should read --SEQ ID NO: 5--.

Column 76, Line 47, the recitation "SEQ ID NO: 4" should read --SEQ ID NO: 5--.

Signed and Sealed this
Fifth Day of August, 2025

Coke Morgan Stewart
*Acting Director of the United States Patent and Trademark Office*

```
                         SEQUENCE LISTING

Sequence total quantity: 20
SEQ ID NO: 1             moltype = AA  length = 1360
FEATURE                  Location/Qualifiers
REGION                   1..1360
                         note = consensus sequence
REGION                   6..10
                         note = misc_feature - Xaa can be any naturally occurring
                          amino acid
SITE                     12
                         note = misc_feature - Xaa can be any naturally occurring
                          amino acid
SITE                     14
                         note = misc_feature - Xaa can be any naturally occurring
                          amino acid
REGION                   17..22
                         note = misc_feature - Xaa can be any naturally occurring
                          amino acid
SITE                     26
                         note = misc_feature - Xaa can be any naturally occurring
                          amino acid
SITE                     28
                         note = misc_feature - Xaa can be any naturally occurring
                          amino acid
REGION                   30..34
                         note = misc_feature - Xaa can be any naturally occurring
                          amino acid
SITE                     46
                         note = misc_feature - Xaa can be any naturally occurring
                          amino acid
REGION                   48..52
                         note = misc_feature - Xaa can be any naturally occurring
                          amino acid
REGION                   54..59
                         note = misc_feature - Xaa can be any naturally occurring
                          amino acid
SITE                     79
                         note = misc_feature - Xaa can be any naturally occurring
                          amino acid
REGION                   81..84
                         note = misc_feature - Xaa can be any naturally occurring
                          amino acid
SITE                     86
                         note = misc_feature - Xaa can be any naturally occurring
                          amino acid
REGION                   89..95
                         note = misc_feature - Xaa can be any naturally occurring
                          amino acid
REGION                   100..102
                         note = misc_feature - Xaa can be any naturally occurring
                          amino acid
```

-continued

| | | |
|---|---|---|
| REGION | 105..106 | note = misc_feature - Xaa can be any naturally occurring amino acid |
| SITE | 111 | note = misc_feature - Xaa can be any naturally occurring amino acid |
| REGION | 114..116 | note = misc_feature - Xaa can be any naturally occurring amino acid |
| REGION | 120..121 | note = misc_feature - Xaa can be any naturally occurring amino acid |
| SITE | 124 | note = misc_feature - Xaa can be any naturally occurring amino acid |
| SITE | 127 | note = misc_feature - Xaa can be any naturally occurring amino acid |
| SITE | 134 | note = misc_feature - Xaa can be any naturally occurring amino acid |
| SITE | 136 | note = misc_feature - Xaa can be any naturally occurring amino acid |
| SITE | 140 | note = misc_feature - Xaa can be any naturally occurring amino acid |
| REGION | 142..143 | note = misc_feature - Xaa can be any naturally occurring amino acid |
| REGION | 145..146 | note = misc_feature - Xaa can be any naturally occurring amino acid |
| SITE | 157 | note = misc_feature - Xaa can be any naturally occurring amino acid |
| REGION | 183..184 | note = misc_feature - Xaa can be any naturally occurring amino acid |
| REGION | 186..187 | note = misc_feature - Xaa can be any naturally occurring amino acid |
| SITE | 206 | note = misc_feature - Xaa can be any naturally occurring amino acid |
| SITE | 208 | note = misc_feature - Xaa can be any naturally occurring amino acid |
| SITE | 210 | note = misc_feature - Xaa can be any naturally occurring amino acid |
| SITE | 213 | note = misc_feature - Xaa can be any naturally occurring amino acid |
| REGION | 233..234 | note = misc_feature - Xaa can be any naturally occurring amino acid |
| SITE | 245 | note = misc_feature - Xaa can be any naturally occurring amino acid |
| REGION | 265..267 | note = misc_feature - Xaa can be any naturally occurring amino acid |
| REGION | 269..270 | note = misc_feature - Xaa can be any naturally occurring amino acid |
| REGION | 273..274 | note = misc_feature - Xaa can be any naturally occurring amino acid |
| SITE | 299 | note = misc_feature - Xaa can be any naturally occurring amino acid |

| | | |
|---|---|---|
| REGION | 305..307 | |
| | note = misc_feature - Xaa can be any naturally occurring amino acid | |
| REGION | 313..314 | |
| | note = misc_feature - Xaa can be any naturally occurring amino acid | |
| SITE | 316 | |
| | note = misc_feature - Xaa can be any naturally occurring amino acid | |
| REGION | 321..325 | |
| | note = misc_feature - Xaa can be any naturally occurring amino acid | |
| REGION | 328..329 | |
| | note = misc_feature - Xaa can be any naturally occurring amino acid | |
| REGION | 333..336 | |
| | note = misc_feature - Xaa can be any naturally occurring amino acid | |
| SITE | 361 | |
| | note = misc_feature - Xaa can be any naturally occurring amino acid | |
| SITE | 373 | |
| | note = misc_feature - Xaa can be any naturally occurring amino acid | |
| REGION | 410..411 | |
| | note = misc_feature - Xaa can be any naturally occurring amino acid | |
| SITE | 420 | |
| | note = misc_feature - Xaa can be any naturally occurring amino acid | |
| SITE | 426 | |
| | note = misc_feature - Xaa can be any naturally occurring amino acid | |
| SITE | 428 | |
| | note = misc_feature - Xaa can be any naturally occurring amino acid | |
| REGION | 446..449 | |
| | note = misc_feature - Xaa can be any naturally occurring amino acid | |
| SITE | 466 | |
| | note = misc_feature - Xaa can be any naturally occurring amino acid | |
| REGION | 479..481 | |
| | note = misc_feature - Xaa can be any naturally occurring amino acid | |
| SITE | 486 | |
| | note = misc_feature - Xaa can be any naturally occurring amino acid | |
| SITE | 492 | |
| | note = misc_feature - Xaa can be any naturally occurring amino acid | |
| SITE | 497 | |
| | note = misc_feature - Xaa can be any naturally occurring amino acid | |
| REGION | 565..566 | |
| | note = misc_feature - Xaa can be any naturally occurring amino acid | |
| SITE | 570 | |
| | note = misc_feature - Xaa can be any naturally occurring amino acid | |
| REGION | 572..573 | |
| | note = misc_feature - Xaa can be any naturally occurring amino acid | |
| SITE | 581 | |
| | note = misc_feature - Xaa can be any naturally occurring amino acid | |
| SITE | 586 | |
| | note = misc_feature - Xaa can be any naturally occurring amino acid | |
| SITE | 598 | |
| | note = misc_feature - Xaa can be any naturally occurring amino acid | |

-continued

| | | |
|---|---|---|
| SITE | 605 | |
| | note = misc_feature - Xaa can be any naturally occurring amino acid | |
| SITE | 616 | |
| | note = misc_feature - Xaa can be any naturally occurring amino acid | |
| SITE | 618 | |
| | note = misc_feature - Xaa can be any naturally occurring amino acid | |
| SITE | 626 | |
| | note = misc_feature - Xaa can be any naturally occurring amino acid | |
| SITE | 665 | |
| | note = misc_feature - Xaa can be any naturally occurring amino acid | |
| SITE | 667 | |
| | note = misc_feature - Xaa can be any naturally occurring amino acid | |
| REGION | 671..673 | |
| | note = misc_feature - Xaa can be any naturally occurring amino acid | |
| REGION | 681..683 | |
| | note = misc_feature - Xaa can be any naturally occurring amino acid | |
| SITE | 700 | |
| | note = misc_feature - Xaa can be any naturally occurring amino acid | |
| SITE | 705 | |
| | note = misc_feature - Xaa can be any naturally occurring amino acid | |
| SITE | 709 | |
| | note = misc_feature - Xaa can be any naturally occurring amino acid | |
| VARIANT | 715 | |
| | note = leucine (L) or methionine (M) | |
| SITE | 721 | |
| | note = misc_feature - Xaa can be any naturally occurring amino acid | |
| SITE | 737 | |
| | note = misc_feature - Xaa can be any naturally occurring amino acid | |
| SITE | 741 | |
| | note = misc_feature - Xaa can be any naturally occurring amino acid | |
| SITE | 744 | |
| | note = misc_feature - Xaa can be any naturally occurring amino acid | |
| REGION | 751..752 | |
| | note = misc_feature - Xaa can be any naturally occurring amino acid | |
| REGION | 754..756 | |
| | note = misc_feature - Xaa can be any naturally occurring amino acid | |
| SITE | 760 | |
| | note = misc_feature - Xaa can be any naturally occurring amino acid | |
| SITE | 763 | |
| | note = misc_feature - Xaa can be any naturally occurring amino acid | |
| SITE | 796 | |
| | note = misc_feature - Xaa can be any naturally occurring amino acid | |
| REGION | 798..800 | |
| | note = misc_feature - Xaa can be any naturally occurring amino acid | |
| SITE | 802 | |
| | note = misc_feature - Xaa can be any naturally occurring amino acid | |
| SITE | 804 | |
| | note = misc_feature - Xaa can be any naturally occurring amino acid | |
| REGION | 807..813 | |
| | note = misc_feature - Xaa can be any naturally occurring amino acid | |

| | | |
|---|---|---|
| REGION | 816..817 | |
| | note = misc_feature - Xaa can be any naturally occurring amino acid | |
| REGION | 819..821 | |
| | note = misc_feature - Xaa can be any naturally occurring amino acid | |
| REGION | 823..827 | |
| | note = misc_feature - Xaa can be any naturally occurring amino acid | |
| SITE | 831 | |
| | note = misc_feature - Xaa can be any naturally occurring amino acid | |
| REGION | 841..842 | |
| | note = misc_feature - Xaa can be any naturally occurring amino acid | |
| REGION | 856..859 | |
| | note = misc_feature - Xaa can be any naturally occurring amino acid | |
| SITE | 861 | |
| | note = misc_feature - Xaa can be any naturally occurring amino acid | |
| SITE | 863 | |
| | note = misc_feature - Xaa can be any naturally occurring amino acid | |
| SITE | 886 | |
| | note = misc_feature - Xaa can be any naturally occurring amino acid | |
| SITE | 895 | |
| | note = misc_feature - Xaa can be any naturally occurring amino acid | |
| SITE | 903 | |
| | note = misc_feature - Xaa can be any naturally occurring amino acid | |
| SITE | 920 | |
| | note = misc_feature - Xaa can be any naturally occurring amino acid | |
| REGION | 924..927 | |
| | note = misc_feature - Xaa can be any naturally occurring amino acid | |
| REGION | 929..930 | |
| | note = misc_feature - Xaa can be any naturally occurring amino acid | |
| REGION | 932..933 | |
| | note = misc_feature - Xaa can be any naturally occurring amino acid | |
| REGION | 937..938 | |
| | note = misc_feature - Xaa can be any naturally occurring amino acid | |
| SITE | 950 | |
| | note = misc_feature - Xaa can be any naturally occurring amino acid | |
| SITE | 957 | |
| | note = misc_feature - Xaa can be any naturally occurring amino acid | |
| SITE | 959 | |
| | note = misc_feature - Xaa can be any naturally occurring amino acid | |
| REGION | 963..965 | |
| | note = misc_feature - Xaa can be any naturally occurring amino acid | |
| SITE | 972 | |
| | note = misc_feature - Xaa can be any naturally occurring amino acid | |
| SITE | 975 | |
| | note = misc_feature - Xaa can be any naturally occurring amino acid | |
| SITE | 978 | |
| | note = misc_feature - Xaa can be any naturally occurring amino acid | |
| REGION | 981..982 | |
| | note = misc_feature - Xaa can be any naturally occurring amino acid | |
| REGION | 995..997 | |
| | note = misc_feature - Xaa can be any naturally occurring amino acid | |

-continued

| | | |
|---|---|---|
| REGION | 1020..1021 | |
| | note = misc_feature - Xaa can be any naturally occurring amino acid | |
| SITE | 1025 | |
| | note = misc_feature - Xaa can be any naturally occurring amino acid | |
| REGION | 1041..1042 | |
| | note = misc_feature - Xaa can be any naturally occurring amino acid | |
| SITE | 1076 | |
| | note = misc_feature - Xaa can be any naturally occurring amino acid | |
| SITE | 1080 | |
| | note = misc_feature - Xaa can be any naturally occurring amino acid | |
| SITE | 1095 | |
| | note = misc_feature - Xaa can be any naturally occurring amino acid | |
| REGION | 1105..1106 | |
| | note = misc_feature - Xaa can be any naturally occurring amino acid | |
| SITE | 1112 | |
| | note = misc_feature - Xaa can be any naturally occurring amino acid | |
| SITE | 1115 | |
| | note = misc_feature - Xaa can be any naturally occurring amino acid | |
| SITE | 1140 | |
| | note = misc_feature - Xaa can be any naturally occurring amino acid | |
| SITE | 1144 | |
| | note = misc_feature - Xaa can be any naturally occurring amino acid | |
| SITE | 1165 | |
| | note = misc_feature - Xaa can be any naturally occurring amino acid | |
| SITE | 1181 | |
| | note = misc_feature - Xaa can be any naturally occurring amino acid | |
| SITE | 1185 | |
| | note = misc_feature - Xaa can be any naturally occurring amino acid | |
| SITE | 1194 | |
| | note = misc_feature - Xaa can be any naturally occurring amino acid | |
| SITE | 1197 | |
| | note = misc_feature - Xaa can be any naturally occurring amino acid | |
| REGION | 1213..1214 | |
| | note = misc_feature - Xaa can be any naturally occurring amino acid | |
| REGION | 1231..1235 | |
| | note = misc_feature - Xaa can be any naturally occurring amino acid | |
| REGION | 1240..1246 | |
| | note = misc_feature - Xaa can be any naturally occurring amino acid | |
| REGION | 1255..1256 | |
| | note = misc_feature - Xaa can be any naturally occurring amino acid | |
| SITE | 1258 | |
| | note = misc_feature - Xaa can be any naturally occurring amino acid | |
| REGION | 1260..1263 | |
| | note = misc_feature - Xaa can be any naturally occurring amino acid | |
| REGION | 1265..1266 | |
| | note = misc_feature - Xaa can be any naturally occurring amino acid | |
| REGION | 1268..1270 | |
| | note = misc_feature - Xaa can be any naturally occurring amino acid | |
| REGION | 1272..1273 | |
| | note = misc_feature - Xaa can be any naturally occurring amino acid | |

-continued

```
SITE            1275
                note = misc_feature - Xaa can be any naturally occurring
                    amino acid
REGION          1277..1278
                note = misc_feature - Xaa can be any naturally occurring
                    amino acid
REGION          1280..1281
                note = misc_feature - Xaa can be any naturally occurring
                    amino acid
REGION          1283..1284
                note = misc_feature - Xaa can be any naturally occurring
                    amino acid
SITE            1295
                note = misc_feature - Xaa can be any naturally occurring
                    amino acid
REGION          1298..1299
                note = misc_feature - Xaa can be any naturally occurring
                    amino acid
SITE            1315
                note = misc_feature - Xaa can be any naturally occurring
                    amino acid
REGION          1320..1321
                note = misc_feature - Xaa can be any naturally occurring
                    amino acid
SITE            1323
                note = misc_feature - Xaa can be any naturally occurring
                    amino acid
REGION          1325..1328
                note = misc_feature - Xaa can be any naturally occurring
                    amino acid
SITE            1330
                note = misc_feature - Xaa can be any naturally occurring
                    amino acid
SITE            1336
                note = misc_feature - Xaa can be any naturally occurring
                    amino acid
SITE            1339
                note = misc_feature - Xaa can be any naturally occurring
                    amino acid
SITE            1341
                note = misc_feature - Xaa can be any naturally occurring
                    amino acid
SITE            1343
                note = misc_feature - Xaa can be any naturally occurring
                    amino acid
REGION          1345..1348
                note = misc_feature - Xaa can be any naturally occurring
                    amino acid
REGION          1350..1351
                note = misc_feature - Xaa can be any naturally occurring
                    amino acid
SITE            1359
                note = misc_feature - Xaa can be any naturally occurring
                    amino acid
source          1..1360
                mol_type = protein
                organism = synthetic construct
SEQUENCE: 1
MKEKRXXXXX PXVXPKXXXX XXWDDXDXPX XXXXIKRQSI DHGVGXEXXX XXEXXXXXXF      60
RKYNSQGFKA KDTDLMGTXL XXXXEXELXX XXXXXADQQX XXSAXXERKK XPTXXXLDPX     120
XEPXIFXILD TDYXIXPAQX VXXGXXDTED GKPVIRXFGK KENGEFKIEY DRTFEPYFYA     180
LLXXGXXKDD LSAIEEVKKI TAERHXRXGX ETXVRVVDAE EVVKKFEPLG LEXXRPIEVW     240
KLYFXHPQDV PAIRDKIREH PAVVXXXGXX DIXXYEYDIP FAKRYLIDKG LIPPMSWVXM     300
EGDKXXXGRL LNXXSXCQLE XXXXXSDXXV HPXXXXRLEE LPDYIPPLKV LAFDIETLYH     360
XELGSFPEPG KGXRPIIAIT HYDSIDDRFY VFDMISSAYA DEEEARPFLX XVITWKNIDX     420
LPYEIXDXVD VVSFDTEREM LKRFLXXXXE KDPDVIIGYN GDNFDXPYLK KRAEKLKVXX     480
XGIPLXLGRL SXKRSSXDGS VFEPKIQRMY GDRFAVEICL GYKGKGRIHF DLYPVIRRTI     540
FTNYAPFEWNL PSYTLEAVAE ALLGXXKEKX DXXVYAEEIA XAWNEXGENL ERLARYSXED    600
AELTXELGAK KEFLPXEXLI QLSRVXGQPL DWDVSRSSTG NLVEWLLLRK AYERNEVAPN     660
KPSEXEXARR XXXXRESALIK XXXXYPGGYVW LNDRFKEPEX GLYEXNIVXL DFRSLYPSII   720
XTHNLSPDTL LNREGCXPYH XYIXDVAPEE XXVXXXXSGHX FCXTKDPPGF IPSILIKRGD    780
LLEERKKIKK SGGKMXAXXX NXEXIKXXXX XXXLSXXEXX XVXXXXXXFSD XFKKTIDPNT    840
XXIEKKLLDY RQRAIXXXXT XQXNRKILAN SFYGYLGYAK ARWYCXECAE SVTAXGFRQY     900
IEXTIREIEE KFGKVCGTNX EAFXXXXAXX CXXNGYXXGF KVLYGDTDSX FVTIPGXIXK     960
VGXXXFADAE EXKKXILXFK XXEFLKYINA WWREXXXYMN KLPGLLELEY EGFYKRGLFX    1020
XGRGXFVGTK KRYAGLIDEM XXDRFAEGKI TTKGLETVRR DWSELAKETQ ARVLEXILKX    1080
EPEGDVEEAE ESVVXYVKEV IEKLXXYEVP PXAGXIEKLV IHKQLTRDLD DYKATGFPGX    1140
KCPXHVAVAK RLDRANAARG RGVKXRPGTV ISYVILKGGG XIGDXDRAIP PDEXDPXKHK    1200
YDAEYYIENQ VLXXPAVERI LEAFIGDAFA XXXXXRGDHX XXXXXXTGYR KEDLXXFXKX    1260
```

```
XXXCXXCXXX LXXGXGXXCX XCXXRYQKTK QVGLXAWXXL KPKGKRLWTQ CQRCXGNLHX  1320
XVXCXXXXCX IFYMRXKVXK XLXDXXXXLX XFGPPGPFXF                        1360

SEQ ID NO: 2            moltype = AA  length = 773
FEATURE                 Location/Qualifiers
source                  1..773
                        mol_type = protein
                        organism = Thermococcus gorgonarius
SEQUENCE: 2
MILDTDYITE DGKPVIRIFK KENGEFKIDY DRNFEPYIYA LLKDDSAIED VKKITAERHG   60
TTVRVVRAEK VKKKFLGRPI EVWKLYFTHP QDVPAIRDKI KEHPAVVDIY EYDIPFAKRY  120
LIDKGLIPME GDEELKMLAF DIETLYHEGE EFAEGPILMI SYADEEGARV ITWKNIDLPY  180
VDVVSTEKEM IKRFLKVVKE KDPDVLITYN GDNFDFAYLK KRSEKLGVKF ILGREGSEPK  240
IQRMGDRFAV EVKGRIHFDL YPVIRRTINL PTYTLEAVYE AIFGQPKEKV YAEEIAQAWE  300
TGEGLERVAR YSMEDAKVTY ELGKEFFPME AQLSRLVGQS LWDVSRSSTG NLVEWFLLRK  360
AYERNELAPN KPDERELARR RESYAGGYVK EPERGLWENI VYLDFRSLYP SIIITHNVSP  420
DTLNREGCEE YDVAPQVGHK FCKDFPGFIP SLLGDLLEER QKVKKKMKAT IDPIEKKLLD  480
YRQRAIKILA NSFYGYYGYA KARWYCKECA ESVTAWGRQY IETTIREIEE KFGFKVLYAD  540
TDGFFATIPG ADAETVKKKA KEFLDYINAK LPGLLELEYE GFYKRGFFVT KKKYAVIDEE  600
DKITTRGLEI VRRDWSEIAK ETQARVLEAI LKHGDVEEAV RIVKEVTEKL SKYEVPPEKL  660
VIYEQITRDL KDYKATGPHV AVAKRLAARG IKIRPGTVIS YIVLKGSGRI GDRAIPFDEF  720
DPAKHKYDAE YYIENQVLPA VERILRAFGY RKEDLRYQKT RQVGLGAWLK PKT         773

SEQ ID NO: 3            moltype = AA  length = 774
FEATURE                 Location/Qualifiers
source                  1..774
                        mol_type = protein
                        organism = Thermococcus kodakarensis
SEQUENCE: 3
MILDTDYITE DGKPVIRIFK KENGEFKIEY DRTFEPYFYA LLKDDSAIEE VKKITAERHG   60
TVVTVKRVEK VQKKFLGRPV EVWKLYFTHP QDVPAIRDKI REHPAVIDIY EYDIPFAKRY  120
LIDKGLVPME GDEELKMLAF DIETLYEEGE EFAEGPILMI SYADEEGARV ITWKNVDLPY  180
VDVVSTEREM IKRFLVVKE KDPDVLITYN GDNFDFAYLK KRCEKLGINF ALGRDGSEPK   240
IQRMGDRFAV EVKGRIHFDL YPVIRRTINL PTYTLEAVYE AVFGQPKEKV YAEEITTAWE  300
TGENLERVAR YSMEDAKVTY ELGKEFLPME AQLSRLIGQS LWDVSRSSTG NLVEWFLLRK  360
AYERNELAPN KPDEKELARR RQSYEGGYVK EPERGLWENI VYLDFRSLYP SIIITHNVSP  420
DTLNREGCKE YDVAPQVGHR FCKDFPGFIP SLLGDLLEER QKIKKKMKAT IDPIERKLLD  480
YRQRAIKILA NSYYGYYGYA RARWYCKECA ESVTAWGREY ITMTIKEIEE KYGFKVIYSD  540
TDGFFATIPG ADAETVKKKA MEFLKYINAK LPGALELEYE GFYERGFFVT KKKYAVIDEE  600
GKITTRGLEI VRRDWSEIAK ETQARVLEAL LKDGDVEKAV RIVKEVTEKL SKYEVPPEKL  660
VIHEQITRDL KDYKATGPHV AVAKRLAARG VKIRPGTVIS YIVLKGSGRI GDRAIPFDEF  720
DPTKHKYDAE YYIENQVLPA VERILRAFGY RKEDLRYQKT RQVGLSAWLK PKGT        774

SEQ ID NO: 4            moltype = AA  length = 775
FEATURE                 Location/Qualifiers
source                  1..775
                        mol_type = protein
                        organism = Thermococcus sp.
SEQUENCE: 4
MILDTDYITE NGKPVIRVFK KENGEFKIEY DRTFEPYFYA LLKDDSAIED VKKVTAKRHG   60
TVVKVKRAEK VQKKFLGRPI EVWKLYFNHP QDVPAIRDKI RAHPAVVDIY EYDIPFAKRY  120
LIDKGLIPME GDEELTMLAF DIETLYHEGE EFGTGPILMI SYADGSEARV ITWKKIDLPY  180
VDVVSTEKEM IKRFLRVVRE KDPDVLITYN GDNFDFAYLK KRCEELGIKF TLGRDGSEPK  240
IQRMGDRFAV EVKGRIHFDL YPVIRRTINL PTYTLEAVYE AVFGKPKEKV YAEEIAQAWE  300
SGEGLERVAR YSMEDAKVTY ELGKEFFPME AQLSRLIGQS LWDVSRSSTG NLVEWFLLRK  360
AYKRNELAPN KPDERELARR RGGYAGGYVK EPERGLWDNI VYLDFRSLYP SIIITHNVSP  420
DTLNREGCKE YDVAPEVGHK FCKDFPGFIP SLLGDLLEER QKIKRKMKAT VDPLEKKLLD  480
YRQRAIKILA NSFYGYYGYA KARWYCKECA ESVTAWGREY IEMVIRELEE KFGFKVLYAD  540
TDGLHATIPG ADAETVKKKA KEFLKYINPK LPGLLELEYE GFYVRGFFVT KKKYAVIDEE  600
GKITTRGLEI VRRDWSEIAK ETQARVLEAI LKHGDVEEAV RIVKEVTEKL SKYEVPPEKL  660
VIHEQITRDL RDYKATGPHV AVAKRLAARG VKIRPGTVIS YIVLKGSGRI GDRAIPADEF  720
DPTKHRYDAE YYIENQVLPA VERILKAFGY RKEDLRYQKT KQVGLGAWLK VKGKK       775

SEQ ID NO: 5            moltype = AA  length = 775
FEATURE                 Location/Qualifiers
source                  1..775
                        mol_type = protein
                        organism = Pyrococcus furiosus
SEQUENCE: 5
MILDVDYITE EGKPVIRLFK KENGKFKIEH DRTFRPYIYA LLRDDSKIEE VKKITGERHG   60
KIVRIVDVEK VEKKFLGKPI TVWKLYLEHP QDVPTIREKV REHPAVVDIF EYDIPFAKRY  120
LIDKGLIPME GEEELKILAF DIETLYHEGE EFGKGPIIMI SYADENEAKV ITWKNIDLPY  180
VEVVSSEREM IKRFLRIIRE KDPDIIVTYN GSDFDFPYLA KRAEKLGIKL TIGRDGSEPK  240
MQRIGDMTAV EVKGRIHFDL YHVITRTINL PTYTLEAVYE AIFGKPKEKV YADEIAKAWE  300
SGENLERVAK YSMEDAKATY ELGKEFLPME IQLSRLVGQP LWDVSRSSTG NLVEWFLLRK  360
AYERNEVAPN KPSEEEYQRR LRESYTGGFV KEPEKGLWEN IVYLDFRALY PSIIITHNVS  420
PDTLNLEGCK NYDIAPQVGH KFCKDIPGFI PSLLGHLLEE RQKIKTKMKE TQDPIEKILL  480
DYRQKAIKLL ANSFYGYYGY AKARWYCKEC AESVTAWGRK YIELVWKELE EKFGFKVLYI  540
DTDGLYATIP GGESEEIKKK ALEFVKYINS KLPGLLELEY EGFYKRGFFV TKKRYAVIDE  600
```

```
EGKVITRGLE IVRRDWSEIA KETQARVLET ILKHGDVEEA VRIVKEVIQK LANYEIPPEK    660
LAIYEQITRP LHEYKAIGPH VAVAKKLAAK GVKIKPGMVI GYIVLRGDGP ISNRAILAEE    720
YDPKKHKYDA EYYIENQVLP AVLRILEGFG YRKEDLRYQK TRQVGLTSWL NIKKS         775

SEQ ID NO: 6              moltype = AA  length = 774
FEATURE                   Location/Qualifiers
source                    1..774
                          mol_type = protein
                          organism = Thermococcus litoralis
SEQUENCE: 6
MILDTDYITK DGKPIIRIFK KENGEFKIEL DPHFQPYIYA LLKDDSAIEE IKAIKGERHG     60
KTVRVLDAVK VRKKFLGREV EVWKLIFEHP QDVPAMRGKI REHPAVVDIY EYDIPFAKRY    120
LIDKGLIPME GDEELKLLAF DIETFYHEGD EFGKGEIIMI SYADEEEARV ITWKNIDLPY    180
VDVVSNEREM IKRFVQVVKE KDPDVIITYN GDNFDLPYLI KRAEKLGVRL VLGRDKEHPE    240
PKIQRMGDSF AVEIKGRIHF DLFPVVRRTI NLPTYTLEAV YEAVLGKTKS KLGAEEIAAI    300
WETEESMKKL AQYSMEDARA TYELGKEFFP MEAELAKLIG QSVWDVSRSS TGNLVEWYLL    360
RVAYARNELA PNKPDEEEYK RRLRTTYLGG YVKEPEKGLW ENIIYLDFRS LYPSIIVTHN    420
VSPDTLEKEG CKNYDVAPIV GYRFCKDFPG FIPSILGDLI AMRQDIKKKM KSTIDPIEKK    480
MLDYRQRAIK LLANSYYGYM GYPKARWYSK ECAESVTAWG RHYIEMTIRE IEEKFGPKVL    540
YADTDGFYAT IPGEKPELIK KKAKEFLNYI NSKLPGLLEL EYEGFYLRGF FVTKKRYAVI    600
DEEGRITTRG LEVVRRDWSE IAKETQAKVL EAILKEGSVE KAVEVVRDVV EKIAKYRVPL    660
EKLVIHEQIT RDLKDYKAIG PHVAIAKRLA ARGIKVKPGT IISYIVLKGS GKISDRVILL    720
TEYDPRKHKY DPDYYIENQV LPAVLRILEA FGYRKEDLRY QSSKQTGLDA WLKR          774

SEQ ID NO: 7              moltype = AA  length = 937
FEATURE                   Location/Qualifiers
source                    1..937
                          mol_type = protein
                          organism = Methanosarcina acetivorans
SEQUENCE: 7
MPMDFQILDA DYEVVNDSGP VIRLFGRGAD GKSVCCFVPD FEPYFYLKAS GDLHAVARLI     60
KDTFEQVKKV EIVEKFEPVG YQKTKKEMLR VTTRLPKDVP EIRDEILKIR DVLRAEGDWQ    120
VYESDILFRN RFLIDRALGG MVWVSAEGKP VDPVRYLGAG SAWRSRCENF ACDSAVLASG    180
LKRVENLAIA PLKYLAFDIE CLPLDGGMPS PDVSPIIMIS FSFEPEYKGH KTLILLAKPA    240
AGMDGDVLSC MDETEMLNKF FEIICEYDPD IVAGYNHQDF DIPYITERVK ALVAKGETIN    300
SVVGRDGSPI GYRKFGLITR TEMKGRVVVD ALPLVRRAFS LKQYTLRAVS KELLSREKLD    360
VPPLEMEEHW NDSGDKFRKF VDYARRDSEL ALELVLELRL LDKYIALAQV SGSLLQEIVD    420
GGQTSMVETL LLREFGLKDR VILPKPGDEL SAERYDMSSD KLGGEVLEPK KGLLENVLIL    480
DYKSLYPTIM MAHNLCYTTV VTRDRPDGKT IKPPSGGEFV PPEVFRGIVP SILEDLLNKR    540
GDTKKRMKRT SDENEHRVLD ATQLAIKILL NSFYGYSGYA RARLYSLTLA NAVTSFGRSN    600
ILNTRDLING RIGKIVLRNS AALLLEEAGK LSPQDRIVEL SVAYGDTDSV FVHCKAKGDL    660
SLEEVSLVGN RLSEIVSASL PDPMELEFES VAKRALLIAK KRYALWLFEP RNSGWENKIK    720
VKGMETVRRD WCELTSITLN RVLEFVLIEG DVDKAVEHVR KVVSDVRNLD PGKDAGIIEK    780
LVLTRTLTRK ADSYKNKQPH LTVAENLKKR TGIMPSIGTR IPPVITAGKG LFVDRAEDPD    840
YVRENNVPID VDYYVKKQIL PPVERILEVF GVKMSSLDFD AKQKGLFDFE VKKPEAKKQE    900
KSSSQKGTNG KILEKAPEEK ARYSENGRVE QRSLFDF                            937

SEQ ID NO: 8              moltype = AA  length = 785
FEATURE                   Location/Qualifiers
source                    1..785
                          mol_type = protein
                          organism = Pyrobaculum islandicum
SEQUENCE: 8
MELKVWPLDI TYAVVGSVPE IRIFGILSSG ERVVLIDRSF KPYFYVDCAV CEPAALKTAL     60
SRVAPIDDVQ IVERRFLGRS KKFLKVIAKI PEDVRKLREA AMSIPRVSGV YEADIRFYMR    120
YMIDMGVVPC SWNVAEVEEG GRLGGIPTYV VSQWYGIDEG FPPSLKVMAF DIEVYNERGS    180
PDPIRDPVVM LAIKTNDGHE EVFEASGKDD RGVVRAVDF IRSYDPDVIV GYNSNGFDWP    240
YLVERAKAVG VPLKVDRLSN PPQQSVYGHW SIVGRANVDL YNIVEEFPEI KLKTLDRVAE    300
YFGVMKREER VLIPGHKIYE YWKDPNKRPL LKRYVLDVR STLGLADKLL PPLIQLSSVS    360
GLPLDQVAAA SVGNREWML LRYAYRLGEV APNREEREYE PYKGAIVLEP KPGMYEDVLV    420
LDFSSMYPNI MMKYNLSPDT YLEPGEPDPP EGVNVAPEVG HRFRRSPPGF VPQVLKSLVE    480
LRKAVREEAK KYPPDSPEFK ILDERQRALK VMANAIYGYL GWVGARWYKR EVAESVTAFA    540
RAILKDVIEQ ARRLGIVVVY GDTDSLFVKK HGDVDKLIVK VEEKYGIDIK VDKDYAKVLF    600
TEAKKRYAGL LRDGRIDIVG FEVVRGDWSE LAKDVQLRVI EIILKSRDIV EARHGVIKYI    660
REIIERLKNY KFNIDDLIIW KTLDKELDEY KAYPPHVHAA QILKRHGYRV GKGTTIGYVI    720
VKGGEKVSER ALPYILLDDI KKIDIDYYIE RQIIPAALRI AEVIGVKESD LKTGRMERSL    780
LDFLS                                                               785

SEQ ID NO: 9              moltype = AA  length = 882
FEATURE                   Location/Qualifiers
source                    1..882
                          mol_type = protein
                          organism = Sulfolobus solfataricus
SEQUENCE: 9
MTKQLTLFDI PSSKPAKSEQ NTQQSQQSAP VEEKKVVRRE WLEEAQENKI YFLLQVDYDG     60
KKGKAVCKLF DKETQKIYAL YDNTGHKPYF LVDLEPDKVG KIPKIVRDPS FDHIETVSKI    120
DPYTWNKFKL TKIVVRDPLA VRRLRNDVPK AYEAHIKYFN NYMYDIGLIP GMPYVVKNGK    180
LESVYLSLDE KDVEEIKKAF ADSDEMTRQM AVDWLPIFET EIPKIKRVAI DIEVYTPVKG    240
RIPDSQKAEF PIISIALAGS DGLKKVLVLN RNDVNEGSVK LDGISVERFN TEYELLGRFF    300
```

```
DILLEYPIVL TFNGDDFDLP YIYFRALKLG YFPEEIPIDV AGKDEAKYLA GLHIDLYKFF   360
FNKAVRNYAF EGKYNEYNLD AVAKALLGTS KVKVDTLISF LDVEKLIEYN FRDAEITLQL   420
TTFNNDLTMK LIVLFSRISR LGIEELTRTE ISTWVKNLYY WEHRKRNWLI PLKEEILAKS   480
SNIRTSALIK GKGYKGAVVI DPPAGIFFNI TVLDFASLYP SIIRTWNLSY ETVDIQQCKK   540
PYEVKDETGE VLHIVCMDRP GITAVITGLL RDFRVKIYKK KAKNPNNSEE QKLLYDVVQR   600
AMKVFINATY GVFGAETFPL YAPAVAESVT ALGRYVITST VKKAREEGLT VLYGDTDSLF   660
LLNPPKNSLE NIIKWVKTTF NLDLEVDKTY KFVAFSGLKK NYFGVYQDGK VDIKGMLVKK   720
RNTPEFVKKV FNEVKELMIS INSPNDVKEI KRKIVDVVKG SYEKLKNKGY NLDELAFKVM   780
LSKPLDAYKK NTPQHVKAAL QLRPFGVNVL PRDIIYYVKV RSKDGVKPVQ LAKVTEIDAE   840
KYLEALRSTF EQILRAFGVS WDEIAATMSI DSFFSYPSKG NS                     882

SEQ ID NO: 11          moltype = AA    length = 784
FEATURE                Location/Qualifiers
source                 1..784
                       mol_type = protein
                       organism = Methanococcus maripaludis
SEQUENCE: 10
MESLIDLDYN SDDLCIYLYL INSIIKEKDF KPYFYVNSTD KEQILEFLKD YEKKHKLDSE    60
ISKMIENIET VKKIVFDENY QEKELSKVTV KYPNNVKTVR EILMEFERLY EYDIPFVRRY   120
LIDNSVIPTS TWDFENNKKI DNKIPDFKTV SFDIEVYCNK EPNPKKDPII MASFSSKDFN   180
TVVSTKKFDH EKLEYVKDEK ELIKRIIEIL KEYDIIYTYN GDNFDFPYLK KRAESFGLEL   240
KLGKNDEKIK ITKGGMNSKS YIPGRVHIDL YPIARRLLNL TKYRLENVTE ALFDVKKVDV   300
GHENIPKMWD NLDETLVEYS HQDAYYTQRI GEQFLPLEIM FSRVVNQSLY DINRMSSSQM   360
VEYLLLKNSY KMGVIAPNRP SGKEYQKRIR SSYEGGYVKE PLKGIHEDIV SMDFLSLYPS   420
IIMSHNLSPE TIDCTCCSDE ENGENEEILG HKFCKKSIGI IPKTLMDLIN RRKKVKKVLR   480
EKAEKGEFDE EYQILDYEQR SIKVLANSHY GYLAFPMARW YSRDCAEITT HLGRQYIQKT   540
IEEAENFGFK VIYADTGFY SKWADDKEKL SKYELLEKTR EFLKNINNTL PGEMELEFEG   600
YPFKRGIFVTK KKYALIDENE KITVKGLEVV RRDWSNVSKN TQKNVLNALL KEGSVENAKK   660
VIQDTIKELK DGKVNNEDLL IHTQLTKRIE DYKTTAPHVE VAKKILKSGN RVNTGDVISY   720
IITSGNKSIS ERAEILENAK NYDTNYYIEN QILPPVIRLM EALGITKDEL KDSKKQYTLH   780
HFLK                                                              784

SEQ ID NO: 11          moltype = AA    length = 1107
FEATURE                Location/Qualifiers
source                 1..1107
                       mol_type = protein
                       organism = Homo sapiens
SEQUENCE: 11
MDGKRRPGPG PGVPPKRARG GLWDDDDAPR PSQFEEDLAL MEEMEAEHRL QEQEEEELQS    60
VLEGVADGQV PPSAIDPRWL RPTPPALDPQ TEPLIFQQLE IDHYVGPAQP VPGGPPPSRG   120
SVPVLRAFGV TDEGFSVCCH IHGFAPYFYT PAPPGFGPEH MGDLQRELNL AISRDSGGR   180
ELTGPAVLAV ELCSRESMFG YHGHGPSPFL RITVALPRLV APARRLLEQG IRVAGLGTPS   240
FAPYEANVDF EIRFMVDTDI VGCNWLELPA GKYALRLKEK ATQCQLEADV LWSDVVSHPP   300
EGPWQRIAPL RVLSFDIECA GRKGIFPEPE RDPVIQICSL GLRWGEPEPF LRLALTLRPC   360
APILGAKVQS YEKEEDLLQA WSTFIRIMDP DVITGYNIQN FDLPYLISRA QTLKVQTFPF   420
LGRVAGLCSN IRDSSFQSKQ TGRRDTKVVS MVGRVQMDML QVLLREYKLR SYTLNAVSFH   480
FLGEQKEDVQ HSIITDLQNG NDQTRRRLAV YCLKDAYLPL RLLERLMVLV NAVEMARVTG   540
VPLSYLLSRG QQVKVVSQLL RQAMHEGLLM PVVKSEGGED YTGATVIEPL KGYYDVPIAT   600
LDFSSLYPSI MMAHNLCYTT LLRPGTAQKL GLTEDQFIRT PTGDEFVKTS VRKGLLPQIL   660
ENLLSARKRA KAELAKETDP LRRQVLDGRQ LALKVSANSV YGFTGAQVGK LPCLEISQSV   720
TGFGRQMIEK TKQLVESKYT VENGYSTSAK VVYGDTDSVM CRFGVSSVAE AMALGREAAD   780
WVSGHFPSPI RLEFEKVYFP YLLISKKRYA GLLFSSRPDA HDRMDCKGLE AVRRDNCPLV   840
ANLVTASLRR LLIDRDPEGA VAHAQDVISD LLCNRIDISQ LVITKELTRA ASDYAGKQAH   900
VELAERMRKR DPGSAPSLGD RVPYVIISAA KGVAAYMKSE DPLFVLEHSL PIDTQYYLEQ   960
QLAKPLLRIF EPILGEGRAE AVLLRGDHTR CKTVLTGKVG GLLAFAKRRN CCIGCRTVLS  1020
HQGAVCEFCQ PRESELYQKE VSHLNALEER FSRLWTQCQR CQGSLHEDVI CTSRDCPIFY  1080
MRKKVRKDLE DQEQLLRRFG PPGPEAW                                     1107

SEQ ID NO: 12          moltype = AA    length = 1097
FEATURE                Location/Qualifiers
source                 1..1097
                       mol_type = protein
                       organism = Saccharomyces cerevisiae
SEQUENCE: 12
MSEKRSLPMV DVKIDDEDTP QLEKKIKRQS IDHGVGSEPV STIEIIPSDS FRKYNSQGFK    60
AKDTDLMGTQ LESTFEQELS QMEHDMADQE EHDLSSFERK KLPTDFDPSL YDISFQQIDA   120
EQSVLNGIKD ENTSTVVRFF GVTSEGHSVL CNVTGFKNYL YVPAPNSSDA NDQEQINKFV   180
HYLNETFDHA IDSIKIVVSK SIWGYSGDTK LPFWKIYVTY PHMVNKLRTA FERGHLSFNS   240
WFSNGTTTYD NIAYTLRLMV DCGIVGMSWI TLPKGKYSMI EPNNRVSSCQ LEVSINYRNL   300
IAHPAEGDWS HTAPLRIMSF DIECAGRIGV FPEPEYDPVI QIANVVSIAG AKKPFIRNVF   360
TLNTCSPITG SMIFSHATEE EMLSNWRNFI IKVDPDVIIG YNTTNFDIPY LLNRAKALKV   420
NDFPYFGRLK TVKQEIKESV FSSKAYGTRE TKNVNIDGRL QLDLLQFIQR EYKLRSYTLN   480
AVSAHFLGEQ KEDVHYSIIS DLQNGDSETR RRLAVYCLKD AYLPLRLMEK LMALVNYTEM   540
ARVTGVPFSY LLARGQQIKV VSQLFRKCLE IDTVIPNMQS QASDDQYEGA TVIEPIRGYY   600
DVPIATLDFN SLYPSIMMAH NLCYTTLCNK ATVERLNLKI DEDYVITPNG DYFVTTKRRR   660
GILPIILDEL ISARKRAKKD LRDEKDPFKR DVLNGRQLAL KISANSVGYF TGATVGKLPC   720
LAISSSVTAY GRTMILKTKT AVQEKYCIKN GYKHDAVVVY GDTDSVMKF GTTDLKEAMD   780
LGTEAAKYVS TLFKHPINLE FEKAYFPYLL INKKRYAGLF WTNPDKFDKL DQKGLASVRR   840
DSCSLVSIVM NKVLKKILIE RNVDGALAFV RETINDILHN RVDISKLIIS KTLAPNYTNP   900
```

```
QPHAVLAERM KRREGVGPNV GDRVDYVIIG GNDKLYNRAE DPLFVLENNI QVDSRYYLTN    960
QLQNPIISIV APIIGDKQAN GMFVVKSIKI NTGSQKGGLM SFIKKVEACK SCKGPLRKGE   1020
GPLCSNCLAR SGELYIKALY DVRDLEEKYS RLWTQCQRCA GNLHSEVLCS NKNCDIFYMR   1080
VKVKKELQEK VEQLSKW                                                 1097

SEQ ID NO: 13           moltype = AA   length = 787
FEATURE                 Location/Qualifiers
source                  1..787
                        mol_type = protein
                        organism = Pseudomonas aeruginosa
SEQUENCE: 13
MELLQGFVLT RHWRDTPAGT EVAFWLATEQ GPRQVRLPPQ PSVAFVLAEQ RGRVESLLAG    60
ETGAELRPLA LRDFQQRPVL GLYCQQHRQL MNLEKRLRQA GVEVFEADIR PPERYLMERF   120
ITAPVSLEAS VEADGSLLAR RLKPAPDYRP RLRLVSLDIE TNARGDLYSI ALEGCDQRQV   180
YMLGPANGDA AAVDFRLDYC DSRAGLLERL NQWLAEHDPD AIIGWNLVQF DLRVLHEHAQ   240
RLKVPLRLGR GGDEMGWREH GSRNNHFFAA AAGRLIIDGI EALRSATWSF PSFSLENVAR   300
TLLGEGKAID NPYQRMDEID RMFAEDKPAL AHYNLKDCEL VTRIFARTEL LDFLLERATV   360
TGLPADRSGG SVAAFTHLYM PLMHRAGFVA PNLGEKRPEA SPGGFVMDSR PGLYESVLVL   420
DYKSLYPSII RTFLIDPVGL VEGLRQPDDE HSVEGFRGAR FSRTRHCLPA IVARVWEGRE   480
AAKRERNQPL SQALKIIMNA FYGVLGSSGC RFFDPRLASS ITLRGHRIMR RTRELIEAEG   540
YTVIYGDTDS TFVWLGSPRA EEEAAAIGRA LVARVNDWWR EHLKEEFGLD SALELQFETH   600
YRRFLMPTVR GAEEGSKKRY AGLVRRADGG EEMVFKGLET VRTDWSPLAQ RFQQELYLRI   660
FNRQPYQDYV RDYVRRTLAG ELDDLLVYRK RLRRRLDDYQ RNVPPHVRAA RIADDYNLER   720
GRPRQYQSGG WISYVISVAG PEPLEARRSA IDYEHYVGKQ LQPVADAILP FVGDDFATLV   780
DRQMALF                                                            787

SEQ ID NO: 14           moltype = AA   length = 783
FEATURE                 Location/Qualifiers
source                  1..783
                        mol_type = protein
                        organism = Escherichia coli
SEQUENCE: 14
MAQAGFILTR HWRDTPQGTE VSFWLATDNG PLQVTLAPQE SVAFIPADQV PRAQHILQGE    60
QGFRLTPLAL KDFHRQPVYG LYCRAHRQLM NYEKRLREGG VTVYEADVRP PERYLMERFI   120
TSPVVWVEGDM HNGTIVNARL KPHPDYRPPL KWVSIDIETT RHGELYCIGL EGCGQRIVYM   180
LGPENGDASS LDFELEYVAS RPQLLEKLNA WFANYDPDVI IGWNVVQFDL RMLQKHAERY   240
RLPLRLGRDN SELEWREHGF KNGVFFAQAK GRLIIDGIEA LKSAFWNFSS FSLETVAQEL   300
LGEGKSIDNP WDRMDEIDRR FAEDKPALAT YNLKDCELVT QIFHKTEIMP FLLERATVG   360
LPVDRHGGSV AAFGHLYFPR MHRAGYVAPN LGEVPPHASP GGYVMDSRPG LYDSVLVLDY   420
KSLYPSIIRT FLIDPVGLVE GMAQPDPEHS TEGFLDAWFS REKHCLPEIV TNIWHGRDEA   480
KRQGNKPLSQ ALKIIMNAFY GVLGTTACRF FDPRLASSIT MRGHQIMRQT KALIEAQGYD   540
VIYGDTSTF VWLKGAHSEE EAAKIGRALV QHVNAWWAET LQKQRLTSAL ELEYETHFCR    600
FLMPTIRGAD TGSKKRYAGL IQEGDKQRMV FKGLETVRTD WTPLAQQFQQ ELYLRIFRNE   660
PYQEYVRETI DKLMAGELDA RLVYRKRLRR PLSEYQRNVP PHVRAARLAD EENQKRGRPL   720
QYQNRGTIKY VWTTNGPEPL DYQRSPLDYE HYLTRQLQPV AEGILPFIED NFATLMTGQL   780
GLF                                                                783

SEQ ID NO: 15           moltype = AA   length = 903
FEATURE                 Location/Qualifiers
source                  1..903
                        mol_type = protein
                        organism = unidentified
SEQUENCE: 15
MKEFYLTVEQ IGDSIFERYI DSNGRERTRE VEYKPSLFAH CPESQATKYF DIYGKPCTRK    60
LFANMRDASQ WIKRMEDIGL EALGMDDFKL AYLSDTYNYE IKYDHTKIRV ANFDIEVTSP   120
DGFPEPSQAK HPIDAITHYD SIDDRFYVFD LLNSPYGNVE EWSIEIAAKL QEQGGDEVPS   180
EIIDKIIYMP FDNEKELLME YLNFWQQKTP VILTGWNVES FDIPYVYNRI KNIFGESTAK   240
RLSPHRKTRV KVIENMYGSR EIITLFGISV LDYIDLYKKF SFTNQPSYSL DYISEFELNV   300
GKLKYDGPIS KLRESNHQRY ISYNIIDVYR VLQIDAKRGF INLSLDMGYY AKIQIQSVFS   360
PIKTWDAIIF NSLKEQNKVI PQGRSHPVQP YPGAFVKEPI PNRYKYVMSF DLTSLYPSII   420
RQVNISPETI AGTFKVAPLH DYINAVAERP SDVYSCSPNG MMYYKDRDGV VPTEITKVFN   480
QRKEHKGYML AAQRNGEIIK EALHNPNLSV DEPLDVDYRF DFSDEIKEKI KKLSAKSLNE   540
MLFRAQRTEV AGMTAQINRK LLINSLYGAL GNVWFRYYDL RNATAITTFG QMALQWIERK   600
VNEYLNEVCG TEGEAFVLYG DTDSIYVSAD KIIDKVGESK FRDTNHWVDF LDKFARERME   660
PAIDRGFREM CEYMNNKQHL MFMDREAIAG PPLGSKGIGG FWTGKKRYAL NVWDMEGTRY   720
AEPKLKIMGL ETQKSSTPKA VQKALKECIR RMLQEGEESL QEYFKEFEKE FRQLNYISIA   780
SVSSANNIAK YDVGGFPGPK CPFHIRGILT YNRAIKGNID APQVVEGEKV YVLPLREGNP   840
FGDKCIAWPS GTEITDLIKD DVLHWMDYTV LLEKTFIKPL EGFTSAAKLD YEKKASLFDM   900
FDF                                                                903

SEQ ID NO: 16           moltype = AA   length = 898
FEATURE                 Location/Qualifiers
source                  1..898
                        mol_type = protein
                        organism = unidentified
SEQUENCE: 16
MKEFYISIET VGNNIVERYI DENGKERTRE VEYLPTMFRH CKEESYKYDI YGKNCAPQKF    60
PSMKDARDWM KRMEDIGLEA LGMNDFKLAY ISDTYGSEIV YDRKFVRVAN CDIEVTGDKF   120
PDPMKAEYEI DAITHYDSID DRFYVFDLLN SMYGSVSKWD AKLAAKLDCE GGDEVPQEIL   180
```

```
DRVIYMPFDN ERDMLMEYIN LWEQKRPAIF TGWNIEGFDV PYIMNRVKMI LGERSMKRFS   240
PIGRVKSKLI QNMYGSKEIY SIDGVSILDY LDLYKKFAFT NLPSFSLESV AQHETKKGKL   300
PYDGPINKLR ETNHQRYISY NIIDVESVQA IDKIRGFIDL VLSMSYYAKM PFSGVMSPIK   360
TWDAIIFNSL KGEHKVIPQQ GSHVKQSFPG AFVFEPKPIA RRYIMSFDLT SLYPSIIRQV   420
NISPETIRGQ FKVHPIHEYI AGTAPKPSDE YSCSPNGWMY DKHQEGIIPK EIAKVFFQRK   480
DWKKKMFAEE MNAEAIKKII MKGAGSCSTK PEVERYVKFS DDFLNELSNY TESVLNSLIE   540
ECEKAATLAN TNQLNRKILI NSLYGALGNI HFRYYDLRNA TAITIFGQVG IQWIARKINE   600
YLNKVCGTND EDFIAAGDTD SVYVCVDKVI EKVGLDRFKE QNDLVEFMNQ FGKKKMEPMI   660
DVAYRELCDY MNNREHLMHM DREAISCPPL GSKGVGGFWK AKKRYALNVY DMEDKRFAEP   720
HLKIMGMETQ QSSTPKAVQE ALEESIRRIL QEGEESVQEY YKNFEKEYRQ LDYKVIAEVK   780
TANDIAKYDD KGWPGFKCPF HIRGVLTYRR AVSGLGVAPI LDGNKVMVLP LREGNPFGDK   840
CIAWPSGTEL PKEIRSDVLS WIDHSTLFQK SFVKPLAGMC ESAGMDYEEK ASLDFLFG     898

SEQ ID NO: 17           moltype = AA  length = 575
FEATURE                 Location/Qualifiers
source                  1..575
                        mol_type = protein
                        organism = unidentified
SEQUENCE: 17
MKHMPRKMYS CDFETTTKVE DCRVWAYGYM NIEDHSEYKI GNSLDEFMAW VLKVQADLYF    60
HNLKFDGAFI INWLERNGFK WSADGLPNTY NTIISRMGQW YMIDICLGYK GKRKIHTVIY   120
DSLKKLPFPV KKIAKDFKLT VLKGDIDYHK ERPVGYKITP EEYAYIKNDI QIIAEALLIQ   180
FKQGLDRMTA GSDSLKGFKD IITTKKFKKV FPTLSLGLDK EVRYAYRGGF TWLNDRFKEK   240
EIGEGMVFDV NSLYPAQMYS RLLPYGEPIV FEGKYVWDED YPLHIQHIRC EFELKEGYIP   300
TIQIKRSRFY KGNEYLKSSG GEIADLWLSN VDLELMKEHY DLYNVEYISG LKFKATTGLF   360
KDFIDKWTYI KTTSEGAIKQ LAKLMLNSLY GKFASNPVDT GKVPYLKENG ALGFRLGEEE   420
TKDPVYTPMG VFITAWARYT TITAAQACYD RIIYCDTDSI HLTGTEIPDV IKDIVDPKKL   480
GYWAHESTFK RAKYLRQKTY IQDIYMKEVD GKLVEGSPDD YTDIKFSVKC AGMTDKIKKE   540
VTFENFKVGF SRKMKPKPVQ VPGGVVLVDD TFTIK                             575

SEQ ID NO: 18           moltype = DNA  length = 45
FEATURE                 Location/Qualifiers
misc_feature            1..45
                        note = FAM-45-mer DNA initiator
source                  1..45
                        mol_type = other DNA
                        organism = synthetic construct
SEQUENCE: 18
ctcggcctgg cacaggtccg ttcagtgctg cggcgaccac cgagg                    45

SEQ ID NO: 19           moltype = DNA  length = 38
FEATURE                 Location/Qualifiers
misc_feature            1..38
                        note = Cy5-38-mer primer
source                  1..38
                        mol_type = other DNA
                        organism = synthetic construct
SEQUENCE: 19
gcttgcacaa gttcgttcaa tgatacggcg accaccga                            38

SEQ ID NO: 20           moltype = DNA  length = 38
FEATURE                 Location/Qualifiers
misc_feature            1..38
                        note = Complementary 38-mer DNA
source                  1..38
                        mol_type = other DNA
                        organism = synthetic construct
SEQUENCE: 20
tcggtggtcg ccgtatcatt gaacgaactt gtgcaagc                            38
```